(12) United States Patent
Latham et al.

(10) Patent No.: US 8,679,757 B2
(45) Date of Patent: Mar. 25, 2014

(54) PCR METHODS FOR CHARACTERIZING THE 5' UNTRANSLATED REGION OF THE FMR1 AND FMR2 GENES

(75) Inventors: Gary J. Latham, Austin, TX (US); Liangjing Chen, Austin, TX (US); Sachin Sah, Austin, TX (US)

(73) Assignee: Asuragen, Inc., Austin, TX (US)

( * ) Notice: Subject to any disclaimer, the term of this patent is extended or adjusted under 35 U.S.C. 154(b) by 881 days.

(21) Appl. No.: 12/706,472

(22) Filed: Feb. 16, 2010

(65) Prior Publication Data

US 2010/0243451 A1 Sep. 30, 2010

Related U.S. Application Data

(60) Provisional application No. 61/162,977, filed on Mar. 24, 2009.

(51) Int. Cl.
*C12Q 1/68* (2006.01)
*C07H 21/04* (2006.01)

(52) U.S. Cl.
USPC ....................................... 435/6.12; 536/24.33

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 5,648,211 A | 7/1997 | Fraiser et al. | |
| 5,658,764 A | 8/1997 | Pergolizzi et al. | |
| 5,976,842 A | 11/1999 | Wurst | |
| 6,143,504 A | 11/2000 | Das et al. | |
| 6,200,747 B1 | 3/2001 | Pergolizzi et al. | |
| 6,287,824 B1 | 9/2001 | Lizardi | |
| 6,326,173 B1 | 12/2001 | Edman et al. | |
| 6,335,165 B1 | 1/2002 | Navot et al. | |
| 6,410,278 B1 | 6/2002 | Notomi et al. | |
| 6,670,124 B1 | 12/2003 | Chow et al. | |
| 6,881,559 B2 | 4/2005 | Sobek et al. | |
| 7,030,220 B1 | 4/2006 | Ankenbauer et al. | |
| 2008/0124709 A1 | 5/2008 | Huang et al. | |
| 2010/0209970 A1 | 8/2010 | Latham | |

FOREIGN PATENT DOCUMENTS

| | | |
|---|---|---|
| AU | 671418 | 9/1992 |
| WO | WO 92/14840 | 9/1992 |
| WO | WO 93/15225 A1 | 8/1993 |
| WO | WO 00/43531 | 7/2000 |
| WO | WO 2008/011170 | 1/2008 |

OTHER PUBLICATIONS

Debacker et al. The molecular basis of the folate-sensitive fragile site FRA11A at 11q13. Cytogenetic and Genome Research 119:9-14 (2007).*
PCT International Preliminary Report on Patentability and Written Opinion mailed Oct. 6, 2011, in counterpart International Application No. PCT/US2010/000426.

(Continued)

*Primary Examiner* — Samuel Woolwine
(74) *Attorney, Agent, or Firm* — Finnegan, Henderson, Farabow, Garrett & Dunner, LLP

(57) ABSTRACT

This disclosure relates to methods of determining the presence and position of AGG or interruptor elements within a trinucleotide (for example, CGG) repeat region, and to methods of determining the number of repeats present in this region, by amplifying a set of products with a set of primers of which at least one comprises a portion of the CGG repeat region, and resolving the products to produce a representation of product size and abundance.

106 Claims, 21 Drawing Sheets

(56) References Cited

OTHER PUBLICATIONS

Bachinski et al., "Confirmation of the Type 2 Myotonic Dystrophy (CCTG)$_n$ Expansion Mutation in Patients with Proximal Myotonic Myopathy/Proximal Myotonic Dystrophy of Different European Origins: A Single Shared Haplotype Indicates an Ancestral Founder Effect," Am. J. Hum. Genet., 73: 835-848 (2003).
Baskaran et al., "Uniform Amplification of a Mixture of Deoxyribonucleic Acids with Varying GC Content," Genome Res., 6: 633-638 (1996) by Cold Spring Harbor Laboratory Press.
Bell et al., "Physical mapping across the fragile X: hypermethylation and clinical expression of the fragile X syndrome," Cell 64:861-866 (1991).
Bionexus, Inc.: All Purpose Hi-Lo DNA Marker/Mass Ladder (2009).
Blazej et al., "Microfabricated Bioprocessor for Integrated Nanoliter-Scale Sanger DNA Sequencing," Proc. Natl. Acad. Sci. USA, 103: 7240-7245 (2006).
Bodega et al., "Influence of intermediate and uninterrupted FMR1 CGG expansions in premature ovarian failure manifestation," Hum. Reprod., 21(4): 952-957 (2006).
Brown et al., "Rapid fragile X carrier screening and prenatal diagnosis using a nonradioactive PCR test," Journal of the American Medical Association, 270:1569-1575 (1993).
Brown et al., "Prenatal diagnosis and carrier screening for fragile X by PCR," American Journal of Medical Genetics 64:191-195 (1996).
Cadwell et al., "Randomization of Genes by PCR Mutagenesis," PCR Methods Appl. 2: 28-33 (1992) by Cold Spring Harbor Laboratory Press.
Cagnoli et al., "Detection of Large Pathogenic Expansions in FRDA1, SCA10, and SCA12 Genes Using a Simple Fluorescent Repeat-Primed PCR Assay," J. Mol. Diagn., 6: 96-100 (2004).
Cagnoli et al., "Large Pathogenic Expansions in the SCA2 and SCA7 Genes Can Be Detected by Fluorescent Repeat-Primed Polymerase Chain Reaction Assay," J. Mol. Diagn., 8:128-132 (2006).
Cao et al., "A simple fragile X PCR assay with 7-deazaguanine-substituted DNA visualized by ethidium bromide," Molecular and Cellular Probes 8:177-180 (1994).
Chen et al., "An Information-rich CGG repeat primed PCR that detects the full range of fragile X expanded alleles and minimizes the need for southern blot analysis," J. Mol. Diagn., 12:589-600 (2010).
Chiu et al., "The AGG interruption pattern within the CGG repeat of the FMR1 gene among Taiwanese population," Journal of Genetics, 87(3): 275-277 (2008).
Chong et al., "Robust amplification and ethidium-visible detection of the fragile X syndrome CGG repeat using Pfu polymerase," American Journal of Medical Genetics 51:522-526 (1994).
Ciotti et al., "Triplet Repeat Primed PCR (TP PCR) in Molecular Diagnostic Testing for Friedreich Ataxia," J Mol. Diag., 6:285-289 (2004).
Cirino et al., "Generating Mutant Libraries Using Error-Prone PCR," Methods Mol. Biol., 231:3-9 (2003).
Cline et al., "PCR Fidelity of Pfu DNA Polymerase and Other Thermostable DNA Polymerases," Nucleic Acids Res., 24:3546-3551 (1996).
Dean et al., "Instability in the Transmission of the Myotonic Dystrophy CTG Repeat in Human Oocytes and Preimplantation Embroyos," Fertil. Steril., 86:98-105 (2006).
Deiman et al., "Efficient Amplification with NASB® of Hepatitis B Virus, Herpes Simplex Virus and Methicillin Resistant Staphylococcus aureus DNA," J. Virol. Methods, 151:283-293 (2008).
Dewoody et al., "Universal Method for Producing ROX-labeled Size Standards Suitable for Automated Genotyping," Biotechniques, 37:348, 350, 352 (2004).
Dombrowski et al., "Premutation and Intermediate-Size FRM1 Alleles in 10 572 Males from the General Population: Loss of an AGG Interruption is a Late Event in the Generation of Fragile X Syndrome Alleles," Hum. Mol. Genet., 11:371-378 (2002).
Dorschner et al., "Diagnosis of Five Spinocerebellar Ataxia Disorders by Multiplex Amplification and Capillary Electrophoresis," J. Mol. Diag., 4:108-113 (2002).
K. Eckert and T. Kunkel, PCR: A Practical Approach (The Practical Approach Series), Oct. 10, 1991, Chapter 14, pp. 225-246, Oxford University Press.
Eichler et al., "Population Survey of the human FMR1 CGG repeat substructure suggests biased polarity for the loss of AGG interruptions," Human Molecular Genetics, 4(12):2199-2208 (1995).
Eichler et al., "Length of Uninterrupted CGG Repeats Determines Instability in the FMR1 Gene," Nat. Genet., 8:88-94 (1994).
Erster et al., "Polymerase chain reaction analysis of fragile X mutations," Human Genetics 90:55-61 (1992).
Fernandez-Carvajal et al., "Expansion of an FMR1 grey-zone allele to a full mutation in two generations," Journal of Molecular Diagnostics 11(4):306-310 (2009).
Filipovic-Sadic et al., "A Novel FMR1 PCR Method for the Routine Detection of Low Abundance Expanded Alleles and Full Mutations in Fragile X Syndrome," Clinical Chemistry, pp. 399-408 (2010).
Frey et al., "PCR-Amplification of GC-Rich Regions: 'Slowdown PCR'," Nature Publishing Group,3: 1312-1318 (2009).
Fromant et al., "Direct Random Mutagenesis of Gene-Sized DNA Fragments Using Polymerase Chain Reaction," Anal. Biochem., 224:347-353 (1995).
Fu et al., "Variation of the CGG repeat at the fragile X site results in genetic instability: resolution of the Sherman paradox," Cell 67:1047-1058 (1991).
Gecz et al., "Identification of the Genes FMR2, Associated with FRAXE Mental Retardation," Nat. Genet., 13:105-108 (1996).
Gruegelsiepe et al., Handbook of RNA Biochemistry, May 6, 2005, Wiley-VCH, Weinheim, Germany, Chapter 1, pp. 1-21.
Gu et al., "Identification of FMR2, a Novel Gene Associated with the FRAXE CCG Repeat and CpG Island," Nat. Genet., 13: 109-113 (1996).
Hadd et al., "Two Novel PCR Strategies that Amplify and Accurately Report the Full Range of FMR1 Genotypes without the Need for Southern Blot," poster presentation dated Nov. 23, 2009.
Haddad et al., "A PCR-Based Test Suitable for Screening for Fragile X Syndrome Among Mentally Retarded Males," Hum. Genet., 97: 808-812 (1996).
Hamdan et al., "Automated Detection of Trinucleotide Repeats in Fragile X Syndrome," Molecular Diagnosis 2:259-269 (1997).
Hecimovic et al., "A simple and rapid analysis of triplet repeat diseases by expand long PCR," Clinical Chemistry and Lab Medicine 39(12):1259-1262 (2001).
Henke et al., "Betaine Improves the PCR Amplification of GC-Rich DNA Sequences," Nucleic Acids Res., 25: 3957-3958 (1997).
Hirst et al., "Precursor Arrays for Triplet Repeat Expansion at the Fragile X Locus," Hum. Mol. Genet., 3: 1553-1560 (1994).
Houdayer et al., "Improved fluorescent PCR-based assay for sizing CGG repeats at the FRAXA locus," Clinical Chemistry and Lab Medicine 37(4): 397-402 (1999).
Innis et al., "DNA Sequencing with Thermus aquaticus DNA Polymerase and Direct Sequencing of Polymerase Chain Reaction-Amplified DNA," Proc. Natl. Acad. Sci. USA, 85: 9436-9440 (1988).
Jama et al., "Direct PCR From Whole Blood," poster 102808 (2008) at http://www.kapabiosystems.com/public/files/pdfs/.
Johnson et al., "Role of Subunit-9 of Mitochondrial ATP Synthase in Batten Disease," American Journal of Medical Genetics 57:350-360, (1995).
Klepárník et al., "Electromigration Behaviour of DNA Molecules at the Free Electrolyte-Polymer Solution Interface," J. Chromatogr., 772: 243-253 (1997).
Kolesar et al., "Direct Quantification of AD-36 Adenovirus DNA by Capillary Electrophoresis with Laser-Induced Fluorescence," J Chromatography B, pp. 1-8 (2000).
Krafft et al., "Screen for Excess FMR1 Premutation Alleles Among Males with Parkinsonism," Arch. Neurol., 64: 1002-1006 (2007).
Kremer et al., "Mapping of DNA instability at the fragile X to a trinucleotide repeat sequence p(CCG)n," Science 252:1711-1714 (1991).
Kunst et al. "FMR1 in global populations," Am J Hum Genet, 58: 513-522 (1996).

(56) References Cited

OTHER PUBLICATIONS

Kwon et al.,"Molecular Screening for Fragile X Syndrome in Mentally Handicapped Children in Korea," *J Korean Medical Science*, 16: 271-275 (2001).

Larsen et al., "Haplotype and AGG-Interspersion Analysis of *FMR1* (CGG)n. Alleles in the Danish Population: Implications for Multiple Mutational Pathways Towards Fragile X Alleles," *Am. J. Med. Genet.*, 93: 99-106 (2000).

Latham et al., "Evaluation of a Novel FMR1 PCR Assay that Can Amplify Fragile X Full Mutations," abstract published at http://submissions.miracd.com/acmg (Mar. 25, 2009).

Levinson et al., "Improved Sizing of Fragile X CCG Repeats by Nested Polymerase Chain Reaction," *Am. J. Med. Genet.* 51: 527-534 (1994).

Lyon et al., "A Rapid PCR Assay Suitable for Fragile X Population Screening," abstract posted on http://submissions.miracd.com/acmg on or before Mar. 19, 2009.

M. J. McPherson & S. G. Moller, *PCR: The Basics* ($2^{nd}$ Ed., Taylor & Francis) (2006), Chapter 3, pp. 23-63, Chapter 4, pp. 65-85, Chapter 7, pp. 137-183, Chapter 11, pp. 257-281.

Musso et al., "Betaine, Dimethyl Sulfoxide, and 7-Deaza-dGTP, a Powerful Mixture for Amplification of GC-Rich DNA Sequences," *J. Mol. Diagn.*, 8: 544-550 (2006).

Nolin et al., "Expansion of the Fragile X CGG Repeat in Females with Premutation of Intermediate Alleles," *Am. J. Hum. Genet.*, 72: 454-464 (2003).

Oberle et al., "Instability of a 550-base pair DNA segment and abnormal methylation in fragile X syndrome." *Science* 252:1097-1102 (1991).

O'Connell et al., "Standardization of PCR Amplification for Fragile X Trinucleotide Repeat Measurements," *Clin. Genet.* 61:13-20 (2002).

Pembrey et al., "An Assessment of Screening Strategies for Fragile X Syndrome in the UK," *Health Technol. Assess.*, 5:1-95 (2001).

Pergolizzi et al., "Detection of full fragile X mutation," *Lancet* 339:271-272 (1992).

Saluto et al., "An Enhanced Polymerase Chain Reaction Assay to Detect Pre- and Full Mutation Alleles of the *Fragile X Mental Retardation 1* Gene," *J. Mol. Diagn.*, 7: 605-612 (2005).

Saul et al., "Fragile X Syndrome Detection in Newborns—Pilot Study," *Genet. Med.*, 10: 714-719 (2008).

Sermon et al., "Preimplantation Diagnosis for Fragile X Syndrome Based on the Detection of the Non-Expanded Paternal and Maternal CGG," *Prenat Diagn.*, 19: 1223-1230 (1999).

Sermon et al., "PGD in the Lab for Triplet Repeat Diseases—Myotonic Dystrophy, Huntington's Disease and Fragile-X Syndrome," *Mol. Cell. Endocrinol.*, 183: S77-S85 (2001).

Sista et al., "Development of a Digital Microfluidic Platform for Point of Care Testing," *Lab Chip*, 8: 2091-2104 (2008).

Snow et al., "Sequence Analysis of the Fragile X Trinucleotide Repeat: Implications for the Origin of the Fragile X Mutation," *Hum. Mol. Genet.*, 3: 1543-1551 (1994).

Strom et al., "Development of a Novel, Accurate, Automated, Rapid, High-Throughput Technique Suitable for Population-Based Carrier Screening for Fragile X Syndrome," *Genetics in Medicine*, 9: 199-207 (2007).

Tassone et al., "A Rapid Polymerase Chain Reaction-Based Screening Method for Identification of All Expanded Alleles of the Fragile X (*FMR1*) Gene in Newborn and High-Risk Populations," *J. Mol. Diagn.*, 10:43-49 (2008).

Vartanian et al., "Hypermutagenic PCR involving all four transitions and a sizeable proportion of transversions," *Nucleic Acids Research*, 24(14): 2627-2631 (1996).

Vasudevamurthy, Madhusudan, "Betaine Analogues and Related Compounds for Biomedial Applications," *Department of Chemical and Process Engineering*, University of Canterbury, Christchurch, New Zealand (2006).

Verkerk et al., "Identification of a gene (FMR-1) containing a CGG repeat coincident with a breakpoint cluster region exhibiting length variation in fragile X syndrome," *Cell* 65:905-914 (1991).

Vincent et al., "Abnormal pattern detected in fragile-X patients by pulsed-field gel electrophoresis," *Nature* 349:624-626 (1991).

Wallace et al., "Fragile X Analysis: A Multi-Centre Assessment of the Abbott Molecular Fragile X Analyte Specific Reagent (ASR) Kit," *Technology Assessment Report—Abbott Molecular Fragile X ASR*, National Genetics Reference Laboratory, Manchester, UK, Jan. 2008, pp. 1-105.

Wang et al., "A rapid, non-radioactive screening test for fragile X mutations at the FRAXA and FRAXE loci," *Journal of Medical Genetics* 32:170-173 (1995).

Warner et al., "A general method for the detection of large CAG repeat expansions by fluorescent PCR," *J. Med. Genet.*, 33: 1022-1026 (1996).

Weisman-Shomer et al., "Interruption of the Fragile X Syndrome Expanded Sequence $d(CGG)_n$ by Interspersed d(AGG) Trinucleotides Diminishes the Formation and Stability of $d(CGG)_n$ Tetrahelical Structures," *Nucleic Acids Res.*, 28: 1535-41 (2000).

Wilson et al., "Random Mutagenesis by PCR," *Curr. Protoc. Molec. Biol.*, Ch. 8, Unit 8.3, pp. 8.3.1-8.3.9 (2000).

Wilson et al., "Consensus Characterization of 16 FMR1 Reference Materials: A Consortium Study," *J. Mol. Diagn.*, 10: 2-12 (2008) (published online Dec. 28, 2007).

Yu et al.,"Fragile X genotype characterized by an unstable region of DNA," *Science* 252:1179-1181 (1991).

Zhong et al., "Fragile X 'Gray Zone' Alleles: AGG Patterns, Expansion, Risks, and Associated Haplotypes," *Am. J. Med. Genet.*, 64: 261-265 (1996).

Zhong et al., "Fragile X gene instability: anchoring AGGs and linked microsatellites," *Am. J. Hum. Genet.*, 57: 351-361 (1995).

Zhou et al., "Simplified Molecular Diagnosis of Fragile X Syndrome by Fluorescent Methylation-Specific PCR and GeneScan Analysis," *Clinical Chemistry*, 52: 1492-1500 (2006).

Zhou, et al., "Robust Fragile X $(CGG)_n$ Genotype Classification Using a Methylation Specific Triple PCR Assay," *J. Med. Genet.*, 41:e45 (2004), downloaded from http://www.jmg.bmj.com on Sep. 5, 2008.

PCT International Search Report and Written Opinion, for counterpart International Application No. PCT/US2010/000426, dated Jul. 29, 2010.

* cited by examiner

PCR METHODS FOR CHARACTERIZING THE 5' UNTRANSLATED REGION OF THE FMR1 AND FMR2 GENES

CROSS-REFERENCE TO RELATED APPLICATIONS

This application claims the benefit under 35 U.S.C. §119 (e) of U.S. Provisional Application No. 61/162,977, filed Mar. 24, 2009.

DESCRIPTION OF THE INVENTION

1. Field of the Invention

This invention is in the fields of DNA synthesis and analysis, particularly relating to GC-rich templates and products.

2. General Description

Since the first isolation of a DNA polymerase and determination of conditions under which DNA can be synthesized in vitro, DNA synthesis reactions have been widely used for preparative and analytical purposes in biotechnological, medical, and research applications. Polymerase chain reaction, or PCR, is a type of DNA synthesis reaction by which a DNA sequence can be amplified rapidly and exponentially. Like other cycled synthesis reactions, it involves repeatedly copying the target sequence in a cyclic manner. A typical implementation of PCR involves providing primers complementary to the ends of the sequence to be amplified, a suitable buffer, a magnesium salt, deoxynucleotide triphosphates (dNTPs), and a thermophilic DNA polymerase. The template or target DNA, contained, for example, within a sample of genomic DNA, is exposed to these components in aqueous solution. The mixture is cycled through steps at different temperatures which promote denaturation of the template, annealing of the primers to the template, and then extension of the primers by the polymerase, creating more product. Since the product of each cycle is available as template in subsequent reactions, the amount of product increases roughly exponentially until other reaction components (initially present in excess) are depleted. See, e.g., U.S. Pat. No. 4,683,202; M. J. McPherson & S. G. Moller, *PCR: The Basics* (2nd Ed., Taylor & Francis) (2006).

PCR, along with other forms of cycled nucleic acid synthesis reactions, is a standard tool in molecular biology, biotechnology, and, increasingly, in medicine. Key advantages of PCR and related techniques are rapidity, low cost, sensitivity, amenability to high throughput analysis, and versatility. Amplifications require only a few hours or less, small individual reactions may consume well less than a U.S. dollar's worth in reagents, the amount of template required is typically in the nanogram range, automation can result in running thousands of reactions per day per robot, and primers can be designed to amplify almost any sequence.

PCR and related techniques are widely adopted for both analytical and preparative applications. A typical preparative application of PCR is to amplify a sequence so that it may be cloned in a heterologous vector. Notable analytical applications of PCR include diagnoses of conditions or determinations of genotypes involving genetic loci with size polymorphisms.

An example of a locus exhibiting medically relevant size polymorphism is the 5' untranslated region (UTR) of the human FMR1 gene on the X chromosome. Normal individuals typically have 5-44 CGG repeats in this region. In contrast, alleles of this locus containing 200 to 2000 or more CGG repeats are indicative of Fragile X syndrome (FXS). Such alleles are referred to as Full Mutation alleles. These alleles are genetically unstable. Individuals with FXS may have various combinations of symptoms such as ataxia, premature ovarian failure, learning disabilities, and other cognitive/behavioral conditions, including autism-like symptoms.

One unfortunate exception to the versatility of PCR is in the difficulty of amplifying long runs of highly GC-rich sequence, including Full Mutation alleles of the FMR1 5'UTR. Attempts to optimize FMR1 PCR have included modifications to conventional PCR assay conditions. See *Genome Res.* 6(7):633-8 (1996); *Nucleic Acids Res.* 25(19): 3957-8 (1997); *J. Mol. Diagn* 8:544-550 (2006); *Am. J. Med. Genet.* 51(4):527-34 (1994). Yet after more than 15 years of FMR1 PCR assay development, as recently as 2008 (*Genet. Med.* 10(10):714-9 (2008)) a published pilot screening study to detect Fragile X in newborns reported that "two methods of quantitative polymerase chain reaction (PCR) analysis . . . used in the in-house validation process to determine the FMR1 repeat number in females failed to produce reliable and reproducible results" (emphasis added), and, further, that "a second [PCR] failure from either the first or secondary isolation was highly suggestive of an abnormal FMR1 CGG repeat size." Thus, those knowledgeable in the art continue to regard reproducible PCR amplification of full mutation Fragile X alleles as an unsolved problem.

Detection of CGG triplet repeat regions containing more than about 100 repeats by PCR has been observed to become progressively fainter with increasing repeat number. *J. Mol. Diagn.* 7:605-12 (2005). This difficulty, combined with the heterogeneous nature of FXS symptoms, has contributed to the use of procedures such as Southern blotting in order to detect Full Mutation alleles. Id. Southern blotting is generally more time-consuming and costly, and much less amenable to high-throughput implementations, than PCR.

A recent publication by Tassone et al. (*J. Mol. Diagn.* 10:43-49 (2008); "Tassone 2008") describes an assay to test for the presence of longer CGG alleles without full length amplification of the allele. See also WO2008/011170. The method utilizes a chimeric PCR primer that hybridizes to sites within the expanded CGG region, such that the presence of a broad smear of PCR products represents a positive result for an expanded allele. Id. at 46.

The random hybridization strategy can result in non-specific amplification and lack of resolution. The base PCR conditions used in this paper have been widely tested in many different labs and it appears that the maximum number of CGG repeats that can be successfully amplified is about 350 CGG repeats. See, e.g., Saluto et al., *J. Mol. Diagn.* 7:605-612 (2005). Non-specific amplification is apparent in Tassone 2008. The smear on the agarose gel shown by Tassone 2008 as FIG. 1 appears to contain products longer than the expected maximum length of 350 repeat containing amplicons, and thus it may be that much of the smear does not represent CGG repeat specific products (see FIG. 1 of Tassone 2008; the smear in lane 5 appears to extend to the vicinity of the loading well). Tassone et al. indicate in the FIG. 3 legend that they used the High-Low ladder (Bionexus, Oakland, Calif.) as a molecular weight marker, and the marker in FIG. 1 appears to be the same as in FIG. 3. The largest band of the High-Low ladder is approximately 10 kb, and the smear in FIG. 1 extends above that band. This length is also longer than the expected full length product of the sample used in the assay. The longest allele size is listed as 615 CGG repeats. Therefore, the full length products are expected to be about 2 kb, estimated by adding about 200 nt of flanking sequence to 1845 nt of repeats. Non-specific products may reduce both the precision and confidence of amplification-based determinations regarding Fragile X associated allele status.

Additionally, some conventional PCR assays for detection of a Fragile X based on purely gene-specific primer designs have limitations. For example, such assays provide an estimate of the CGG repeat number based on the mobility of the PCR amplicon. To enable accurate repeat number quantification, amplicon mobility is generally measured relative to external calibrators, e.g., an appropriate set of size standards. It is desirable to enable accurate CGG quantification without relying on external calibrators.

Moreover, FMR1 alleles may contain AGG sequences that are interspersed among the CGG repeats, usually in the 5' region of the repeat segment. Knowledge of the AGG sequence elements characterizes the allele in one respect. AGG sequence elements may be used in clinical decision making. For example, cases of expansion of a mother's FMR1 allele to a full mutation allele in her child have been noted for an allele with as few as 59 repeats, and this allele is known to lack any AGG elements. See Nolin et al., *Am. J. Hum. Genet.* 72:454-464 (2003). Indeed, full mutations rarely if ever seem to contain AGG elements beyond the first 20 CGG repeats, and biophysical studies have suggested that templates with AGG "interruptor" sequences among the CGG repeat segment are more likely to adopt more conventional DNA structures and are more stable and more amenable to accurate replication. See, e.g., Weisman-Shomer et al., *Nucleic Acids Res.* 28:1535-41 (2000); Zhong et al., *Am. J. Med. Genet.* 64:261-5 (1996); Larsen et al., *Am. J. Med. Genet.* 93:99-106 (2000); and Dombrowski et al., *Hum. Mol. Genet.* 11:371-78 (2002). Thus, there is a need for a technology to map interruptor elements, such as AGG elements, within the FMR1 gene. Mapping of interruptor elements thus has research and diagnostic applications related to Fragile X Syndrome, and to other repeat-associated diseases as well.

Existing methods to map AGG elements include sequencing and restriction mapping. The technology of DNA sequencing is relatively laborious, particularly in that it generally requires enrichment or isolation (whether in vitro or in silico) of the sequence of interest, and is not routinely performed in Fragile X diagnostic testing. Restriction mapping based assays have used the enzyme MnlI, which recognizes the GAGG sequence and cuts 7 base pairs 5' to that sequence, to infer AGG positions based on the size of resulting fragments of digested PCR products that comprise the CGG-repeat region of the FMR1 5' UTR. See, e.g., Eichler et al., *Nat. Genet.* 8:88-94 (1994); Zhong et al., *Am. J. Hum. Genet.* 57:351-361 (1995). The assay of Eichler et al. involved PCR amplification of the repeat region, purification of the products, overnight digestion, electrophoresis for 7 hours, and Southern blotting. In the assay of Zhong et al., "the PCR product was extracted once with phenol/chloroform, ethanol precipitated, and partially digested in 10 liters with 5 units MnlI at 37° C. for 50-70 min." Id. at 353. This was followed by electrophoresis and Southern blotting. Both of these assays thus involved multiple steps including purification/cleanup, restriction digestion, and Southern blotting in addition to PCR and electrophoresis.

Provided herein are methods to quantify CGG repeats and to identify, quantify, and reveal the sequence context of interruptor sequences in the 5' UTR of FMR1 and FMR2 genes. The potential product applications of the invention include clinical applications for Fragile X testing.

In some embodiments, the invention relates to a method of analyzing at least one CGG-rich region comprised by at least one template in a sample, comprising:
  (a) providing at least two different primers, including a first primer comprising CGG, CCG, GCG, CGC, GCC, or GGC repeats, and a second primer that anneals to a position outside of the CGG-rich region;
  (b) performing PCR with the at least two different primers and the at least one template comprising the at least one CGG-rich region, wherein the PCR produces a set of products;
  (c) resolving the set of products with a high resolution technique to produce a representation of product size and abundance; and
  (d) deriving information about whether an interruptor sequence is present in the at least one CGG-rich region or where within the at least one CGG-rich region an interruptor sequence is located.

In some embodiments, the invention relates to a method of analyzing at least one CGG-rich region comprised by at least one template in a sample, comprising:
  (a) providing at least three different primers, including a first primer comprising CGG, CCG, GCG, CGC, GCC, or GGC repeats and a 5' flap, a second primer that anneals to a position outside of the CGG-rich region, and a third primer having a sequence comprised by the 5' flap of the first primer, wherein the first primer is provided at a lower concentration than the third primer;
  (b) performing PCR with the at least three different primers and the at least one template, wherein the PCR produces a set of products;
  (c) resolving the set of products with a high resolution technique to produce a representation of product size and abundance; and
  (d) deriving information about whether an interruptor sequence is present in the at least one CGG-rich region or where within the at least one CGG-rich region an interruptor sequence is located from said representation.

In some embodiments, the invention relates to a method of analyzing at least one CGG-rich region comprised by at least one template in a sample, comprising:
  (a) providing at least two different primers, wherein the first primer comprises CGG, CCG, GCG, CGC, GCC, or GGC repeats and the second primer anneals to a position outside of the CGG-rich region;
  (b) performing PCR with the at least two different primers and a template comprising the CGG-rich region, wherein the PCR produces a set of products;
  (c) resolving the set of products with a high resolution technique to produce a representation of product size and abundance; and
  (d) deriving information about CGG repeat number from said representation.

In some embodiments, the invention relates to a method of analyzing at least one CGG-rich region comprised by at least one template in a sample, comprising:
  (a) providing three different primers, wherein the first primer comprises CGG, CCG, GCG, CGC, GCC, or GGC repeats and a 5' flap, the second primer anneals to a position outside of the CGG-rich region, the third primer has the same sequence of the 5' flap of the first primer, and the first primer is provided at a lower concentration than the third primer;
  (b) performing PCR with the three different primers and a template comprising the CGG-rich region, wherein the PCR produces a set of products;
  (c) resolving the set of products with a high resolution technique to produce a representation of product size and abundance; and
  (d) deriving information about CGG repeat number from said representation.

In some embodiments, the invention relates to an oligonucleotide comprising a sequence chosen from SEQ ID NO:44 and SEQ ID NO:45.

It is to be understood that both the foregoing general description and the following detailed description are exemplary and explanatory only and are not restrictive of the invention, as claimed.

DETAILED DESCRIPTION

The invention relates to amplification reactions that amplify all or part of a CGG repeat region. In some embodiments, the CGG repeat region is comprised by the 5' UTR of FMR1, or the 5' UTR of FMR2.

The invention relates to amplification reactions that use a primer that anneals outside of a CGG repeat region and a primer that anneals to CGG repeat sequences, sequence permutations, or reverse complements of the sequences (GCG, CCG, CGC, GCC, or GGC). The primers that can anneal outside of (upstream or downstream) of the CGG repeat region may be forward or reverse primers. The primers may anneal to sequences flanking the CGG repeat region. Examples of such forward primers include CGG TGG AGG GCC GCC TCT GAG C (SEQ ID NO: 1), CAG GCG CTC AGC TCC GTT TCG GTT T (SEQ ID NO: 2), CAG TCA GGC GCT CAG CTC CGT TTC G (SEQ ID NO: 3), TCC GGT GGA GGG CCG CCT CTG AGC (SEQ ID NO: 4), GGT TCG GCC TCA GTC AGG CGC TCA GCT CCG TTT CG (SEQ ID NO: 5), GGG TTC GGC CTC AGT CAG GCG CTC AGC TCC GTT TCG (SEQ ID NO: 6), GCG GGC CGG GGG TTC GGC CTC AGT CA (SEQ ID NO: 7), CAG CGG GCC GGG GGT TCG GCC TCA G (SEQ ID NO: 8), GCA GCG GGC CGG GGG TTC GGC CTC A (SEQ ID NO: 9), GGG CCG GGG GTT CGG CCT CAG TCA G (SEQ ID NO: 10), GGG GTT CGG CCT CAG TCA GGC GCT CA (SEQ ID NO: 11), GGG GTT CGG CCT CAG TCA GGC GCT CAG (SEQ ID NO: 12), GGC GCT CAG CTC CGT TTC GGT TTC ACT TCC (SEQ ID NO: 13), TCA GGC GCT CAG CTC CGT TTC GGT TTC A (SEQ ID NO: 14), CAC TTC CGG TGG AGG GCC GCC TCT GA (SEQ ID NO: 15), TTC CGG TGG AGG GCC GCC TCT GAG C (SEQ ID NO: 16), and TCA GGC GCT CAG CTC CGT TTC GGT TTC ACG GCG GCG GCG GCG GA (SEQ ID NO: 44). Examples of such reverse primers include CGC ACT TCC ACC ACC AGC TCC TCC A (SEQ ID NO: 17), GGA GCC CGC CCC CGA GAG GTG (SEQ ID NO: 18), GGG AGC CCG CCC CCG AGA GGT (SEQ ID NO: 19), CGC ACT TCC ACC ACC AGC TCC TCC AT (SEQ ID NO: 20), CGG GAG CCC GCC CCC GAG AGG TG (SEQ ID NO: 21), CCG GGA GCC CGC CCC CGA GAG GT (SEQ ID NO: 22), CCG GGA GCC CGC CCC CGA GAG GTG (SEQ ID NO: 23), CGC CGG GAG CCC GCC CCC GAG AGG TG (SEQ ID NO: 24), GCG CCG GGA GCC CGC CCC CGA GAG GT (SEQ ID NO: 25), CGC CGG GAG CCC GCC CCC GAG AGG T (SEQ ID NO: 26), GCG CCA TTG GAG CCC CGC ACT TCC ACC A (SEQ ID NO: 27), GCG CCA TTG GAG CCC CGC ACT TCC A (SEQ ID NO: 28), AGC GCC ATT GGA GCC CCG CAC TTC C (SEQ ID NO: 29), CGC CAT TGG AGC CCC GCA CTT CCA C (SEQ ID NO: 30), TTG GAG CCC CGC ACT TCC ACC ACC A (SEQ ID NO: 31), AGC CCC GCA CTT CCA CCA CCA GCT CCT C (SEQ ID NO: 32), GAG CCC CGC ACT TCC ACC ACC AGC TCC T (SEQ ID NO: 33), CAT TGG AGC CCC GCA CTT CCA CCA CCA G (SEQ ID NO: 34), CCC GCA CTT CCA CCA CCA GCT CCT CCA TCT (SEQ ID NO: 35), TAG AAA GCG CCA TTG GAG CCC CGC ACT TCC (SEQ ID NO: 36), AAG CGC CAT TGG AGC CCC GCA CTT CC (SEQ ID NO: 37), AAG CGC CAT TGG AGC CCC GCA CTT CCC CGC CGC CGC CGC CG (SEQ ID NO: 43), and AAG CGC CAT TGG AGC CCC GCA CTT CCC CGC CGC CGC CGC CT (SEQ ID NO: 45).

The invention further relates to the use of and methods comprising providing the primers TCAGGCGCTCAGCTC-CGTTTCGGTTTCACTTCCGGT (SEQ ID NO: 38), AGCGTCTACTGTCTCGGCACTTGCCCGC-CGCCGCCG (SEQ ID NO: 39), TCA GGC GCT CAG CTC CGT TTC GGT TTC A (SEQ ID NO: 40), and TCAG-GCGCTCAGCTCCGTTTCGGTTTCA CGGCGGCG-GCGGCGG (SEQ ID NO: 41). The invention additionally relates to primers comprising the sequence of any of SEQ ID NOs 1-38 or 40 with repeats of CGG or the permutations and reverse complements thereof appended to the 3' end. The invention further relates to the use of and methods comprising providing a primer that contains a number of trinucleotide repeats of the sequence CGG or the permutations and reverse complements thereof. In some embodiments, the number of CGG repeats in the primer is four or five. In some embodiments, the primer contains 12-15 nucleotides of trinucleotide repeat sequence. In some embodiments, the primer contains a number of repeats ranging from 3 to 10. The primer may contain 3, 4, 5, 6, 7, 8, 9, or 10 repeats, and optionally an additional partial repeat of 1 or 2 C and/or G residues. Additional primers can be provided, for example, to ensure binding at a polymorphic site, or to amplify a region of known size in order to serve as an internal standard.

In some embodiments, the primer that anneals to CGG repeat sequences has a preferential binding activity for sites in the CGG-rich region comprising an interruptor element. Preferential binding of the primer that anneals to CGG repeat sequences to at least one site comprising an interruptor element can result in selective amplification of at least one product comprising the interruptor element, e.g., by using the primer in a PCR reaction with an oppositely oriented second primer that binds outside of the CGG-rich region, as described above. Preferential binding activity can be specific, for example, for sites comprising CGG and AGG elements, or the permutations and/or reverse complements thereof, such as a site comprising (1) one AGG element or a part of an AGG element comprising an A, and (2) three, four, five, or six CGG elements and optionally an additional partial CGG element.

The degree of preferential binding, expressed in terms of a ratio of the abundance of selectively amplified product to background products from an amplification reaction using the primer with an oppositely oriented second primer that binds outside of the CGG-rich region, can be at least 3-fold, 4-fold, 5-fold, or 6-fold, or can range from 3-fold to 12-fold, 3-fold to 10-fold, 3-fold to 8-fold, 4-fold to 12-fold, 4-fold to 10-fold, 4-fold to 8-fold, 3-fold to 7-fold, 4-fold to 7-fold, 3-fold to 6-fold, or 4-fold to 6-fold. The at least one selectively amplified product generally has a length corresponding to the distance along the template from the 5' end of the first primer, when preferentially bound to a site comprising an interruptor element, to the 5' end of the second primer, when bound to its site outside of the CGG-rich region.

In some embodiments, the primer that anneals to CGG repeat sequences and binds preferentially to a site or sites in the CGG-rich region comprising an interruptor element may comprise an A, T, or U residue within or at the end of the part of the primer that anneals to CGG repeat sequences, or in other words, among or at the end of the CGG, CCG, GCG, CGC, GCC, or GGC repeats; see, for example, SEQ ID NOs 44 and 45 above. The A, T, or U residue can occur at the 3' end of the primer. When the A, T, or U residue occurs at the end of the CGG, CCG, GCG, CGC, or GCC, GGC repeats, there may or may not be a partial CGG, CCG, GCG, CGC, GCC, or GGC repeat between the A, T, or U residue and the last complete CGG, CCG, GCG, CGC, GGC, or GGC repeat. It is possible to substitute unnatural nucleotide residues, discussed in more detail below, that preferentially base pair with T/U or A residues relative to other natural nucleotide residues for the A, T, or U residue. Likewise, it is also possible to substitute one or more unnatural nucleotide residues that preferentially base pair with C or G residues relative to other natural nucleotide residues for one or more G and/or C residues that make up the CGG, CCG, GCG, CGC, GCC, or GGC repeats. The presence of one or more such unnatural residues within a sequence otherwise made up of CGG, CCG, GCG, CGC, GCC, or GGC repeats (optionally with an A, T, U, or corresponding unnatural residue as discussed above) does not negate the identity of said sequence within the context of the present disclosure as a sequence of CGG, CCG, GCG, CGC, GCC, or GGC repeats.

In a non-anchored assay, a first primer is provided that has a preferential binding activity for sites in the CGG rich region that do not comprise interruptor elements. The presence of an interruptor element can be signaled in the results of a non-anchored assay by a relatively low level of products whose synthesis involved extension of the first primer bound to sites comprising the interruptor element. These low levels can appear as a gap or set of low peaks surrounded by higher peaks in an electropherogram.

In an anchored assay, a first primer is provided that has a preferential binding activity for sites in the CGG rich region that comprise interruptor elements. It should be noted that a primer having a preferential binding activity for sites in the CGG rich region that comprise interruptor elements can be provided in reactions in which at least one template comprises at least one CGG-rich region comprising zero, one, or a plurality of interruptor elements, and recitation of a primer with "a preferential binding activity for sites in the CGG rich region that comprise interruptor elements" does not imply, for example, that the CGG-rich region necessarily comprises a plurality of interruptor elements. The presence of an interruptor element is signaled in an anchored assay by a relatively high level of products whose synthesis involved extension of the first primer bound to sites comprising the interruptor element. The high level can appear as a spike surrounded by lower peaks and/or baseline signal in an electropherogram.

In some embodiments, the first primer used in an anchored assay comprises an A, T, or U residue among or at the 3' end of the CGG repeats. In some embodiments, the first primer used in an anchored assay comprises an unnatural nucleotide residue that preferentially base pairs with A or T/U residues relative to other natural nucleotide residues. Unnatural nucleotide residues are nucleotide residues comprising a nucleobase other than adenine, thymine, guanine, cytosine, and uracil (A, T, G, C, and U, respectively). Examples of unnatural nucleotide residues that preferentially base pair with A or T/U residues include, without limitation, adducts of T, U, or A residues that preferentially base pair with A or T/U residues relative to other natural residues (e.g., 5-substituted uracil analogs); and residues comprising nucleobases such as, for example, pseudouracil and diaminopurine.

Two primers are considered oppositely oriented when they bind opposite strands of a double-stranded nucleic acid template.

As used herein, a sequence is "upstream" of a CGG-rich region when it occurs 5' of the CGG-rich region along the strand comprising CGG repeats. As used herein, a sequence is "downstream" of a CGG-rich region when it occurs 3' of the CGG-rich region along the strand comprising CGG repeats.

The methods of the invention may relate to amplification reactions comprising providing at least two or at least three different primers. In some embodiments, at least three different primers are provided and one of the primers is a subsequence of another primer. In some embodiments, one primer is a chimeric primer comprising CGG repeats and a 5' flap sequence, and another primer has the sequence of the 5' flap sequence of the chimeric primer. It should be noted that the primer having the sequence of the 5' flap sequence of the chimeric primer can, but does not necessarily, have the entire non-repeat sequence of the chimeric primer. In other words, the sequence of part or all of one primer can be comprised by the sequence of another primer; for example, the chimeric primer comprises a 5' flap sequence, and another primer can comprise the sequence of part or all of the 5' flap. In some embodiments, the primer contains 12-15 nucleotides of CGG repeat sequence. The 5' flap sequence may correspond to a sequence adjacent to or near to the CGG repeat region, or it may be unrelated to sequences in and around the CGG repeat region. In some embodiments, the length of the chimeric primer may be approximately 35, 40, 45, 50, or 55 nt. In some embodiments, one or more of the primers has a Tm ranging from 60° C. to 75° C., for example, approximately 60° C., 65° C., 70° C., or 75° C.

In some embodiments, at least three different primers are provided and one primer is provided at a concentration lower than the concentration of another primer. For example, the chimeric primer is optionally provided at a lower concentration than the primer with the sequence of the 5' flap sequence of the chimeric primer. The ratio of concentrations, expressed as a fold difference, may range from 2 to 10,000 or more, for example, 10, 20, 50, 100, 200, 500, 1,000, 2,000, 5,000, or 10,000. In such embodiments, the primer present at a lower concentration can be depleted in early rounds of the amplification reaction, such that extension is generally all, or nearly all, from the primers still present (which were initially present at relatively higher concentrations).

The invention relates to reactions that amplify nucleic acids. Examples of amplification reactions include, without limitation, PCR, NASBA (nucleic acid sequence based amplification), and SDA (strand displacement amplification). See, e.g., U.S. Pat. No. 4,683,202 (PCR); U.S. Pat. No. 6,326,173; and *J. of Virol. Methods* 151:283-293 (2008) (NASBA); and U.S. Pat. No. 5,648,211 (SDA). All of the foregoing are incorporated herein by reference. The skilled artisan will understand what reagents are appropriate to provide. Each of these methods involves DNA synthesis, and as such involves the use of DNA polymerases, nucleotides, and divalent cations (supplied as a salt), particularly magnesium, in a solution conducive to DNA polymerization and in which the template is present. The methods vary in terms of providing additional catalytic activities, the use of thermocycling or isothermal incubation, and the use and structure of primers. A buffer at a suitable pH such as between 7 and 8, between 6.5 and 8.5, between 6 and 9, or about 7.4 or 7.5 is also typically provided.

In PCR according to the invention, at least a pair of primers is provided that binds at each end of or within a target region, on opposite strands, such that they each prime synthesis toward the other primer. The reaction is thermocycled so as to drive denaturation of the substrate in a high temperature step, annealing of the primers at a lower temperature step, and extension at a temperature which may be but is not necessarily higher than that of the annealing step. Amplification occurs because the products of one cycle can serve as templates in the next cycle.

In NASBA, an RNA polymerase (RNAP) is provided in addition to the DNA polymerase, which may also be a reverse transcriptase (RT) (e.g., an enzyme that can catalyze DNA synthesis using either an RNA or DNA template). Primers are provided that are similar to those used in PCR except that at least one primer additionally comprises a promoter sequence that is recognized by the RNAP. Thus, the product of the RT serves as a template for the RNAP, which synthesizes RNA that serves as a template for the RT, leading to amplification. In some forms of NASBA, RNase H is provided to produce single-stranded DNA after synthesis of an RNA-DNA hybrid by RT. Amplification occurs via the combined action of the RT and RNAP, in the absence of repeated thermal denaturation.

SDA is a technique in which DNA is amplified in an isothermal and asynchronous manner, meaning that cyclic thermal denaturation is not used to separate the strands; instead, strand displacement occurs through DNA synthesis itself, wherein extension of a 3' OH causes displacement of the downstream strand. The 3' OH is provided initially by an exterior primer and subsequently by a nicking reaction. Two pairs of primers are provided. One 'interior' pair binds surrounding the amplicon and additionally comprises 5' flaps containing a restriction site. The other 'exterior' pair is positioned distally, i.e., further from the target region. An interior primer may bind the template, be extended, and then be displaced by synthesis from the corresponding exterior primer. Subsequently, the displaced DNA is made double-stranded, e.g., by second strand synthesis. The next step is to nick one strand of the double stranded molecule, which may be done by using modified nucleotides and a restriction site wherein the cleavage site is inactivated on one strand (but not the other) by the modified nucleotide. The restriction enzyme corresponding to this site is provided in the reaction and generates the nick. The 3' OH at the resulting nick is then extended by the DNA polymerase, displacing one strand (which may again serve as a template[1]) and the regenerated double strand molecule is again a substrate for nicking followed by extension and displacement, leading to amplification. Repeated thermal denaturation is not necessary.

[1] Note that some displaced strands will not initially be full-length but will lack the complement of the distal portion of the interior primer flap, as a consequence of the nicking. This does not impair primer binding (recall that the non-flap portion of the primer has sufficient length to anneal stably) and, upon primer binding, a 5' overhang is generated that the polymerase is able to fill in.

In some embodiments, the methods of the invention comprise providing dNTPs in a GC/AT Ratio greater than one, and at a total dNTP concentration conducive to synthesis of DNA using GC-rich templates. See U.S. application Ser. No. 12/371,306. The GC/AT ratio may be about 1.1, 1.2, 1.4, 1.6, 2, 2.5, 3, 4, 5, 6, 7, 8, 9, 10, 11, 12, 13, 14, 15, 16, 17, 18, 19, 20, 25, or higher. The GC/AT ratio may be between 1.1 and 20, 1.1 and 15, 1.1 and 10, 1.1 and 8, 1 and 15, 1.1 and 7, 1.1 and 6, 1.1 and 5, 1.2 and 25, 1.4 and 25, 1.6 and 25, 2 and 25, 3 and 25, 4 and 25, 5 and 25, 2 and 15, 2.5 and 10, or 4 and 10. The total dNTP concentration may be about 0.4, 0.5, 0.6, 0.7, 0.8, 0.9, 1, 1.2, 1.5, 2, or 3 mM. The dNTP concentration may be between 0.4 and 3 mM, 0.5 and 3 mM, 0.6 and 3 mM, 0.7 and 3 mM, 0.8 and 3 mM, 0.9 and 3 mM, 1 and 3 mM, 0.4 and 2 mM, 0.4 and 1.5 mM, 0.4 and 1.2 mM, 0.4 and 1 mM, 0.4 and 0.9 mM, 0.4 and 0.8 mM, 0.4 and 0.7 mM, 0.5 and 2 mM, 0.5 and 1 mM, or 0.6 and 0.9 mM. "GC/AT Ratio" means the ratio of the concentration of the sum of dCTP, dGTP, and all nucleotide analogs thereof, to the concentration of the sum of dATP, dTTP, dUTP, and all nucleotide analogs thereof, in a given solution or mixture. "dNTP" stands for deoxynucleotide triphosphate and refers to dATP, dCTP, dGTP, dTTP, dUTP, and analogs thereof. "Nucleotide analogs" are molecules or ions comprising a base moiety other than the natural bases adenine (A), cytosine (C), guanine (G), thymine (T), or uracil (U), a sugar moiety identical or similar to deoxyribose, and at least one phosphate or multiple phosphate (e.g., diphosphate or triphosphate) moiety. The nucleotide analog is an analog of a specific nucleotide, in particular dATP, dCTP, dGTP, dTTP, or dUTP, when it comprises a triphosphate and a sugar moiety, the structure and configuration of both of which are suitable for incorporation into a nucleic acid double helix by a polymerase, and a base whose base pairing properties in a nucleic acid double helix and loci of incorporation by DNA polymerases in a nucleic acid double helix are most similar to one of the five previously listed nucleotides, with the exception that analogs of dTTP will generally also be analogs of dUTP and vice versa. The term "analog" used in conjunction with terms including but not limited to "nucleoside", "base", "nucleobase", or "residue" is to be interpreted in the same manner as if it were used in conjunction with "nucleotide."

In some embodiments, enhancers may be provided. The enhancers contribute to the success of reactions generating GC-rich product. A variety of enhancers may be included in PCR reactions in general to increase yield, specificity, and consistency, and may operate by lowering the Tm of template DNA. Enhancers may function through helix destabilization, neutralization of reaction inhibitors, or other mechanisms, including unknown mechanisms. Enhancers include, without limitation, betaine, betaine analogs, glycerol, bovine serum albumin (BSA), polyethylene glycol, tetramethylammonium chloride, 7-deaza-GTP, neutral detergents, dimethylsulfoxide (DMSO), methanol, ethanol, isopropanol, formamide, acetone, acetamide, N-methylformamide, N,N-dimethylformamide, acetone, acetimide, N-methylacetimide; N,N-dimethylacetimide, 2-pyrrolidone, N-methylpyrrolidone, propionamide, and isobutyramide. Neutral detergents include, without limitation, TWEEN-20, β-octyl-glucoside, Octyl-β-Thio-glucopyranoside, Triton X-100, Triton X-114, NP-40, Brij-35, Brij-58, Tween-80, Pluronic F-68, Pluronic F-127, Deoxy Big CHAP, CHAPS, CHES, nonyl phenoxylpolyethoxylethanol (Tergitol-type NP-40), and octyl phenoxylpolyethoxylethanol (Igepal CA-630). Betaine analogs include, without limitation, homodeanol betaine, deanol betaine, propio betaine, homoglycerol betaine, diethanol homobetaine, triethanol homobetaine, hydroxypropyl homobetaine, N-Methyl-N-(2-carboxyethyl)morpholinium inner salt, N-Methyl-N-(2-carboxyethyl)piperidinium inner salt, N-Methyl-N-(2-carboxyethyl)pyrrolidinium inner salt, N,N-dimethyl-N-(2-hydroxyethyl)-N-(2-sulfoethyl)ammonium inner salt, N,N-dimethyl-N-(2-hydroxyethyl)-N-(3-sulfopropyl)ammonium inner salt, N,N-dihydroxyethyl-N-methyl-N-(3-sulfopropyl)ammonium inner salt, N,N-dimethyl-N-(2-hydroxyethyl)-N-(4-sulfobutyl)ammonium inner salt, N-methyl-N-(3-sulfopropyl)morpholinium inner salt, and N-methyl-N-(3-sulfopropyl)piperidium inner salt.

Betaine, betaine analogs and/or other enhancers may be provided at molar concentrations between 0.01 and 5 M, 0.01 and 4 M, 0.01 and 3 M, 0.01 and 2.5 M, 0.02 and 5 M, 0.03 and 5 M, 0.04 and 5 M, 0.05 and 5 M, 0.07 and 5 M, 0.1 and 5 M, 0.2 and 5 M, 0.3 and 5 M, 0.4 and 5 M, 0.5 and 5 M, 0.7 and 5 M, 1 and 5 M, 1.5 and 5 M, 0.1 and 4 M, 0.5 and 3 M, 1 and 2.5 M, or 1.5 and 2.5 M, for example, about 0.01, 0.02, 0.05, 0.1, 0.2, 0.5, 0.75, 1, 1.25, 1.5, 1.6, 1.7, 1.8, 1.9, 2.0, 2.1, 2.2, 2.3, 2.4, 2.5, 3, 3.5, 4, 4.5, or 5 M. Alternatively, enhancers may be provided at w/v or v/v percentage concentrations of between 0.1 and 50%, 0.2 and 50%, 0.5 and 50%, 1 and 50%, 2 and 50%, 5 and 50%, 0.1 and 40%, 0.1 and 30%, 0.1 and 20%, 0.5 and 40%, 1 and 30%, or 2 and 20%, for example, about 0.1, 0.2, 0.5, 1, 2, 5, 10, 15, 20, 25, 30, 35, 40, 45, or 50% by volume. Neutral detergents may be provided at between 0.0001 and 10% by volume, 0.0002 and 10%, 0.0005 and 10%, 0.001 and 10%, 0.002 and 10%, 0.005 and 10%, 0.01 and 10%, 0.02 and 10%, 0.05 and 10%, 0.0001 and 5%, 0.0001 and 2%, 0.0001 and 1%, 0.0005 and 1%, or 0.001 and 1%, for example, about 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10% by volume. Those skilled in the art will recognize appropriate concentrations for various enhancers.

The invention relates to methods comprising providing buffers for amplification reactions. The buffers may comprise, for example and without limitation, tris(hydroxymethyl)aminomethane (Tris), bis-tris propane, bicarbonate, phosphate, glycine, histidine, 4-(2-hydroxyethyl)-1-piperazineethanesulfonic acid (HEPES), 3-(N-morpholino)propanesulfonic acid (MOPS), and various conjugate bases/acids and salts thereof.

The invention relates to methods comprising providing at least one DNA polymerase to synthesize DNA from dNTPs in a template dependent manner. The DNA polymerase may comprise a wild-type, modified, thermophilic, chimeric, engineered, and/or a mixture of more than one polymerase. The DNA polymerase may comprise Exact Polymerase (5 PRIME GmbH), AccuSure™ DNA Polymerase (Bioline), Phusion™ AccuPrime™ Pfx (Invitrogen), Platinum Taq DNA Polymerase High Fidelity (Invitrogen), Phire™ Hot Start DNA Polymerase (New England Biolabs), Phusion® Hot Start High-Fidelity DNA Polymerase (New England Biolabs), JumpStart™ REDTaq™ DNA Polymerase (Sigma-Aldrich), PfuUltra™ Hotstart DNA Polymerase (Stratagene), PfuTurbo® Cx Hotstart DNA Polymerase (Stratagene), PrimeSTAR™ HS DNA Polymerase (Takara), Extensor Hi-Fidelity PCR Enzyme (ABgene), ACCUZYME™ DNA Polymerase (Bioline), SAHARA™ DNA Polymerase (Bioline), VELOCITY DNA Polymerase (Bioline), GeneChoice® AccuPOL™ DNA Polymerase (GeneChoice, Inc.), GeneChoice® UniPOL™ DNA Polymerase (GeneChoice, Inc.), Elongase Enzyme Mix (Invitrogen), Pfx50™ DNA Polymerase (Invitrogen), Phusion DNA Polymerase (New England Biolabs), KOD HiFi DNA Polymerase (Novagen), KOD XL DNA Polymerase (Novagen), Expand 20 kb PLUS Thermostable DNA polymerase mixture (Roche Applied Science), Expand High Fidelity PLUS Thermostable DNA polymerase mixture (Roche Applied Science), Expand High Fidelity Thermostable DNA polymerase mixture (Roche Applied Science), Expand Long Template Thermostable DNA polymerase mixture (Roche Applied Science), Easy-ATM High-Fidelity PCR Cloning Enzyme (Stratagene), EXL™ DNA Polymerase (Stratagene), Herculase® Enhanced DNA Polymerase (Stratagene), Herculase® II Fusion DNA Polymerase (Stratagene), Kapa LongRange™ DNA Polymerase (Kapa Biosystems), Kapa HiFi™ DNA Polymerase (Kapa Biosystems), Kapa2G™ Robust DNA Polymerase (Kapa Biosystems), Kapa2G™ Robust HotStart DNA Polymerase (Kapa Biosystems), Kapa2G™ Fast DNA Polymerase (Kapa Biosystems), Kapa2G™ Fast HotStart DNA Polymerase (Kapa Biosystems), LA TAQ DNA Polymerase (Takara), Optimase DNA Polymerase (Transgenomic, Inc.), Exo-Pfu DNA Polymerase (Stratagene), HotMaster Taq DNA Polymerase (5 PRIME GmbH), HotTaq DNA Polymerase (Abnova Corporation), AmpliTaq Gold® DNA Polymerase (Applied Biosystems), Bst DNA Polymerase Lg Frag (New England Biolabs), MasterAmp™ Tfl DNA Polymerase (EPICENTRE Biotechnologies), Red Hot DNA Polymerase (ABgene), Thermoprime Plus DNA Polymerase (ABgene), Taq-red DNA Polymerase (AppliChem GmbH), BIO-X-ACT™ Long DNA Polymerase (Bioline), BIO-X-ACT™ Short DNA Polymerase (Bioline), Bioline HybriPol™ DNA Polymerase (Bioline), BioTherm Taq DNA Polymerase (eEnzyme LLC), EU-Taq DNA Polymerase (eEnzyme LLC), Synergy Taq DNA Polymerase (eEnzyme LLC), GeneChoice® RedPOL™ DNA Polymerase (GeneChoice, Inc.), AccuPrime™ GC-Rich DNA Polymerase (Invitrogen), PyroPhage® 3173 DNA Polymerase, Exo Minus (Lucigen), 9 Degrees North (Modified) DNA Polymerase (New England Biolabs), Therminator DNA Polymerase (New England Biolabs), Pwo DNA Polymerase (Roche Applied Science), Pag5000™ DNA Polymerase (Stratagene), YieldAce™ DNA Polymerase (Stratagene), e2TAKT™ DNA Polymerase (Takara), or naturally occurring DNA polymerases from *P. kodakaraensis, P. furiosus, T. gorgonarius, T. zilligii, T. litoralis* "Vent™", P. GB-D "Deep Vent", *T.* 9N-7, *T. aggregans, T. barossii, T. fumicolans, T. celer, Pyrococcus* sp. strain ST700, *T. pacificus, P. abysil, T. profundus, T. siculi, T. hydrothermalis, Thermococcus* sp. strain GE8, *T. thioreducens, P. horikoshii* or *T. onnurineus* NA1, *Thermococcus* sp. 9° N-7, *Thermococcus* sp. GI-J, *Thermococcus* sp. MAR-13, *Thermococcus* sp. GB-C, *Thermococcus* sp. GI-H, *Thermus aquaticus, Thermus thermophilus, Thermus caldophilus, Thermus filiformis, Thermus flavus, Thermotoga maritima, Bacillus stearothermophilus,* or *Bacillus caldotenax.*

The data obtained through the invention, e.g., the results of the tests, may be used in the process of diagnosing the presence or absence of a condition or disease. The data obtained through use of the invention may be used in determination of the genotype of an individual. The data obtained through the invention may be used to detect genotypes associated with Fragile X Syndrome, Fragile X-associated tremor ataxia syndrome, and Fragile X-associated primary ovarian insufficiency. Genetic loci associated with these conditions are known in the art and include without limitation FMR1, FMR2, the 5' UTR of FMR1, the 5' UTR of FMR2, the CGG repeats within the 5' UTR of FMR1, and the CGG repeats within the 5' UTR of FMR2. In an additional embodiment, the data obtained through the invention may be used to detect genotypes associated with GC-rich trinucleotide repeat disorders and/or with interruptor elements, such as Fragile X Syndrome, Fragile X-associated tremor ataxia syndrome, and Fragile X-associated primary ovarian insufficiency, myotonic dystrophy, Huntington's disease, spinobulbar muscular atrophy, Dentatorubropallidoluysian atrophy, and/or spinocerebellar ataxia. An interruptor element, as the name suggests, interrupts a series of repeats. A CGG-rich region may or may not comprise interruptor element(s). Thus, a CGG-rich region can comprise series of trinucleotide repeats and at least one interruptor element between the series. Genetic loci associated with these conditions are known in the art and include without limitation FMR1, FMR2, DMPK, ZNF9, HTT, AR, ATN1, ATXN1-3, ATXN7, ATXN10, CACNA1A, SCAB, PPP2R2B, and TBP. See, e.g., *Nat. Genet.* 13(1):105-8 (1996); *Nat. Genet.* 13(1):109-13 (1996).

The methods can comprise determining the presence or absence of interruptor elements near either end of a CGG-rich region comprised by at least one allele comprised by the sample, for example, within 60, 90, 120, 150, 180, 210, 240, 270, or 300 by of either end. Determining the presence or absence of interruptor elements within a given distance of either end of a CGG-rich region comprised by at least one allele comprised by the sample is understood to include determining interruptor presence or absence throughout CGG-rich regions with sizes such that the entire CGG-rich region is within the given distance of either end.

In some embodiments, the methods comprise analyzing at least one CGG-rich region independently of auxiliary or reflex assays comprising procedures such as Southern blotting, restriction digestion, or sequencing, for example, Sanger sequencing, Maxam-Gilbert sequencing, ligation sequencing, and single molecule sequencing-by-synthesis (also known as second-generation sequencing), which includes reversible terminator sequencing and pyrosequencing. The methods nonetheless can comprise determination of information about at least one CGG-rich region such as length and/or interruptor element content or position as described herein. In some embodiments, the methods comprise deriving information that is necessary and sufficient for determination of information about at least one CGG-rich region such as length and/or interruptor element content or position as described herein from the representation of product size and abundance produced by a high resolution technique from an amplification reaction as described herein.

Information about whether an interruptor sequence is present in the at least one CGG-rich region or where within the at least one CGG-rich region an interruptor sequence is located can comprise information such as whether at least one CGG-rich region comprised by at least one template in a sample comprises an interruptor sequence; in cases where more than one different template is present, whether each template in a sample comprises an interruptor sequence; a lower bound estimate of the number of interruptor sequences present in the at least one CGG-rich region; and/or at least one position of at least one interruptor element (including determination to within a given level of accuracy, as discussed below). The preceding listing of specific types of information does not include other types of information that can be determined through the methods of the invention disclosed explicitly or implicitly herein, in view of the knowledge of one of ordinary skill in the art.

In some embodiments, the methods comprise performing at least two assays, wherein each assay comprises (a) providing primers, wherein the primers of the at least two assays are non-identical; (b) performing an amplification reaction to produce a set of products; (c) resolving the set of products, at least two representations of product size and abundance being produced from the at least two assays; and (d) deriving information about whether an interruptor sequence is present in the at least one CGG-rich region or where within the at least one CGG-rich region an interruptor sequence is located. In some embodiments, the information derived comprises information that could not have been derived if only one assay had been performed, such as, in cases where the sample comprises at least two different templates comprising CGG-rich regions and at least one interruptor element is present in at least one of the CGG-rich regions, which of the at least two CGG-rich regions comprises the at least one interruptor element. For example, a situation in which this information can be ambiguous from the results of one assay is illustrated in FIG. 10. Other possible ambiguities, and examples of how to resolve them, are discussed below.

In some embodiments, the at least two assays comprise an anchored assay and a non-anchored assay. In some embodiments, the at least two assays use oppositely oriented primers comprising CGG, CCG, GCG, CGC, GCC, or GGC repeats. That is, a first assay can comprise providing primers comprising a primer comprising repeats that is oriented upstream, and the second assay can comprise providing primers comprising a primer comprising repeats that is oriented downstream, or vice versa.

In some embodiments, the methods comprise at least three assays, comprising at least two non-anchored assays and at least one anchored assay, or vice versa. The at least two non-anchored (or anchored) assays can use oppositely oriented primers comprising CGG, CCG, GCG, CGC, GCC, or GGC repeats, as discussed in the previous paragraph.

It should be noted that in some situations, a "set of products" may not comprise a plurality of major or detectable products, such as in anchored assays with samples comprising at most one CGG-rich region that comprises at most one interruptor. Primers are considered "non-identical" between assays if at least one of the primers used in one of the assays differs from the primers used in the other assays; in other words, some of the primers can be identical.

The methods can comprise determining at least one detail of a heterozygous, aneuploid, or mosaic genotype, by performing at least two assays as described above, wherein the amplification reactions use non-identical primer sets, and the at least one detail is determined by comparing results of the at least two amplification reactions.

The genotype of a sample refers to the genotype of the source from which a sample was obtained; this term may encompass multiple individual genotypes in the case of mixed samples.

A sample having a heterozygous genotype comprises genetic material from a cell comprising two alleles of the locus comprising the CGG-rich region.

A sample having a mosaic genotype comprises at least two alleles of the locus comprising the CGG-rich region, with the cells from which the sample was obtained being genetically different in at least one allele of the locus comprising the CGG-rich region. The at least two alleles comprised by a sample having a mosaic genotype can be categorized as major or minor alleles depending on their abundance. The allele with the greatest abundance is considered a major allele and the allele with the smallest abundance is considered a minor allele; when more than two alleles are present, alleles are classified as major or minor based on whether their relative abundance, expressed as a percentage, is arithmetically closer to the allele with the highest or lowest abundance. For example, in a sample comprising first, second, and third alleles with relative abundances of 60%, 31%, and 9%, respectively, the second allele is considered a minor allele. The presence of major and minor alleles can also result from aneuploidy, for example, if a genome comprises three copies of a CGG-rich region, of which two are the same (the major allele) and one is different (the minor allele). Aneuploidy is discussed in detail below.

In some embodiments, the methods comprise detecting whether a sample comprises a minor allele with a relative abundance of at least 5%, 6%, 7%, 8%, 9%, 10%, 15%, 20%, or 25%. It is understood that the CGG-rich region of the minor allele would be different from the CGG-rich region of the major allele. For example, the minor allele could have a CGG-rich region with a different number of repeats and/or a different distribution of AGG elements. In some embodiments, the methods comprise detecting whether a sample comprises a minor allele that comprises an interruptor element. In some embodiments, the methods comprise detecting the location of an interruptor element in a minor allele, which may be within a level of precision as discussed below.

A sample having an aneuploid genotype comprises a number of alleles of the locus comprising the CGG-rich region other than the euploid number. The euploid number is one for somatic chromosome loci in gametes and germline cells having undergone a reductive meiotic division, except for sex chromosome loci in male gametes and male germline cells having undergone a reductive meiotic division, where it may be 0 or 1 for individual cells and averages to about 0.5 for a population thereof (subject to variation depending on the number of X- and Y-chromosome bearing cells present). The euploid number is also one for X-chromosome loci in male somatic cells and male germline cells having not yet undergone a reductive meiotic division. The euploid number is 2 for loci on somatic chromosomes in somatic cells and in germline cells having not yet undergone a reductive meiotic division, and for X-chromosome loci in female somatic cell and female germline cells having not yet undergone a reductive meiotic division. It is possible for a sample to have more than one of the conditions of heterozygosity, aneuploidy, and mosaicity.

Mosaic genotypes can occur, for example, in samples from individuals comprising cells derived from different progenitor cells (zygotes, blastomeres, stem cells, etc.), or individuals comprising cells which are genetically different due to somatic mutation, including alteration of repeat number, such as repeat expansion. Aneuploidy is present in certain syndromes, for example Down's, Turner's, and Klinefelter's, and can also arise somatically via chromosomal nondisjunction events; such events can result in individuals who can provide mosaic aneuploid samples, which may or may not also be heterozygous.

Samples which comprise at least two different alleles of the locus comprising the CGG-rich region (due to being at least one of heterozygous, aneuploid, or mosaic for that locus) can be analyzed to determine at least one detail regarding the genotype.

The at least one detail can comprise whether one, two, neither, or more than two (if applicable) of the at least two different alleles comprise at least one interruptor element.

The at least one detail can comprise the minimum number of interruptor elements comprised by at least one of the at least two different alleles. For example, it could be determined that one allele comprises at least one interruptor element. The at least one detail could further comprise that another allele comprises, e.g., at least two interruptor elements.

The at least one detail can comprise the location of at least one interruptor element in one of the alleles.

In some embodiments, the at least one detail comprises at least one detail that cannot be determined unambiguously about the genotype of a heterozygous, aneuploid, and/or mosaic sample from the results of a single assay. The following is a non-exclusive list of details that can be ambiguous from the results of a single assay:

1. The results of a single assay may indicate that at least one interruptor element is present, but said results may be ambiguous as to which allele comprises the at least one interruptor element.
2. The results of a single assay may indicate that at least two interruptor elements are present, but said results may be ambiguous as to whether the interruptor elements are comprised by the same allele or different alleles.
3. The results of a single assay may indicate that at least three interruptor elements are present, but said results may be ambiguous as to how the at least three interruptor elements are distributed among the at least two different alleles.
4. The results of a single assay may be ambiguous as to whether an interruptor element is present at a position in a first allele that is obscured in the representation of product size and abundance by signal, such as a large peak, corresponding to a second allele.

In some embodiments, the methods of the invention result in the synthesis of products that do not contain, or are free of, a substantial fraction of nonspecifically amplified material. In some embodiments, the methods result in the synthesis of products that do not contain, or are free of, a substantial fraction of nonspecifically amplified material when the template is one of the samples described in Examples 1-3 below. In some embodiments, the methods of the invention result in the synthesis of products that do not contain, or are free of, a substantial fraction of nonspecifically amplified material that is larger than an expected size, said expected size being calculated by adding the length of the CGG rich region to an adjustment based on the position at which the second primer anneals. In some embodiments, the products contain less than 20%, 15%, 10%, 5%, 2%, or 1% of material that is larger than the expected size described in the preceding sentence, as determined by densitometry or integration of signal from a representation of product size and amount. In some embodiments, this representation is an electropherogram. As defined herein, the products are "substantially free" of nonspecifically amplified material when they contain less than about 10% of material that is larger than the expected size, as determined above.

The invention relates to methods comprising analyzing a template comprising GC-rich repeat sequences, such as, for example, CGG or CCG trinucleotides. Said analyzing can comprise performing an amplification reaction and resolving the products at high resolution. The high resolution may be a resolution sufficient to distinguish products containing, for example, 20 versus 21, or 20 versus 22, 20 versus 23, 20 versus 24, or 20 versus 25 trinucleotide repeats, or in some embodiments, products differing in length by 1, 2, 3, 4, 5, 6, 7, 8, 9, 10, 11, 12, 13, 14, 15, 16, 17, or 18 nucleotides or base pairs. Examples of techniques that may be employed in the methods of the invention to accomplish this resolving step include, without limitation, capillary electrophoresis, and polyacrylamide gel electrophoresis (PAGE; some embodiments of PAGE being commonly referred to in the art as "running a sequencing gel"), or "lab-on-a-chip" type microfluidics/electrophoresis systems. Instrumentation for performing capillary electrophoresis may be obtained from, for example, vendors such as Applied Biosystems (ABI), Beckman, Agilent, and Qiagen, and suitable instruments include without limitation ABI 310, 3100, 3130/3130xl, or 3730/3730xl; Beckman P/ACE MDQ; Agilent 2100 Bioanalyzer; and Qiagen QIAxcel. The process of resolving the products electrophoretically can involve the use of liquid polymers, including, for example, POP-7, POP-6, POP-5, or POP-4, all of which are sold by Applied Biosystems. In some embodiments, a polymer that can resolve products containing approximately 250, 300, 350, 400 or more trinucleotide repeats precisely according to size, such as, for example, POP-4, is used in resolving the products. Resolving the set of products at high resolution can be accomplished using a machine, for example, chosen from machines that comprise a source of voltage (e.g., a DC power supply), machines that comprise a source of pressure (e.g., a pump), and machines that comprise a column or capillary suitable for performing chemical separations. The machine can of course comprise more than one of the foregoing components.

Resolving the products at high resolution leads to the production of a representation of product size and abundance. This representation may be an image or graph that one of skill in the art can interpret, visually or with the aid of instrumentation such as, for example, a computer with appropriate software or a densitometer, to understand the size(s) and amount(s) of the products of the reaction. In some embodiments, the representation is an electropherogram, photograph, graph, plot, or autoradiogram. The representation may be derived or recorded from photons or beta particles emitted by the products or dye molecules bound to the products; these may be detected, for example, photographically or electronically, and processed or developed to generate the representation.

The invention relates to methods comprising deriving information about CGG repeat number (i.e., how many CGG repeats, or trinucleotide repeats generally, are comprised by the template) from the representation of product size and abundance. Such derivation may comprise counting the number of species observable in the representation to determine the repeat number (starting from the number of repeats comprised by the smallest product, which may, for example, be 4 or 5), or estimating the repeat number based on the position of the largest product observable in the representation.

In some embodiments, the CGG-rich region is comprised by the 5' UTR of FMR1 or the 5' UTR of FMR2.

In some embodiments, the methods comprise detecting whether interruptor elements are present within the CGG-rich region. In some embodiments, the interruptor elements are AGG trinucleotides. Detecting whether these are present may be achieved, for example, by determining positions in the template where binding of the first primer was substantially reduced, or by determining a set of lengths at which the amount of product is substantially reduced compared to neighboring lengths. For example, if the $10^{th}$ trinucleotide were AGG in a region with at least 14 total trinucleotide repeats and an amplification reaction were performed involving use of a primer comprising 4 CGG repeats, the products with 10, 11, 12, and 13 CGG repeats would be expected to be present in a substantially reduced amount relative to the neighboring products with 9 and 14 repeats. The degree to which the amount is reduced can range from 25% to 95% or more, for example, 25%, 30%, 35%, 40%, 45%, 50%, 55%, 60%, 65%, 70%, 75%, 80%, 85%, 90%, or 95%. The degree of reduction will generally depend on the zygosity of the sample; for example, a sample wherein the CGG-rich region is from an individual heterozygous for an allele comprising the CGG-rich region, or for a specific AGG repeat, may show a reduction in the amount of the corresponding products ranging from 25% to 75%. A sample wherein the CGG-rich region is from an individual hemizygous or homozygous for an allele comprising the CGG-rich region, or for a specific AGG repeat, may show a reduction in the amount of the corresponding products ranging from 50% to 95% or more.

In some embodiments, the methods do not require the use of external standards or calibrators such as, for example, reference standards or molecular ladders. This independence can be achieved because in some embodiments, peaks corresponding to products differing in length by one trinucleotide repeat can be used to count up to the size of the largest product, wherein the count can indicate the number of repeats in the template (subject to any necessary adjustment according to the number of repeats comprised by the primer). In some embodiments, the spacing between peaks in part of the representation of product size and amount can be used to estimate the size of the largest product, e.g., by extrapolation; this can be useful when resolution of peaks corresponding to larger repeat numbers is insufficient to count all peaks up to and including that of the largest product.

In some embodiments, the methods can determine the number of repeats in the CGG-rich region to within 100, 50, 20, 10, 5, 4, 3, 2, 1, or 0 repeats. Determination of a quantity "within 0 units" means that its precise value is determined. In some embodiments, the methods comprise determining the number of repeats in the CGG-rich region to within 100, 50, 20, 10, 5, 4, 3, 2, 1, or 0 repeats. For example, the methods can comprise determining the number of repeats in a CGG-rich region comprising less than 70 CGG repeats to within 5, 4, 3, 2, 1, or 0 repeats; determining the number of repeats in a CGG-rich region comprising from 70 to 120 CGG repeats to within 10, 5, 4, or 3 repeats; or determining the number of repeats in a CGG-rich region comprising greater than 120 CGG repeats, up to about 200 CGG repeats, to within 20, 10, or 5 repeats. Determination of accuracy levels for even larger CGG repeat regions can be difficult due to the lack of reliable known standards.

In some embodiments, the methods can determine the position of an interruptor element to within 60, 45, 30, 15, 12, 9, 6, 5, 4, 3, 2, 1, or 0 nucleotides. The position of the interruptor element can be determined, for example, in terms of distance relative to either end of the CGG-rich region.

In some embodiments, at least one of the primers comprises a radiologically or electromagnetically detectable moiety. Radiologically detectable moieties include radioactive isotopes that emit detectable particles, such as beta or gamma particles, for example, $^{14}C$, $^{3}H$, $^{32}P$, $^{33}P$, $^{35}S$, and $^{125}I$. Electromagnetically detectable moieties include chemical entities that interact with electromagnetic radiation (including absorbance, emission, or both) in a detectable way, such as chromophores and fluorophores, for example, fluorescein, FAM, cyanine dyes, rhodamine dyes, etc.

Additional aspects of the invention will be set forth in part in the description which follows, and in part will be obvious from the description, or may be learned by practice of the invention. The aspects of the invention will be realized and attained by means of the elements and combinations particularly pointed out in the appended claims.

BRIEF DESCRIPTION OF THE DRAWINGS

The accompanying drawings, which are incorporated in and constitute a part of this specification, illustrate several embodiments of the invention and together with the description, serve to explain the principles of the invention.

| | |
|---|---|
| FAM_FX-F | 5'-FAM-TCAGGCGCTCAGCTCCGTTTCGGTTTCAC TTCCGGT (SEQ ID NO: 38) |
| Tag-(CCG)$_4$ | AGCGTCTACTGTCTCGGCACTTGCCCGCCGCCGCCG (SEQ ID NO: 39) |

A template comprising (CGG)$_{10}$AGG(CGG)$_9$AGG(CGG)$_9$ (SEQ ID NO: 42) is shown. It represents a possible CGG repeat region in the 5' UTR of FMR1. The primer Tag-(GCC)$_4$ can bind internally at multiple positions in the repeat region; with the FAM labeled forward primer (FAM-FX-F), which anneals upstream of the CGG repeat region, it can amplify a plurality of PCR products. The shortest CGG amplicon will have 4 CGG repeats and the longest CGG amplicon will comprise the full length of SEQ ID NO: 40. Any products that are significantly longer than the full length products are considered non-specific products.

Figure 1:
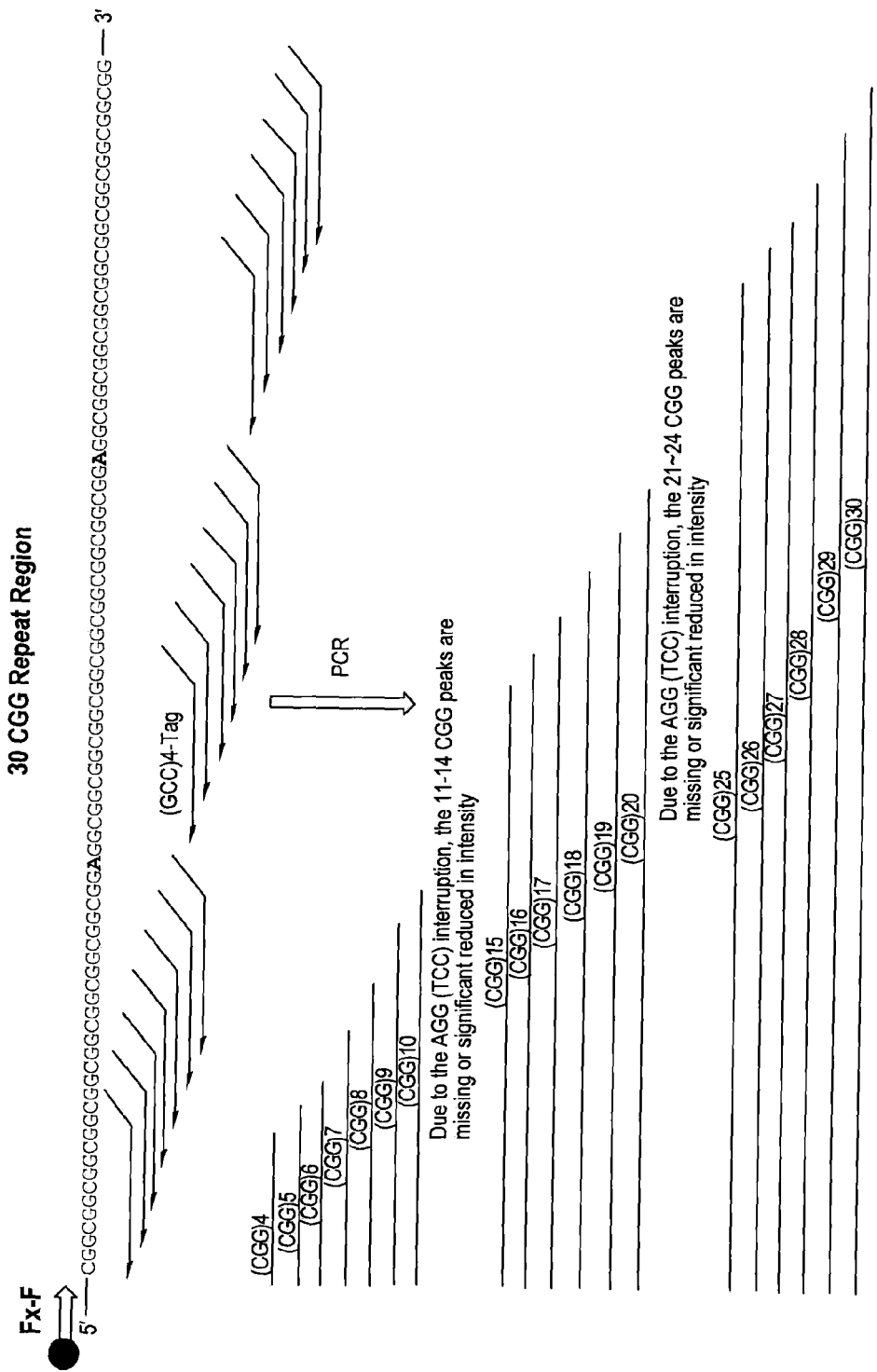
FIG. 1 outlines amplification of a CGG-rich template comprising AGG trinucleotides. The primer sequences are
Figure 2A:
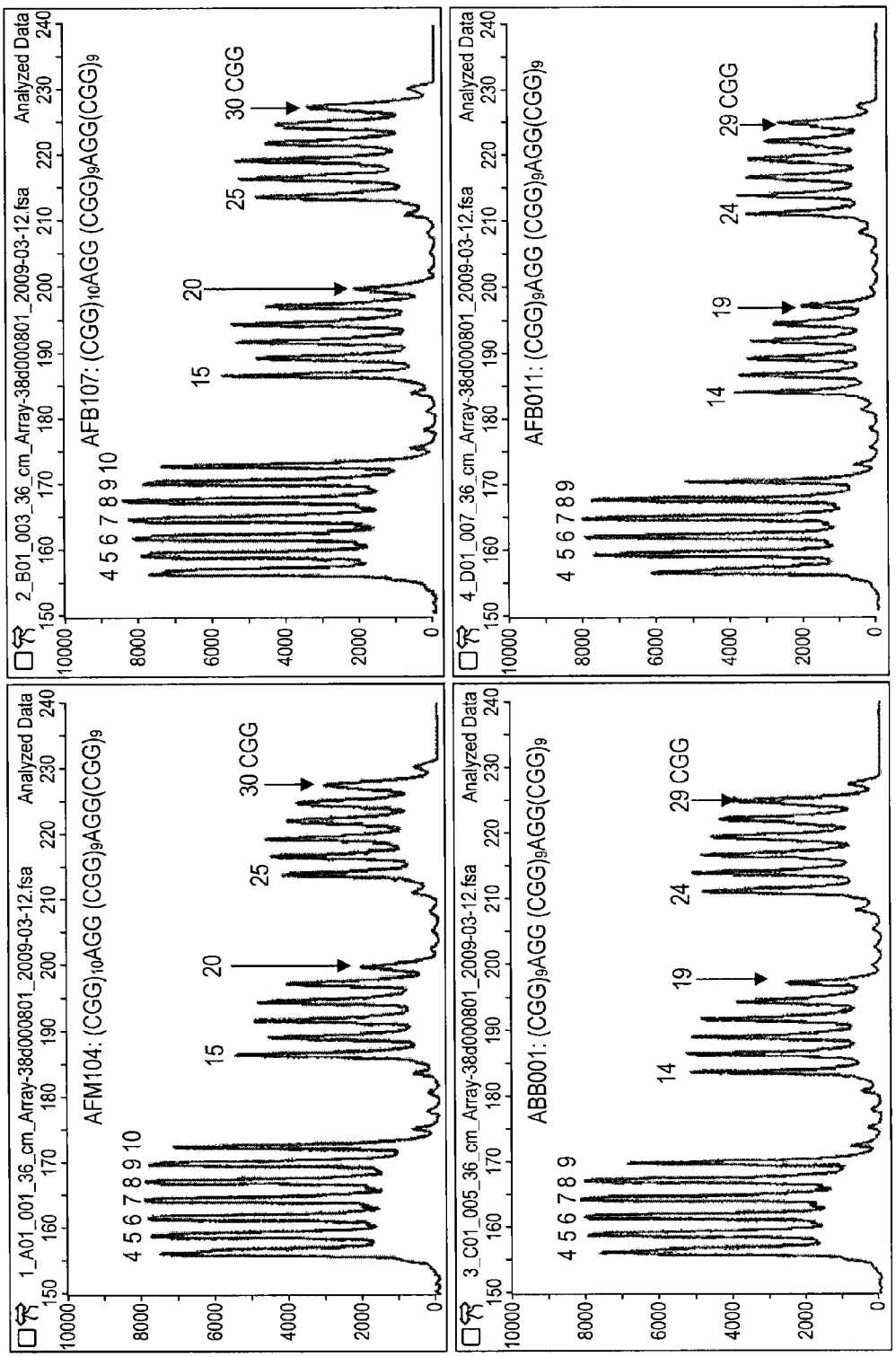
Figure 2B:
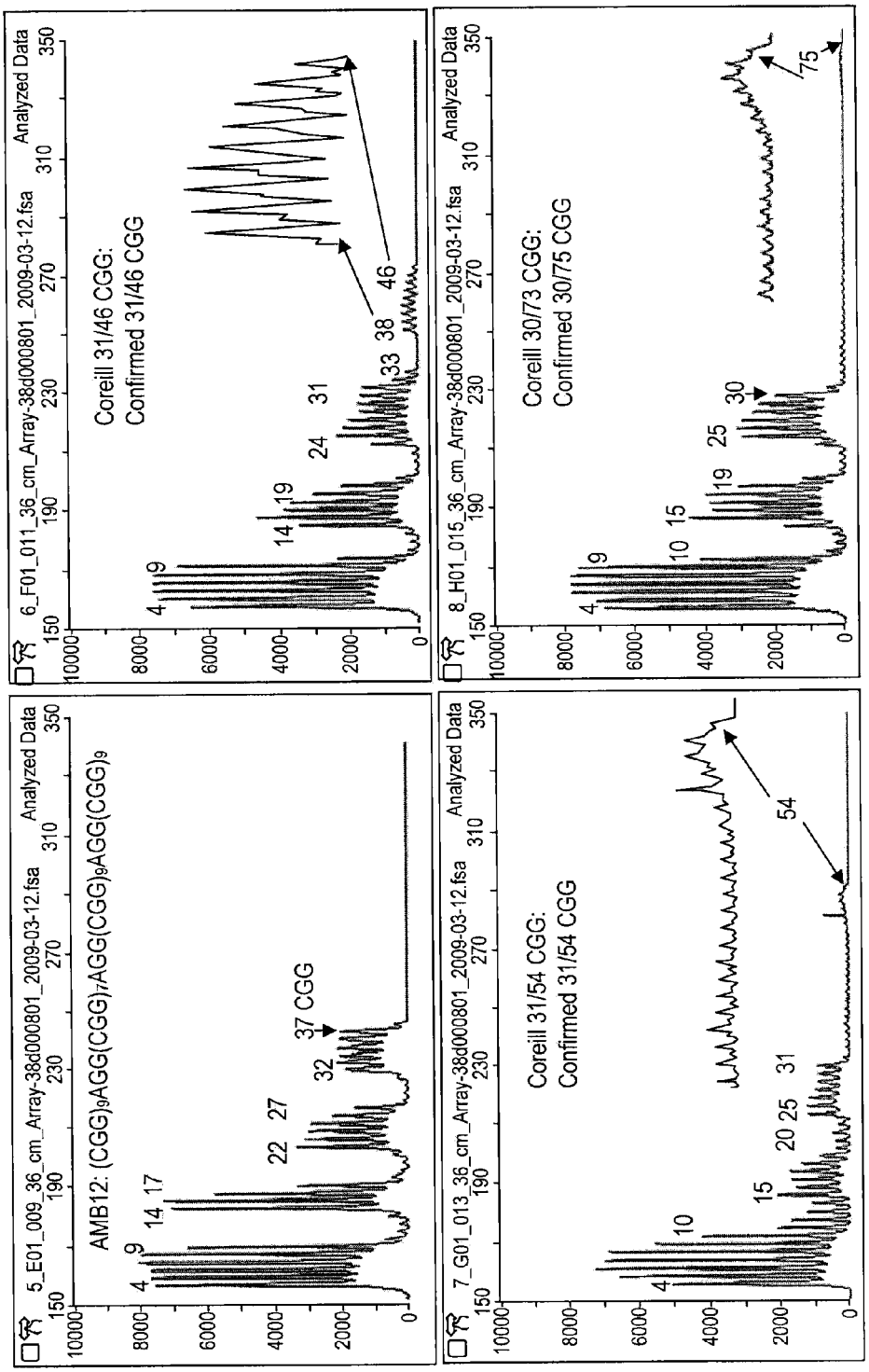

FIGS. 2A and 2B show electropherograms of PCR results from 5 clinic samples (AFM104, AFB107, ABB001, AFB011, and AMB12, as indicated in the plot areas in FIG. 2A and the top left panel of FIG. 2B) and three Coriell standards (31/46 CGG, 31/54 CGG, and 30/75 CGG, as indicated in the plot areas of FIG. 2B other than the top left). For the clinic samples, the sequence of the CGG rich regions as determined by sequencing are listed in the plot areas. For the Coriell standards, the CGG repeat content of the two FMR1 5' UTR alleles present in the sample as indicated by the electropherogram is listed as "Confirmed." Selected peaks are labeled with the number of CGG trinucleotides comprised by the product corresponding to the peak. Units on the vertical axis represent fluorescence intensity and are arbitrary. Units on the horizontal axis represent estimated size in nucleotides. These estimated sizes were determined based on the scan number (related to retention time) of the CE instrument. SEQ ID NOs for the nucleic acid sequences appearing in FIG. 2A are as follows: AFM104 and AFM107 panels, SEQ ID NO: 46; ABB001 and AFB011 panels, SEQ ID NO: 57. The SEQ ID NO for the nucleic acid sequence appearing in FIG. 2B is as follows: AMB12 panel, SEQ ID NO: 62.

Figure 3A:
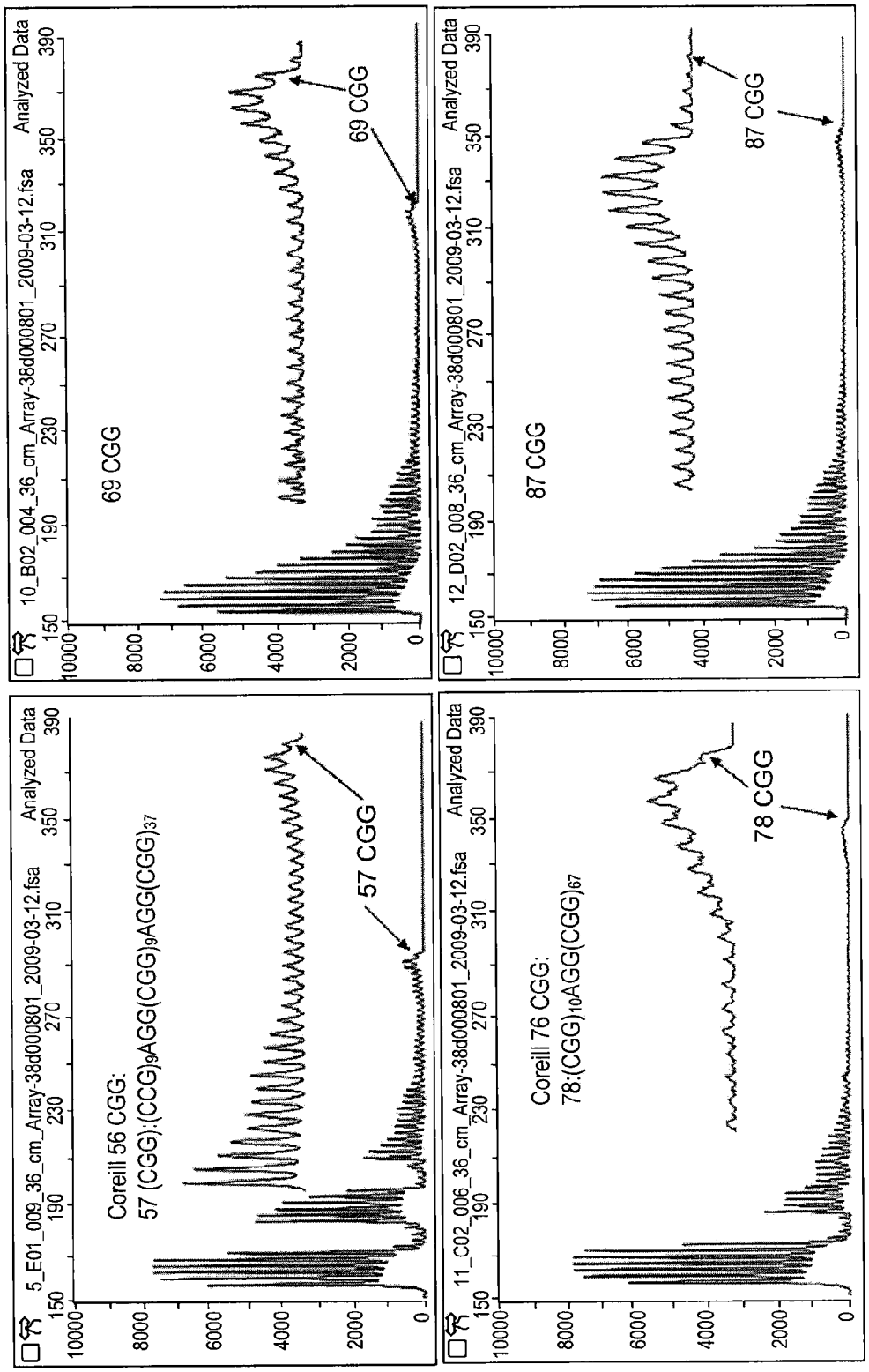
Figure 3B:
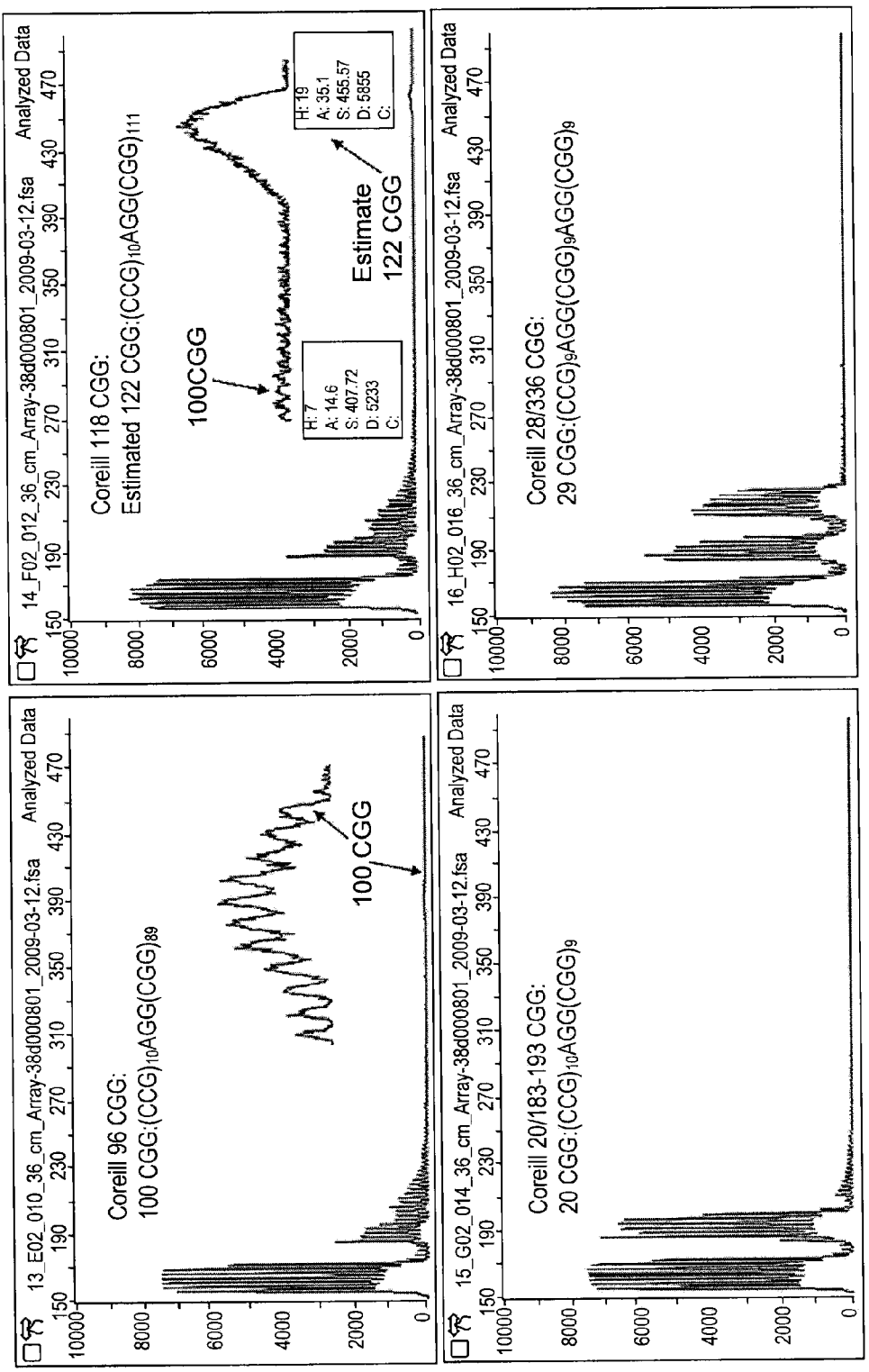

FIGS. 3A and 3B show electropherograms of PCR results from eight Coriell standards. In each, the peak corresponding to the maximum detected number of CGG trinucleotides is indicated when it was resolvable. In cases where the number of trinucleotides differed from the Coriell designation or where AGG trinucleotides are detected, the sequence deduced from the electropherogram is indicated in the plot area. In the top right panel of FIG. 3B, not all peaks corresponding to individual product species could be resolved, but the position of the rightmost peak corresponded to an estimated content of 122 CGG trinucleotides. In the two bottom panels, amplification of products near the full length of the longer alleles was not detected. Horizontal and vertical axis labels are as in FIG. 2A. SEQ ID NOs for the nucleic acid sequences appearing in FIG. 3A are as follows: Coreill 56 CGG panel, SEQ ID NO: 63; Coreill 76 CGG panel, SEQ ID NO: 64. SEQ ID NOs for the nucleic acid sequences appearing in FIG. 3B are as follows: Coreill 96 CGG panel, SEQ ID NO: 65; Coreill 118CGG panel, SEQ ID NO: 66; Coreill 201183-193 CGG panel, SEQ ID NO 67; Coreill 28/336 CGG panel, SEQ ID NO: 57.

Figure 4:
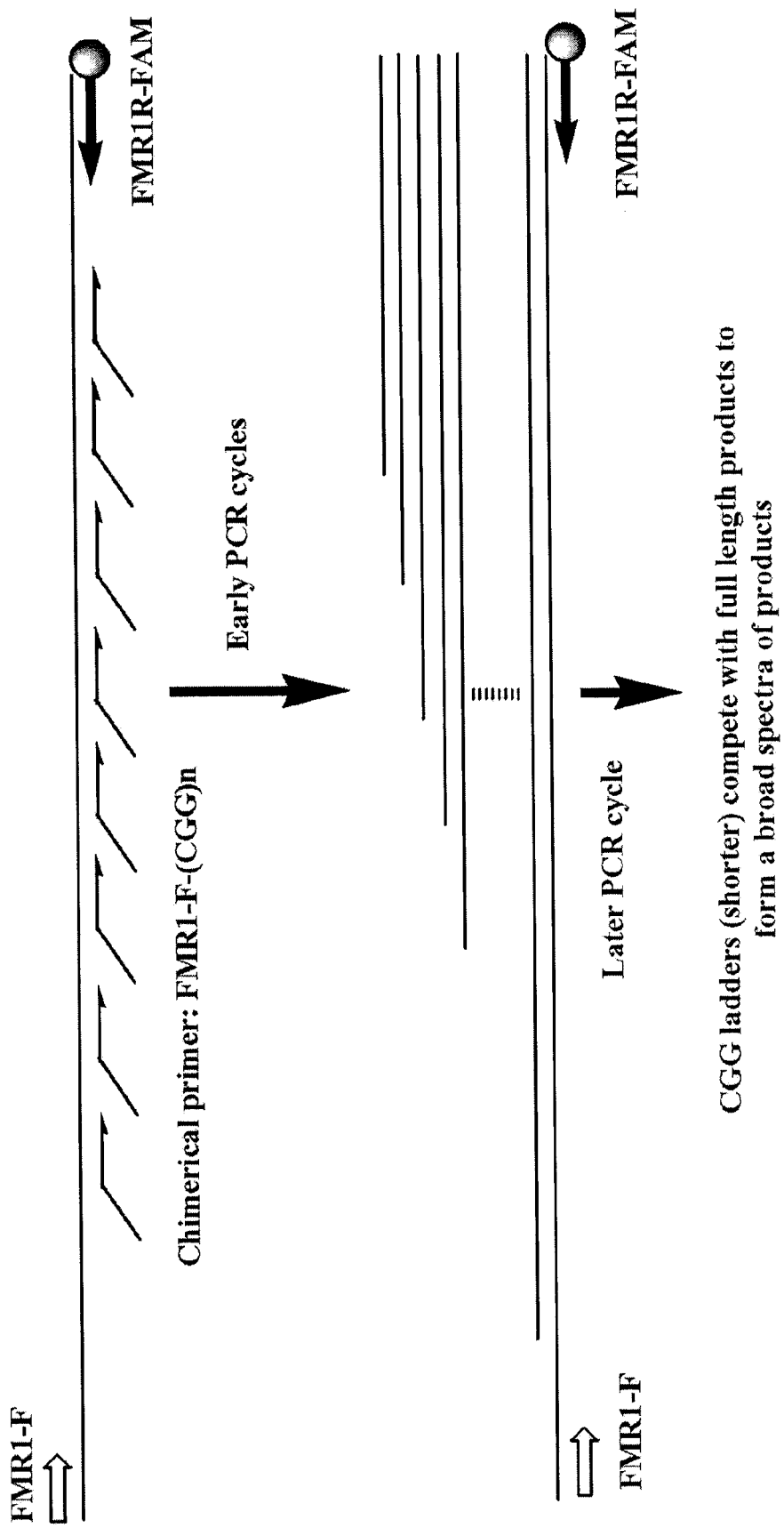

FIG. 4 represents an assay using three primers. FMR1R-FAM anneals downstream of the CGG repeat region and comprises a FAM fluorophore, for use in detection of products. The chimerical primer comprises CGG repeats and also a 5' flap that matches the sequence of the third primer, in this case FMR1-F, which anneals to the original template as indicated but also anneals to products which comprise the chimerical primer sequence. The chimerical primer is provided at a lower concentration so that it is consumed rapidly so as to limit the progressive reduction in product size from cycle to cycle.

Figure 5:
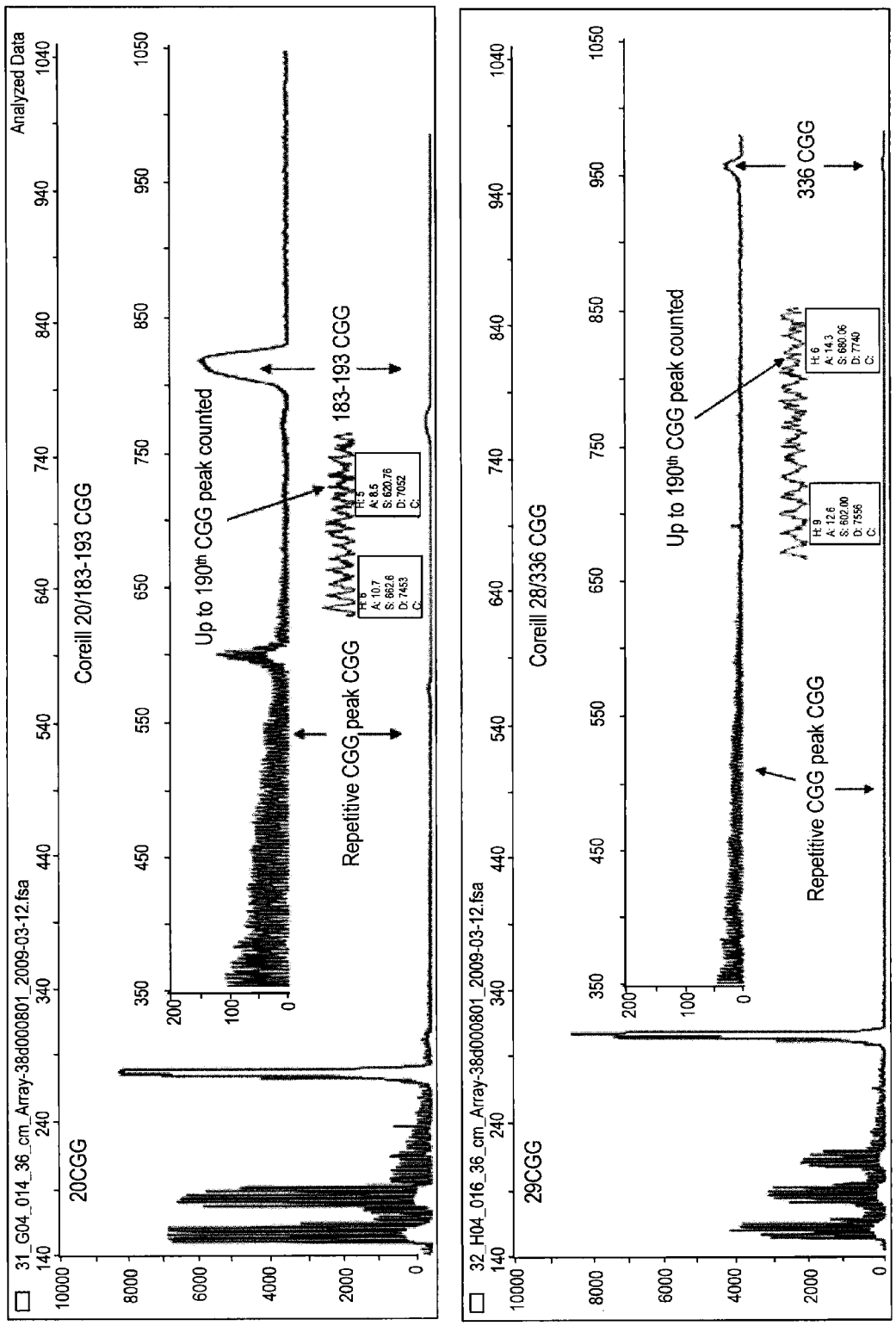

FIG. 5 shows electropherograms of PCR results from a three primer assay of the heterozygous Coriell standards indicated in each plot area. Horizontal and vertical axis labels are as in FIG. 2A. In each panel, the highest peak corresponds to the shorter of the two alleles present in the sample and is indicated according to the number of CGG repeats determined by this assay. Peaks were counted up to the 190th peak, which is shown as an inset enlargement.

Figure 6:
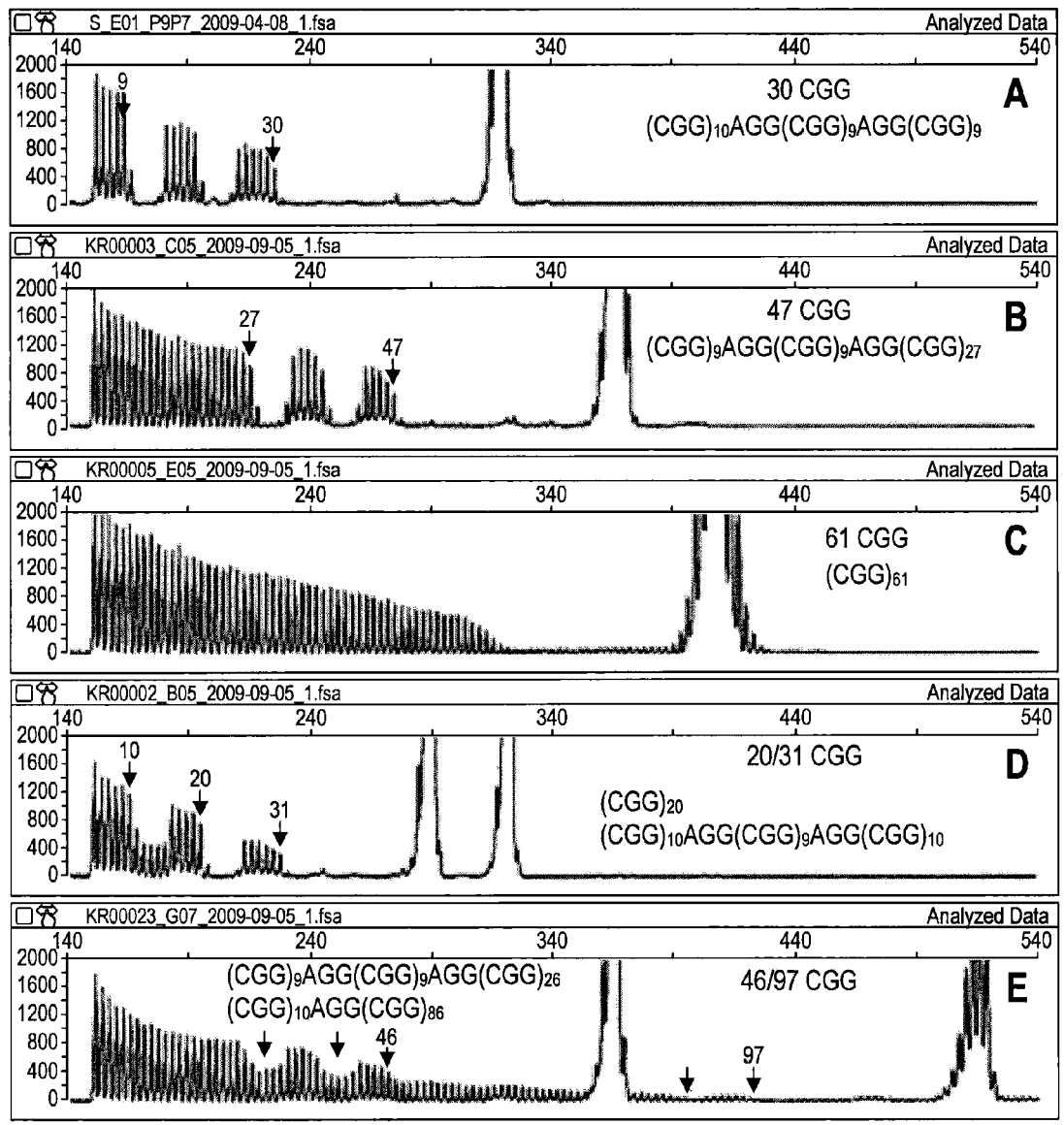

FIG. 6 shows electropherograms of PCR results from five genomic DNA samples (panels A, B, C, D, and E). Panels A, B, and C are derived from male genomic DNA samples. Panels D and E are derived from female genomic DNA samples. Selected peaks are labeled with the number of CGG trinucleotides comprised by the product corresponding to the peak. Predicted sequences of genomic alleles are listed in the plot areas. Units on the vertical axis represent fluorescence intensity and are arbitrary. Units on the horizontal axis represent estimated size in nucleotides. As described in the Examples, the samples that were used to generate the profiles of panels A-E were determined to have CGG-repeat regions with the following sequences. Panel A: 5'-(CGG)$_{10}$AGG (CGG)$_9$AGG(CGG)$_9$-3' (SEQ ID NO:46). Panel B: 5'-(CGG)$_9$AGG(CGG)$_9$AGG(CGG)$_{27}$-3' (SEQ ID NO:47). Panel C: 5'-(CGG)$_{61}$-3' (SEQ ID NO:48). Panel D: 5'-(CGG)$_{20}$-3' (SEQ ID NO:49) and 5'-(CGG)$_{10}$AGG (CGG)$_9$AGG(CGG)$_{10}$-3' (SEQ ID NO:50). Panel E: 5'-(CGG)$_9$AGG(CGG)$_9$AGG(CGG)$_{26}$-3' (SEQ ID NO:51) and 5'-(CGG)$_{10}$AGG(CGG)$_{86}$-3' (SEQ ID NO:46).

Figure 7:
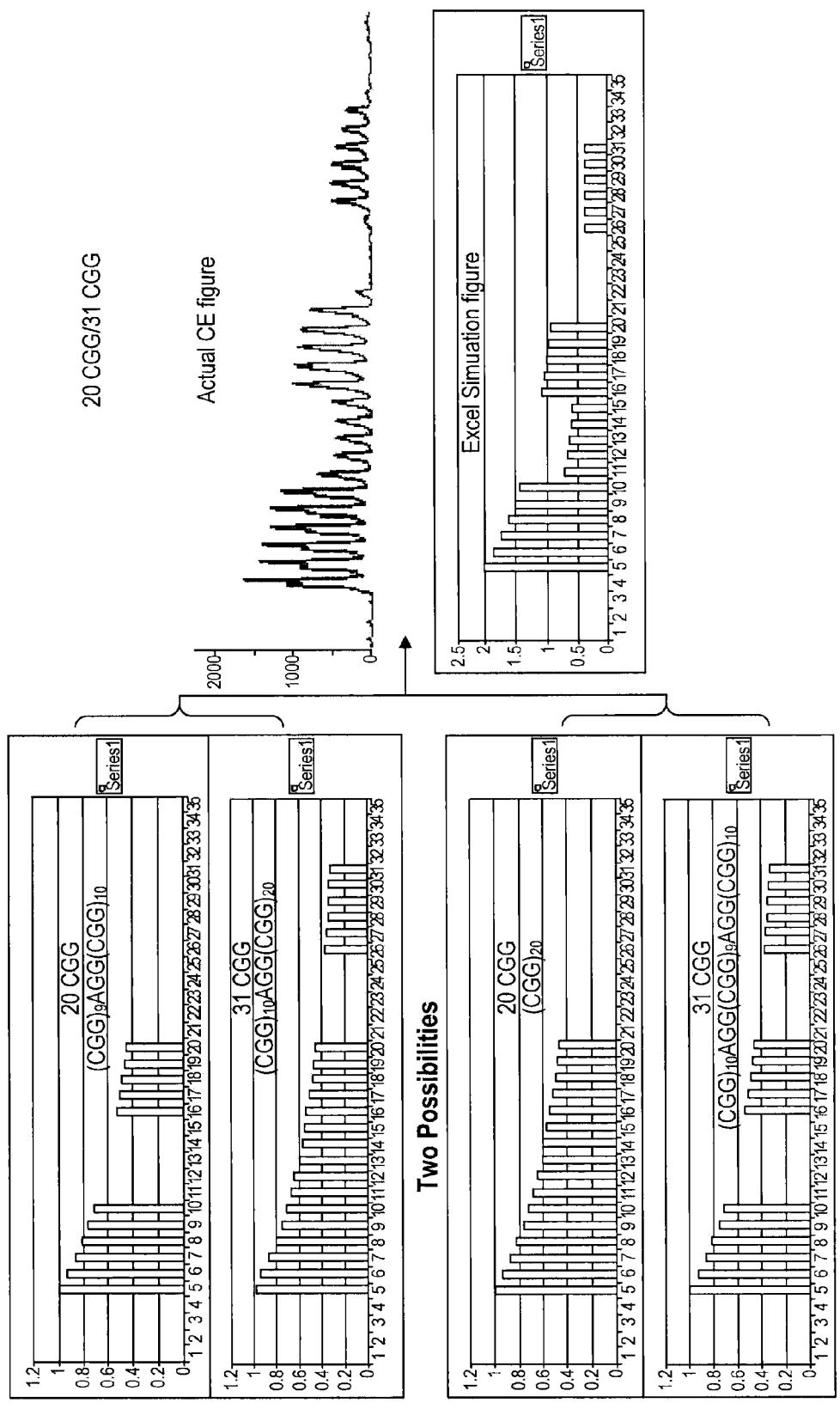

FIG. 7 shows predicted CE electropherograms (top and bottom left side panels) for two different AGG repeat assignments for different alleles (top panel, 5'-(CGG)$_9$AGG (CGG)$_{10}$-3' (SEQ ID NO:53) and 5'-(CGG)$_{10}$AGG(CGG)$_{20}$-3' (SEQ ID NO: 54); bottom panel, 5'-(CGG)$_{20}$-3' (SEQ ID NO:49) and 5'-(CGG)$_{10}$AGG(CGG)$_9$AGG(CGG)$_{10}$-3' (SEQ ID NO:50)) and a simulation CE electropherogram for amplification products of both alleles (bottom right panel). The observed CE electropherogram is shown in the top right panel.

Figure 8:
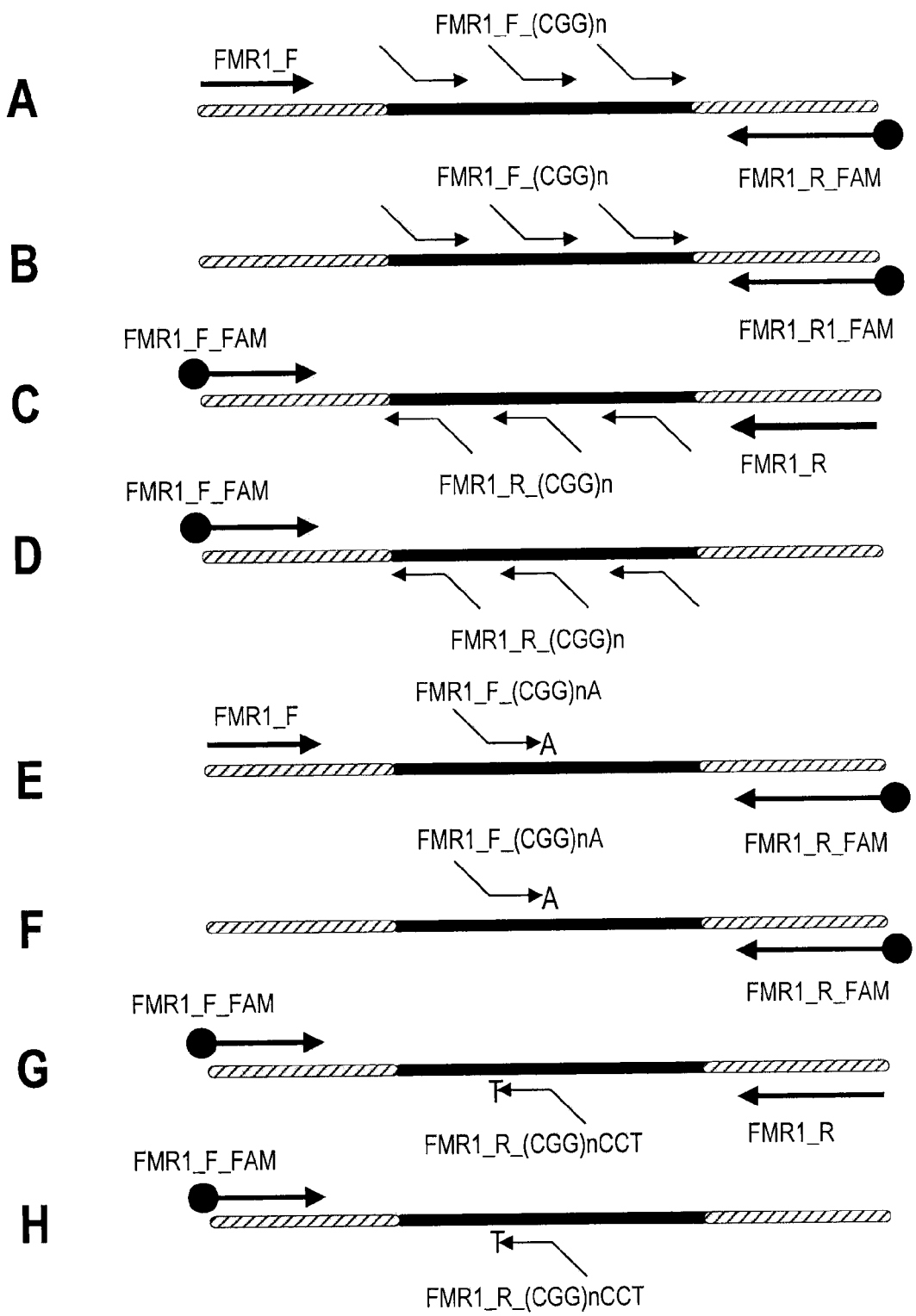

FIG. 8 represents eight amplification assays that can be used in methods of the invention. FMR1_F anneals upstream of the CGG repeat region. FMR1_R anneals downstream of the CGG repeat region. FMR1_F_FAM and FMR1_R_FAM correspond to the same two primers respectively, but comprising a FAM fluorophore, for use in detection of products. FMR1_F_(CGG)n is a chimerical primer that comprises CGG repeats and a 5' flap that matches the sequence of FMR1_F, which anneals to the original template as indicated and also anneals to products which comprise the chimerical primer sequence. The chimerical primer can be provided at a lower concentration so that it is consumed rapidly, so as to limit the progressive reduction in product size from cycle to cycle. FMR1_R_(CCG)n is a chimerical primer that comprises CCG repeats and a 5' flap that matches the sequence of FMR1_R, which anneals to the original template as indicated and also anneals to products which comprise the chimerical primer sequence. FMR1_F_(CGG)nA is a chimerical primer corresponding to FMR1_F_(CGG)n but also having a 3' terminal dA. The 3' terminal dA anneals to the T on the DNA strand in the region of complementarity to the AGG sequence present in some CGG repeat regions. FMR1_R_(CCG)nCCT is a chimerical primer with the same sequence as FMR1_R_(CCG)n but also having a 3' terminal dCdCdT. The terminal dCdCdT anneals to the AGG sequence present on the complementary DNA strand in some CGG repeat regions. The primer sequences used for these assays can be, for example:

| | |
|---|---|
| FMR1_F | TCAGGCGCTCAGCTCCGTTTCGGTTTCA (SEQ ID NO: 14) |
| FMR1_F_FAM | 5'-FAM-TCAGGCGCTCAGCTCCGTTTCGGTTCA (SEQ ID NO: 14) |
| FMR1_F_(CGG)$_5$ n = 5 | TCAGGCGCTCAGCTCCGTTTCGGTTTCACGG CGGCGGCGGCGG (SEQ ID NO: 41) |
| FMR1_R | AAGCGCCATTGGAGCCCCGCACTTCC (SEQ ID NO: 37) |
| FMR1_R_FAM | 5'-FAM-AAGCGCCATTGGAGCCCCGCACTT CC (SEQ ID NO: 37) |
| FMR1_R_(CCG)$_5$ n = 5 | AAGCGCCATTGGAGCCCCGCACTTCCCCGCC GCCGCCGCC (SEQ ID NO: 43) |

```
                    -continued
FMR1_F_(CGG)5A      TCAGGCGCTCAGCTCCGTTTCGGTTTCACGG
n = 5               CGGCGGCGGCGGA
                    (SEQ ID NO: 44)

FMR1_R_(CCG)4CCT    AAGCGCCATTGGAGCCCCGCACTTCCCCGCC
n = 4               GCCGCCGCCT
                    (SEQ ID NO: 45)
```

The FMR_F and FMR_R sequences shown may be substituted by any other suitable primer sequence from the 5' and 3' regions flanking the CGG repeats, respectively.

Figure 9:
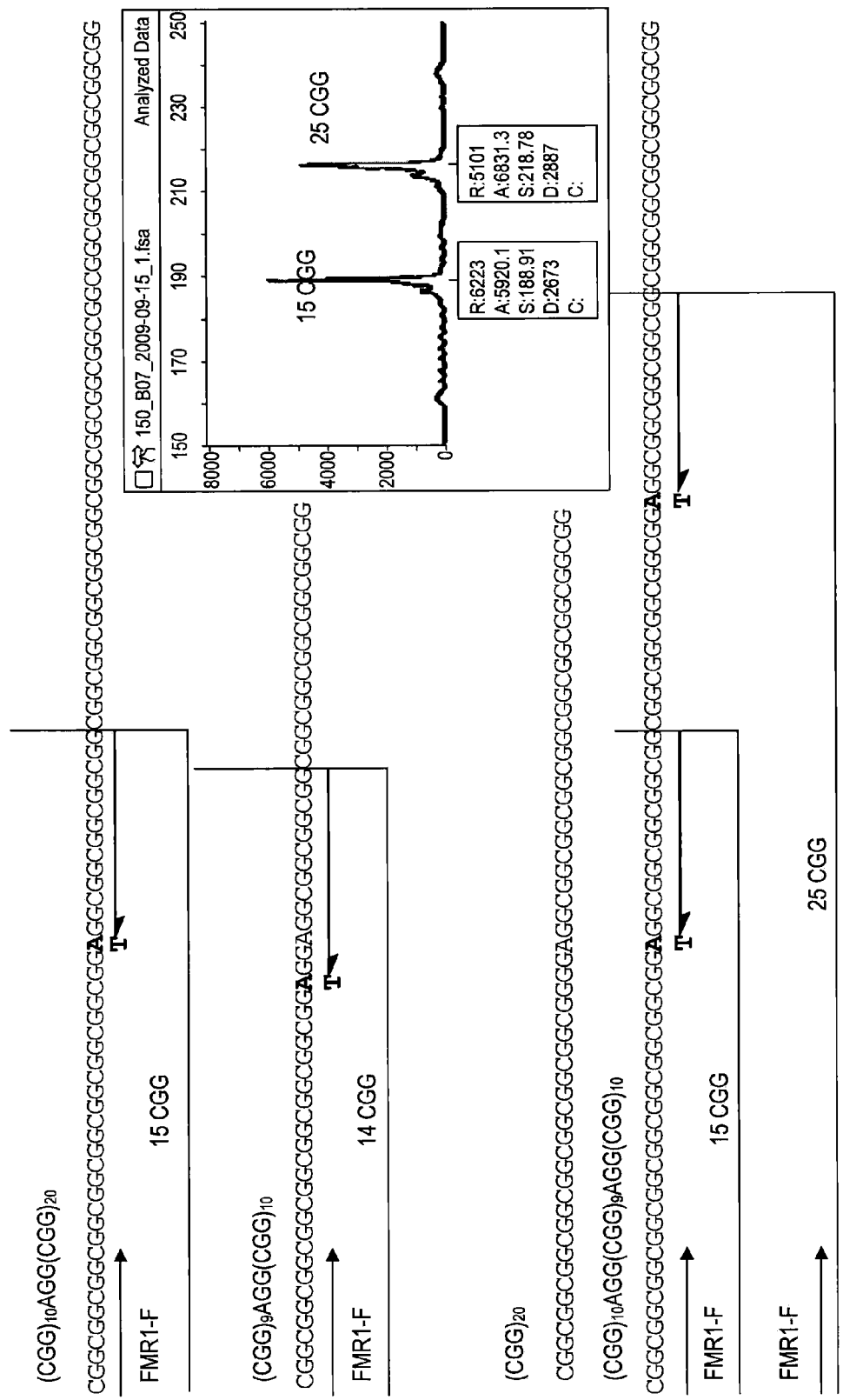

FIG. 9 outlines amplification of a CGG rich template comprising AGG trinucleotides, according to the PCR scheme shown in FIG. 8H. The top and bottom portions of the figure represent two possible allele configurations present in the genomic DNA sample whose actual CE electropherogram is shown in FIG. 6D. The top portion outlines amplification of two alleles including a 31 repeat allele having an AGG sequence present after the $10^{th}$ CGG repeat (5'-(CGG)$_{10}$AGG(CGG)$_{20}$3' (SEQ ID NO:54)) and a 20 repeat allele having an AGG present after the $9^{th}$ CGG repeat (5'-(CGG)$_9$AGG(CGG)$_{10}$-3' (SEQ ID NO:53)). The bottom portion outlines amplification of two alleles including a 20 repeat allele having no AGG sequence within the CGG repeats (5'-(CGG)$_{20}$-3' (SEQ ID NO: 49)) and a 31 repeat allele having an AGG present at repeat position 11 and an AGG at repeat position 21 (5'-(CGG)$_{10}$AGG(CGG)$_9$AGG(CGG)$_{10}$-3' (SEQ ID NO: 50)). The panel at the right shows an actual CE electropherogram of amplification products from the genomic DNA sample, demonstrating the presence of amplification products representing the allele configuration in the bottom portion of the figure.

Figure 10:
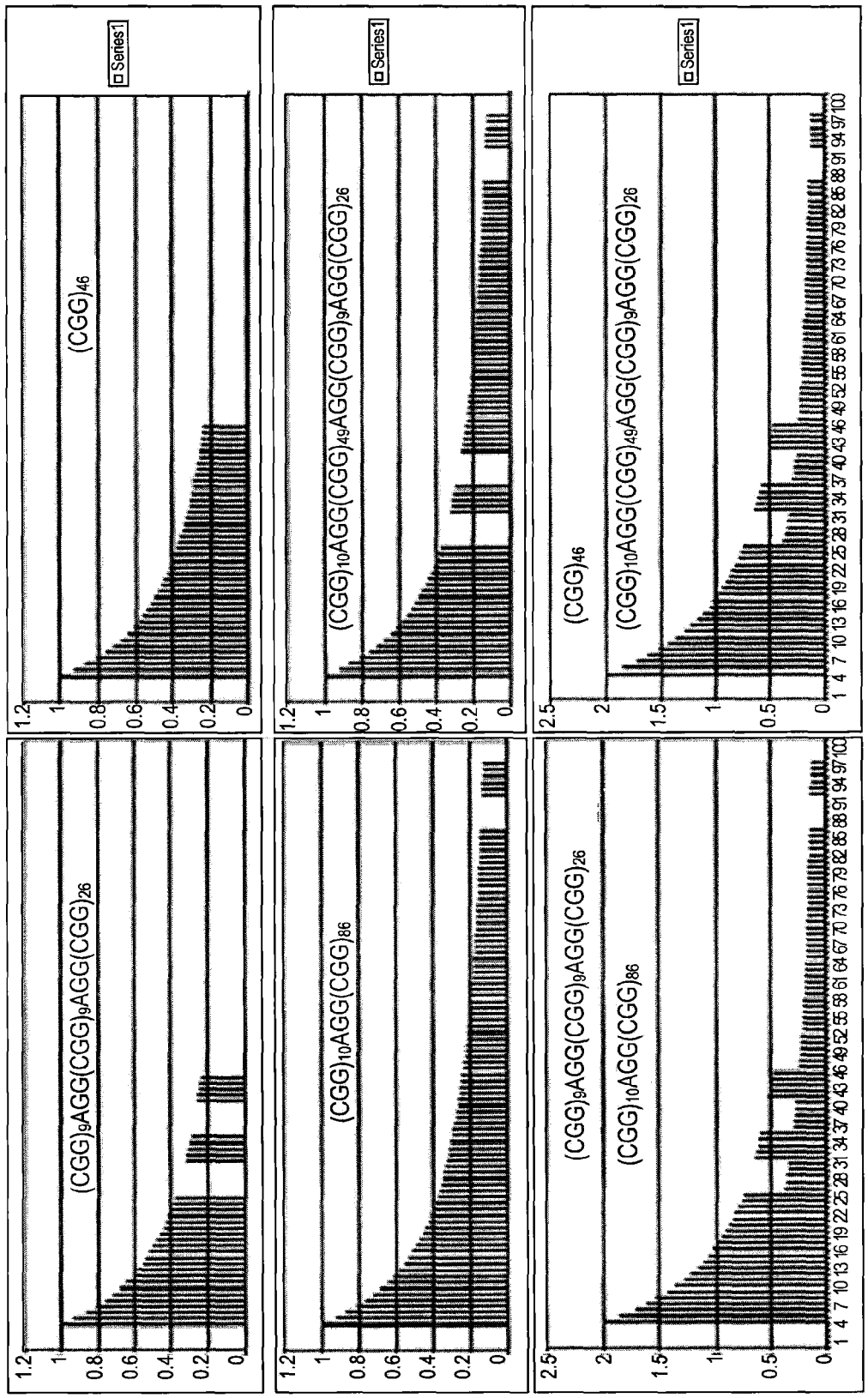

FIG. 10 shows simulated CE electropherograms of allele amplification products that would be generated by the PCR scheme shown in FIG. 8B from the genomic DNA sample whose actual CE electropherogram is shown in FIG. 6E and which contains alleles having 46 and 97 CGG repeats. Upon amplification according to the PCR scheme in FIG. 8B, two possible allele configurations (left panels, 5'-(CGG)$_9$AGG (CGG)$_9$AGG(CGG)$_{26}$-3' (SEQ ID NO: 51) and 5'-(CGG)$_{10}$ AGG(CGG)$_{86}$-3' (SEQ ID NO: 52); right panels, 5'-(CGG)$_{46}$-3' (SEQ ID NO: 55) and 5'-(CGG)$_{10}$AGG (CGG)$_{49}$AGG(CGG)$_9$AGG(CGG)$_{26}$-3' (SEQ ID NO: 56)) would generate identical CE electropherograms as shown in the left and right bottom panels and in FIG. 6E.

Figure 11:
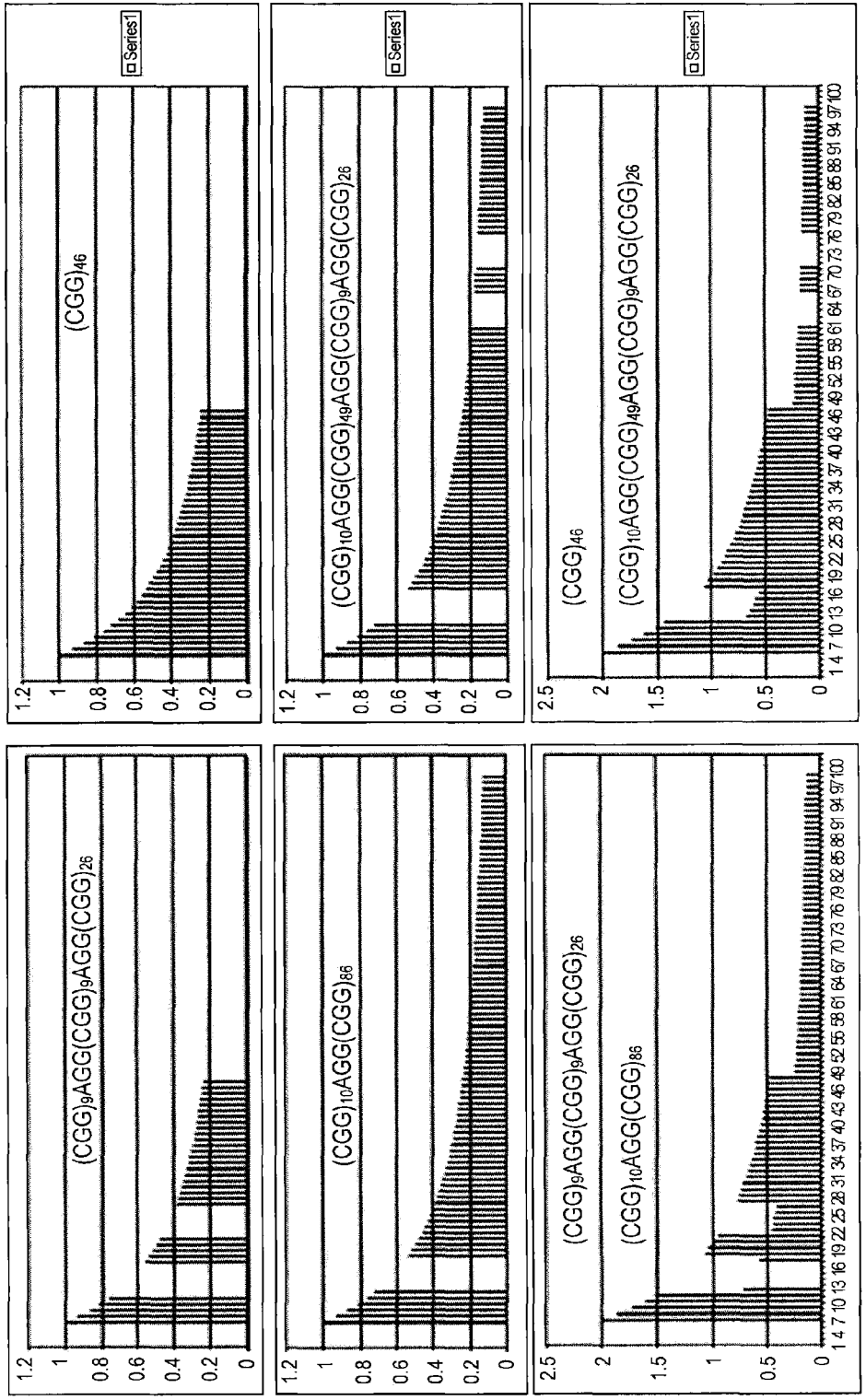

FIG. 11 shows simulated CE electropherograms of allele amplification products that would be generated by the PCR scheme shown in FIG. 8D from the genomic DNA sample whose actual CE electropherogram is shown in FIG. 6E and which contains alleles having 46 and 97 CGG repeats. This figure simulates the amplification products from the two possible allele configurations (left panels, 5'-(CGG)$_9$AGG (CGG)$_9$AGG(CGG)$_{26}$-3' (SEQ ID NO: 51) and 5'-(CGG)$_{10}$ AGG(CGG)$_{86}$-3' (SEQ ID NO: 52); right panels, 5'-(CGG)$_{46}$-3' (SEQ ID NO: 55) and 5'-(CGG)$_{10}$AGG (CGG)$_{49}$AGG(CGG)$_9$AGG(CGG)$_{26}$-3' (SEQ ID NO: 56)), following amplification by the PCR assay scheme shown in FIG. 8D, in which the directionality of the repeat primer (FMR_R_(CCG)n) is reversed. The two allele scenarios would generate different CE profiles (FIG. 11, bottom panels).

Figure 12:
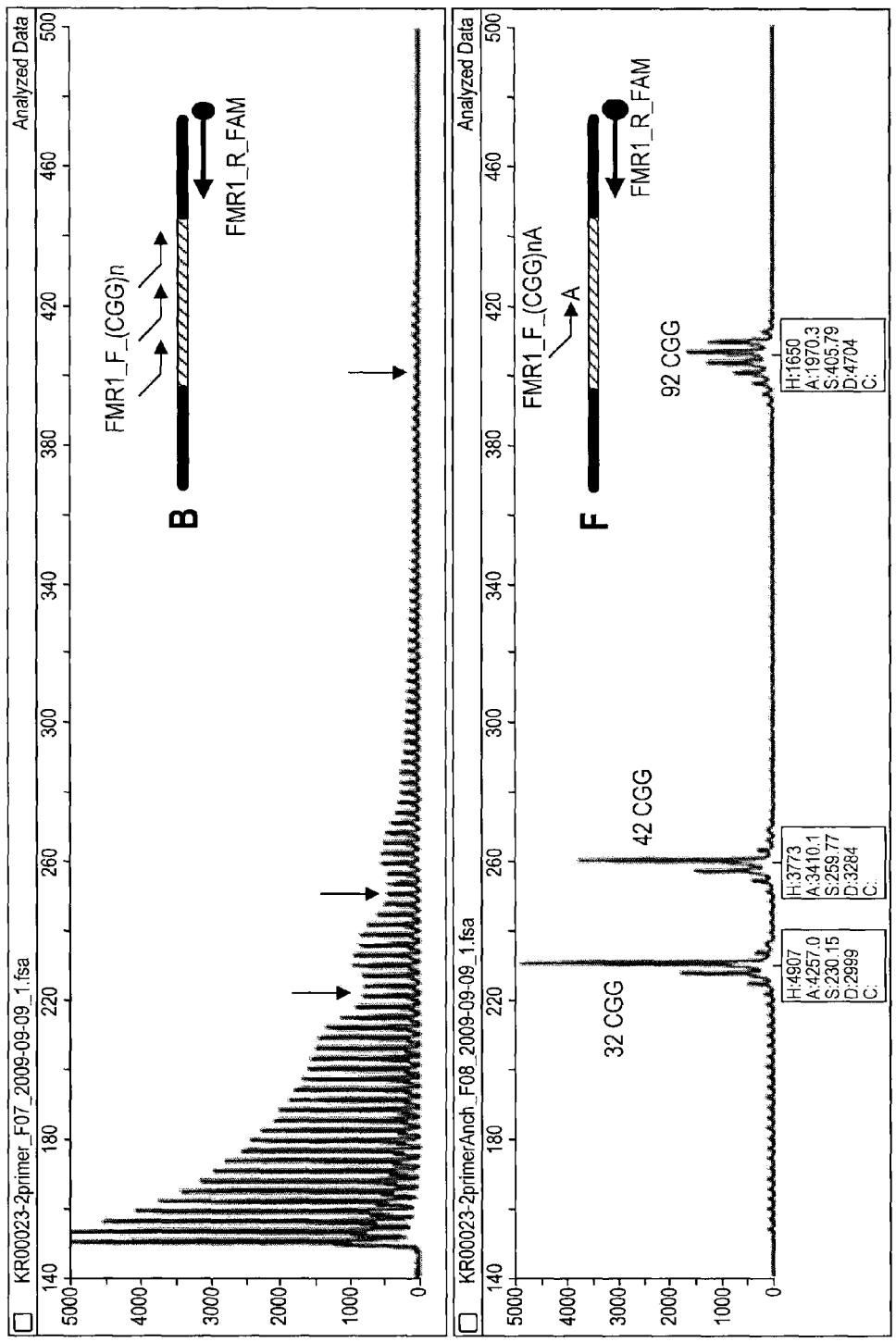

FIG. 12 shows an actual CE electropherogram of allele amplification products from the same genomic DNA sample described in the descriptions of FIGS. 10 and 11 above (containing the 46/97 CGG repeat allele). The CE electropherograms were generated from samples amplified according to the PCR assay scheme in FIG. 8B (top panel) or FIG. 8F (bottom panel).

Figure 13:
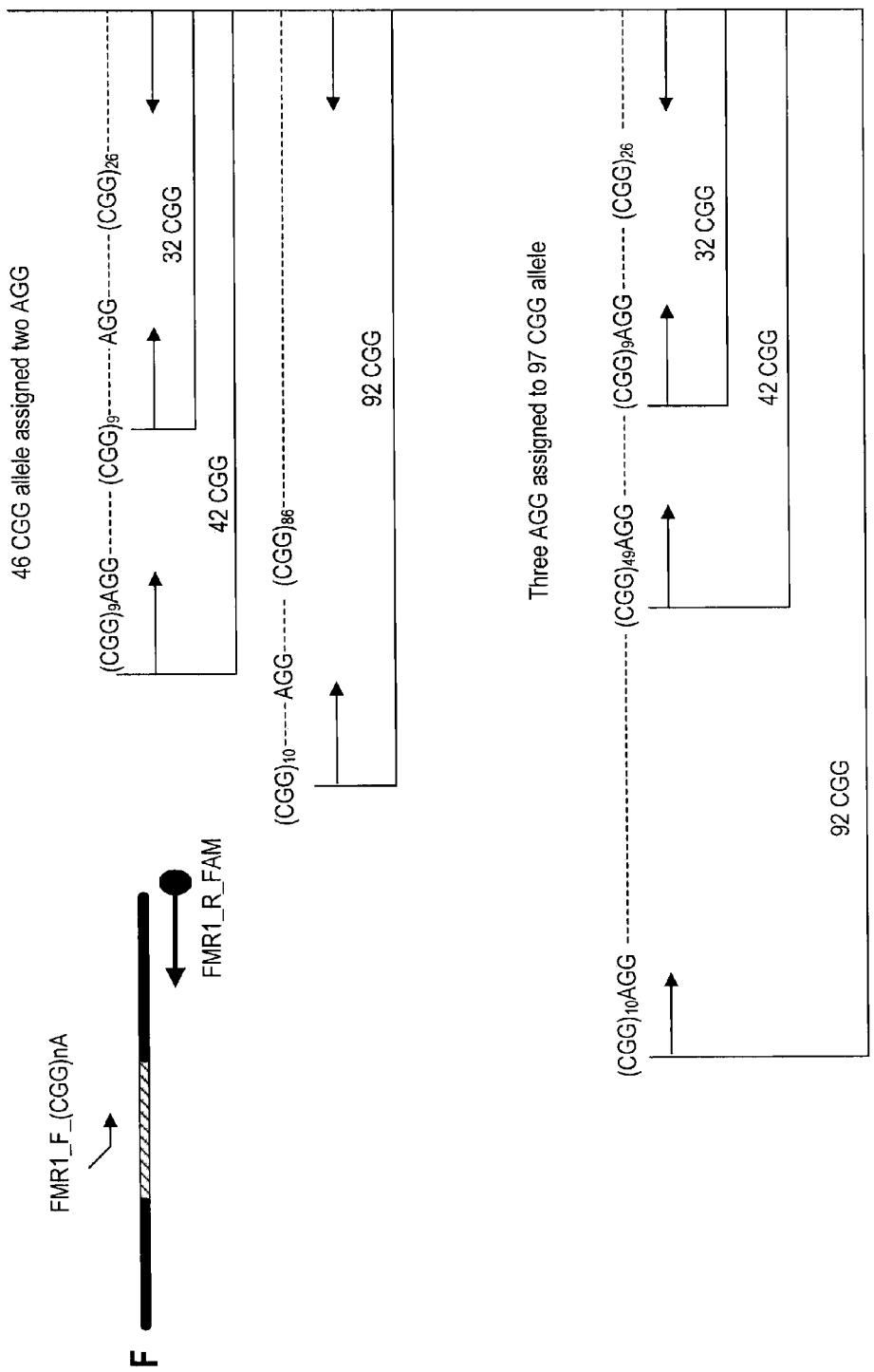

FIG. 13 schematically shows the expected amplification products from the same genomic DNA sample described in the descriptions of FIGS. 10, 11, and 12 above (containing the 46/97 CGG repeat allele) (5'-(CGG)$_9$AGG(CGG)$_9$AGG (CGG)$_{26}$-3' (SEQ ID NO: 51), 5'-(CGG)$_{10}$AGG(CGG)$_{86}$-3' (SEQ ID NO: 52), 5'-(CGG)$_{46}$-3' (SEQ ID NO: 55), and 5'-(CGG)$_{10}$AGG(CGG)$_{49}$AGG(CGG)$_9$AGG(CGG)$_{26}$-3' (SEQ ID NO: 56)), following amplification by the PCR assay scheme shown in FIG. 8F.

Figure 14:
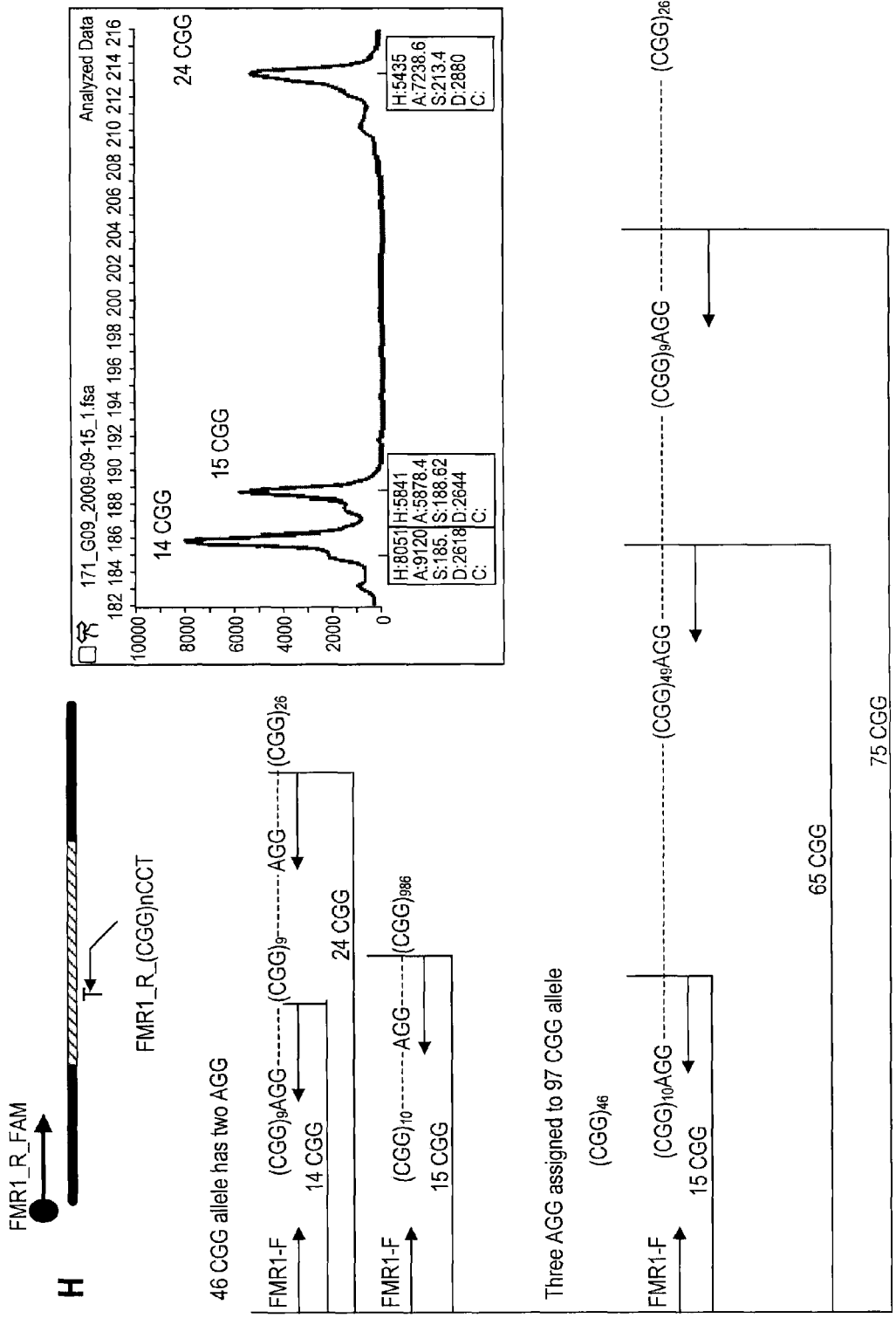

FIG. 14 shows schematically the amplification products that would be expected using the PCR assay scheme of FIG. 8H, following amplification of genomic DNA (described in the descriptions of FIGS. 10-13 above and containing the 46/97 CGG repeat allele) with two different allele scenarios (top portion of the figure: 5'-(CGG)$_9$AGG(CGG)$_9$AGG (CGG)$_{26}$-3' (SEQ ID NO: 51) and 5'-(CGG)$_{10}$AGG(CGG)$_{86}$-3' (SEQ ID NO: 52); bottom portion of the figure: 5'-(CGG)$_{46}$-3' (SEQ ID NO: 55) and 5'-(CGG)$_{10}$AGG (CGG)$_{49}$AGG(CGG)$_9$AGG(CGG)$_{26}$-3' (SEQ ID NO: 56)). The PCR assay of FIG. 8H utilizes a reverse orientation, anchored dT primer (FMR1_R_(CCG)nCCT) (FIG. 8H). This assay should produce a CE electropherogram with peaks of 14, 15, and 24 CGG size equivalents for the allele scenario represented in the top portion of the figure, in which the 46 repeat allele has two AGGs and the 97 repeat allele has one AGG, or the assay should produce a CE electropherogram with peaks of 15, 65, and 75 CGG size equivalents for the allele scenario represented in the bottom portion of the figure, in which the 46 repeat allele has no AGG and the 97 repeat allele has all three AGGs. The figure also shows the actual CE electropherogram (top right portion of figure) following the amplification of this genomic DNA sample. The electropherogram is consistent with the allele scenario shown in the top left portion of the figure.

Figure 15:
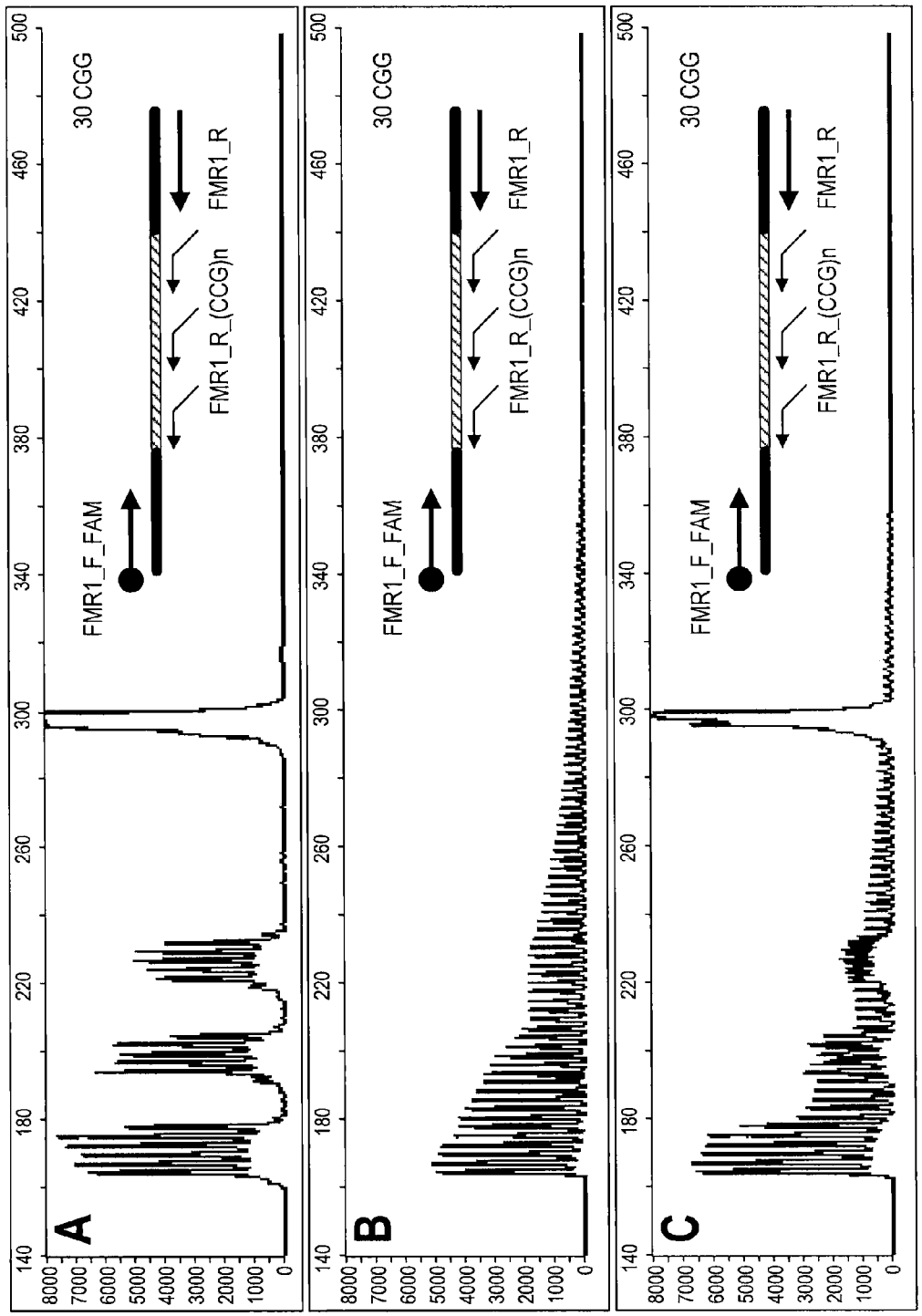

FIG. 15 depicts CE electropherograms following amplification of genomic DNA samples and mixed genomic DNA samples, according to the assay method of the invention shown in FIG. 8C. Two different DNA samples, one having a 30 CGG repeat allele (panel A) and another having a 645 CGG repeat allele (panel B) were analyzed separately. An artificial combination of chromosomal DNA from these two samples (panel C) was also analyzed to demonstrate that the method was able to map the presence or absence of AGG trinucleotides near the 5' end of long CGG repeats in the presence of a shorter allele having AGG trinucleotide inserts.

Figure 16:
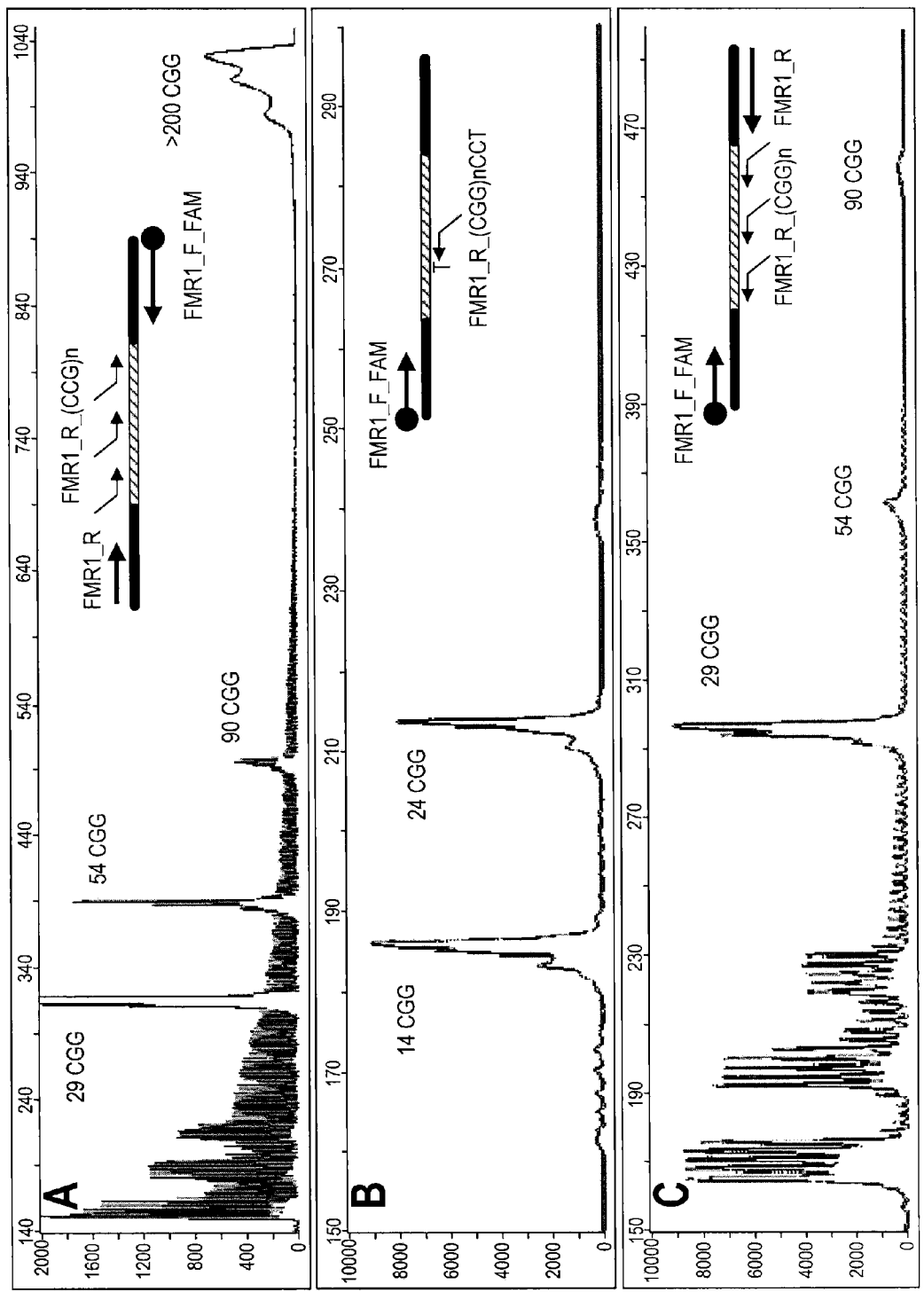

FIG. 16 shows CE electropherograms following amplification of chromosomal DNA from Sample 20 (Table 4). The sample has two major alleles, one of which is a full mutation allele, and two minor alleles. The allele configuration is believed to be derived from a mosaic population of cells within the sample. Panel A, amplification products following PCR amplification by the scheme shown in FIG. 8A. Panel B, amplification products following PCR amplification by the scheme shown in FIG. 8H. Panel C, amplification products following PCR amplification by the scheme shown in FIG. 8D. In addition to demonstrating the AGG/CGG mapping abilities of the assays, the data also demonstrate the presence of an AGG trinucleotide in a full mutation allele.

Figure 17:
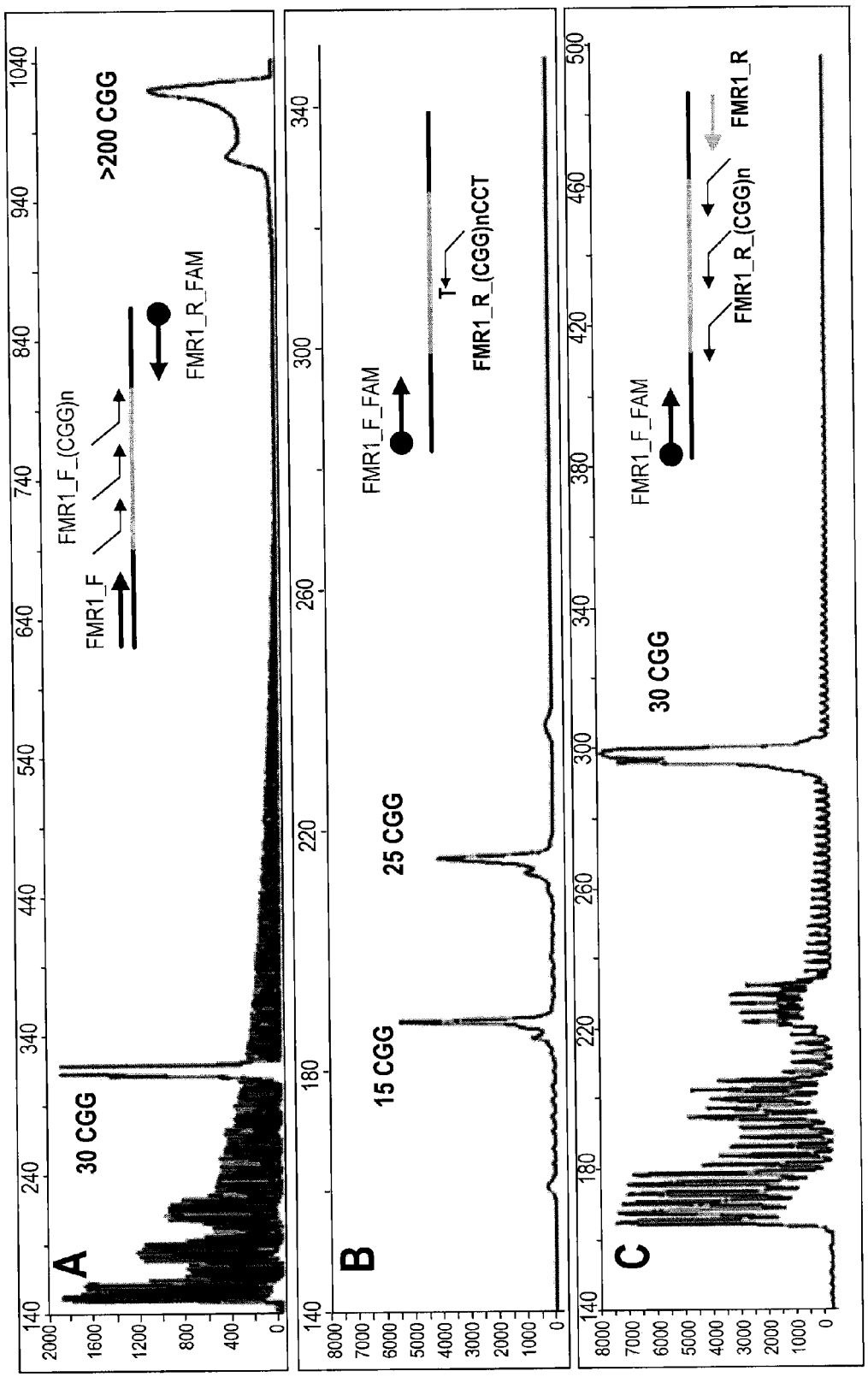

FIG. 17 shows CE electropherograms following amplification of chromosomal DNA from Sample 27 (Table 4). Panel A, amplification products following PCR amplification by the scheme shown in FIG. 8A. Panel B, amplification products following PCR amplification by the scheme shown in FIG. 8H. Panel C, amplification products following PCR amplification by the scheme shown in FIG. 8C. Note that Panel C is shown at a closer scale than Panel A, such that the region where the full-length peak would appear is not visible.

Figure 18:
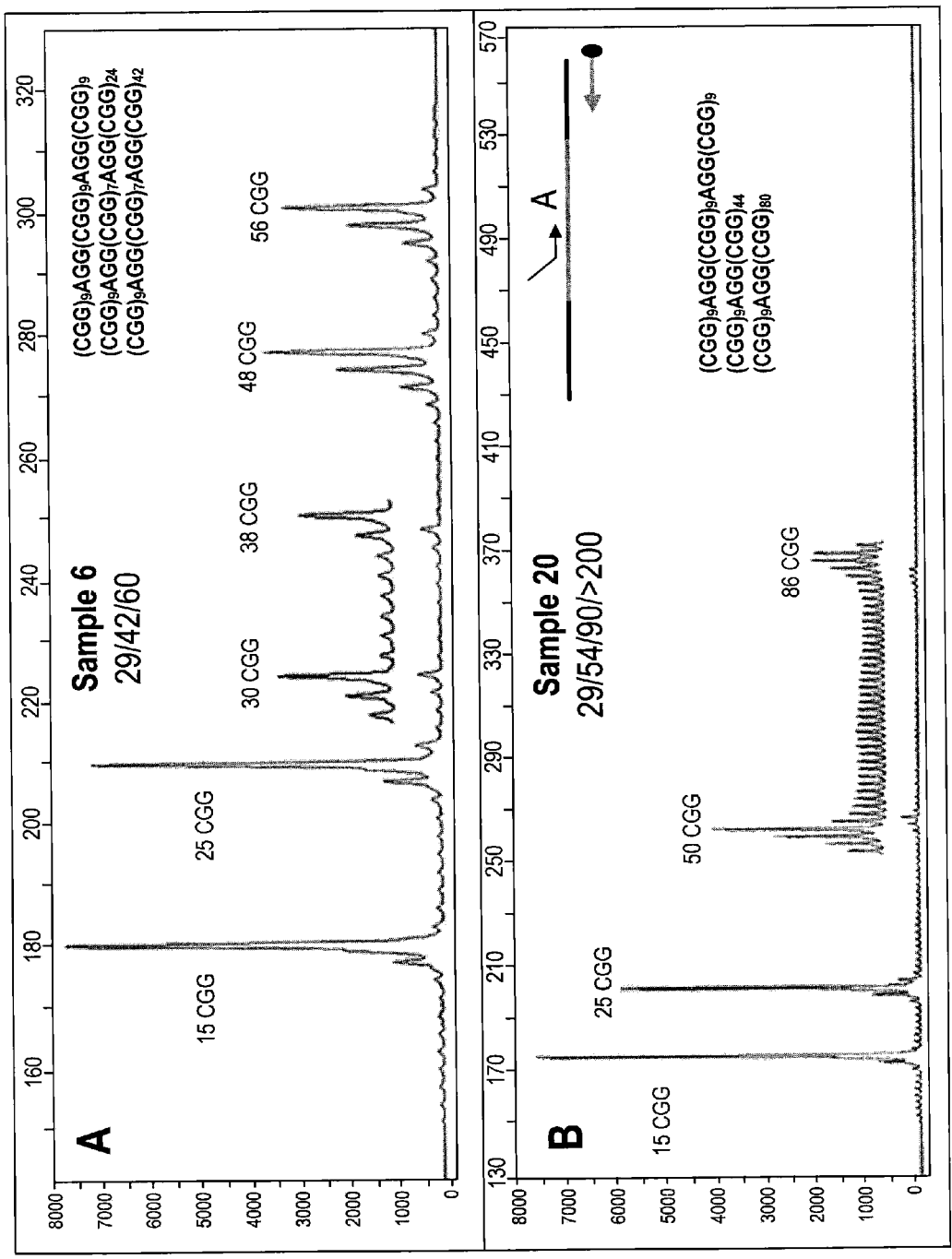

FIG. 18 shows CE electropherograms following amplification of chromosomal DNA from Samples 6 and 20 (Table 4). Panels A and B show amplification products from Samples 6 and 20 respectively, following PCR amplification by the scheme shown in FIG. 8F. As described in the Examples, the samples that were used to generate the profiles of panels A and B were determined to have mosaic CGG-repeat regions, composed of the following CGG-repeat sequences. Panel A: 5'-(CGG)$_9$AGG(CGG)$_9$AGG(CGG)$_9$-3' (SEQ ID NO:57), 5'-(CGG)$_9$AGG(CGG)$_7$AGG(CGG)$_{24}$-3' (SEQ ID NO:58) (minor allele), and 5'-(CGG)$_9$AGG(CGG)$_7$AGG(CGG)$_{42}$-3' (SEQ ID NO:59). Panel B: 5'-(CGG)$_9$AGG(CGG)$_9$AGG(CGG)$_9$-3' (SEQ ID NO:57), 5'-(CGG)$_9$AGG(CGG)$_{44}$-3' (SEQ ID NO: 60) and 5'-(CGG)$_9$AGG(CGG)$_{60}$-3' (SEQ ID NO: 61).

Figure 19:
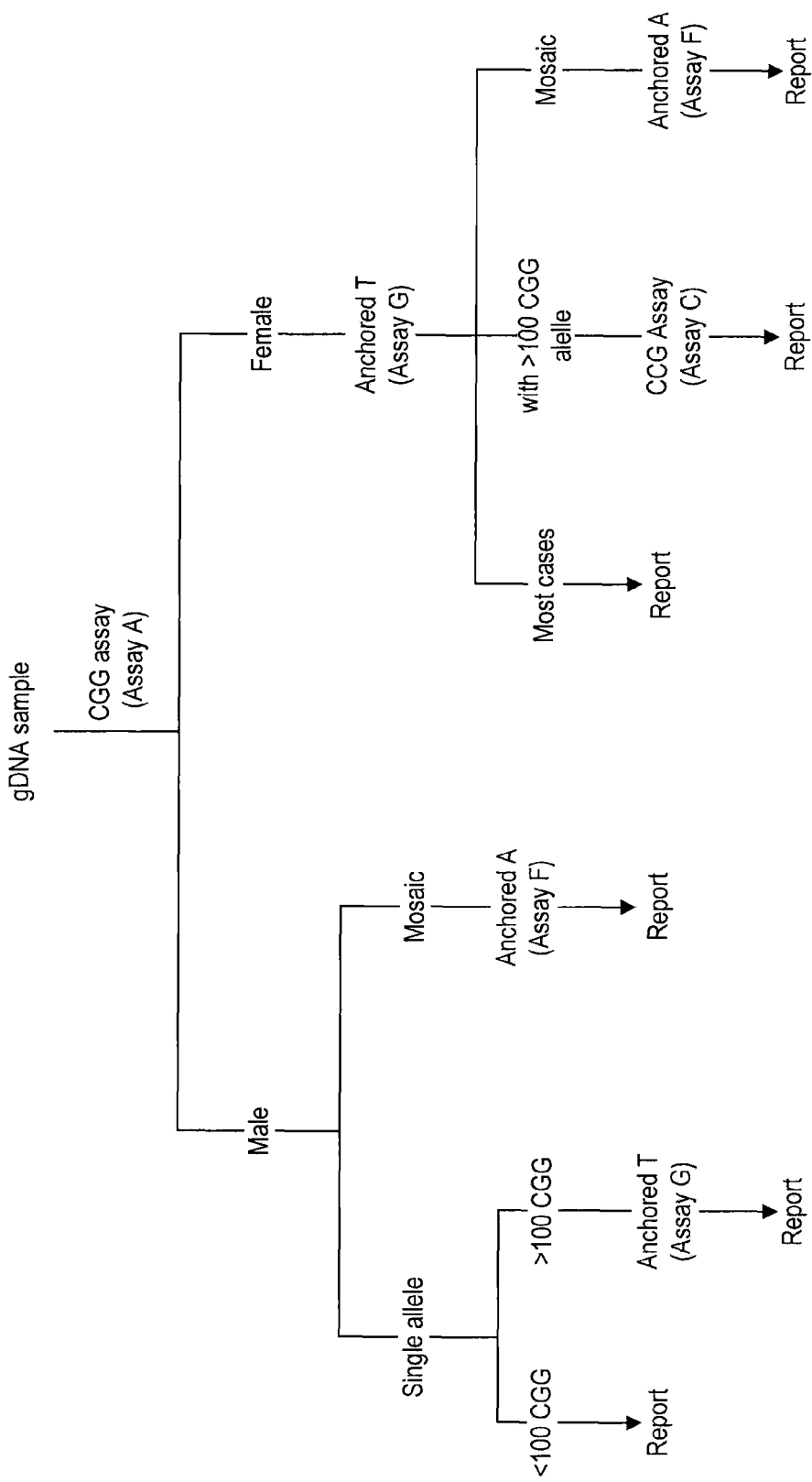

FIG. 19 represents a work flow for mapping AGG trinucleotides within CGG repeats in the 5' untranslated region of FMR1 and FMR2 genes. Assays A, C, G, and F refer to corresponding PCR assays shown in FIG. 8.

LISTING OF EXEMPLARY EMBODIMENTS

1. A method of analyzing at least one CGG-rich region comprised by at least one template in a sample, comprising:
   (a) providing at least two different primers, including a first primer comprising CGG, CCG, GCG, CGC, GCC, or GGC repeats, and a second primer that anneals to a position outside of the CGG-rich region;
   (b) performing PCR with the at least two different primers and the at least one template comprising the at least one CGG-rich region, wherein the PCR produces a set of products;
   (c) resolving the set of products with a high resolution technique to produce a representation of product size and abundance; and
   (d) deriving information about whether an interruptor sequence is present in the at least one CGG-rich region or where within the at least one CGG-rich region an interruptor sequence is located.

2. A method of analyzing at least one CGG-rich region comprised by at least one template in a sample, comprising:
   (a) providing at least three different primers, including a first primer comprising CGG, CCG, GCG, CGC, GCC, or GGC repeats and a 5' flap, a second primer that anneals to a position outside of the CGG-rich region, and a third primer having a sequence comprised by the 5' flap of the first primer, wherein the first primer is provided at a lower concentration than the third primer;
   (b) performing PCR with the at least three different primers and the at least one template, wherein the PCR produces a set of products;
   (c) resolving the set of products with a high resolution technique to produce a representation of product size and abundance; and
   (d) deriving information about whether an interruptor sequence is present in the at least one CGG-rich region or where within the at least one CGG-rich region an interruptor sequence is located from said representation.

3. The method of either of embodiments 1 or 2, comprising deriving information about whether an interruptor sequence is present in the CGG-rich region from said representation.

4. The method of either of embodiments 1 or 2, comprising deriving information about where within the CGG-rich region an interruptor sequence is located from said representation.

5. The method of either of embodiments 1 or 2, wherein the interruptor sequence is an AGG element.

6. The method of either of embodiments 1 or 2, further comprising deriving information about CGG repeat number from said representation.

7. The method of embodiment 6, wherein said information about CGG repeat number determines whether the CGG-rich repeat region comprises more or less than 200 CGG repeats.

8. The method of embodiment 6, wherein said information about CGG repeat number determines the number of CGG repeats present in the CGG-rich region.

9. The method of either of embodiments 1 or 2, with the proviso that an external standard or calibrator is not used in the deriving of information about whether an interruptor sequence is present in the CGG-rich region or where within the CGG-rich region an interruptor sequence is located from said representation.

10. The method of either of embodiments 1 or 2, wherein the CGG-rich region is comprised by a 5' UTR of FMR1.

11. The method of either of embodiments 1 or 2, wherein the CGG-rich region is comprised by a 5' UTR of FMR2.

12. The method of either of embodiments 1 or 2, wherein the high resolution technique can resolve products differing in length by 3 nucleotides or base pairs.

13. The method of either of embodiments 1 or 2, wherein the high resolution technique is capillary electrophoresis.

14. The method of either of embodiments 1 or 2, wherein the high resolution technique is polyacrylamide gel electrophoresis.

15. The method of either of embodiments 1 or 2, wherein the representation is an electropherogram.

16. The method of either of embodiments 1 or 2, wherein the representation is an image or graph recorded from photons or beta particles emitted by the products of the PCR or by dye molecules bound to the products.

17. The method of either of embodiments 1 or 2, wherein deriving information about whether an interruptor sequence is present in the CGG-rich region or where within the CGG-rich region an interruptor sequence is located from said representation comprises determining positions where binding of the first primer was substantially reduced.

18. The method of either of embodiments 1 or 2, wherein deriving information about whether an interruptor sequence is present in the CGG-rich region or where within the CGG-rich region an interruptor sequence is located from said representation comprises determining one or more product lengths at which the amount of product is substantially reduced compared to the amount of neighboring length products.

19. The method of either of embodiments 1 or 2, wherein deriving information about whether an interruptor sequence is present in the CGG-rich region or where within the CGG-rich region an interruptor sequence is located from said representation comprises determining one or more product lengths at which the amount of product is reduced by at least 50% compared to the amount of neighboring length products.

20. The method of either of embodiments 1 or 2, wherein deriving information about whether an interruptor sequence is present in the CGG-rich region or where within the CGG-rich region an interruptor sequence is located from said representation comprises determining one or more product lengths at which the amount of product is reduced by at least 90% compared to the amount of neighboring length products.

21. The method of either of embodiments 1 or 2, wherein deriving information about whether an interruptor sequence is present in the CGG-rich region or where within the CGG-rich region an interruptor sequence is located from said representation comprises determining one or more product lengths at which the amount of product is reduced by at least 25% compared to the amount of neighboring length products, wherein the CGG-rich region is from an individual heterozygous for the allele comprising the CGG-rich region.

22. The method of either of embodiments 1 or 2, wherein the first primer comprises four or five CGG or CCG repeats.

23. The method of either of embodiments 1 or 2, wherein the second primer is chosen from SEQ ID NOs 1-38.

24. The method of either of embodiments 1 or 2, wherein at least one of the primers comprises a radiologically or electromagnetically detectable moiety.

25. The method of either of embodiments 1 or 2, wherein at least one of the primers comprises a fluorophore.

26. The method of either of embodiments 1 or 2, wherein the method is an anchored assay.

27. The method of embodiment 26, wherein the first primer comprises a subsequence chosen from A, T, AG, CT, AGG, and CCT among or at the 3' end of the CGG, CCG, GCG, CGC, GCC, or GGC repeats.

28. The method of embodiment 27, wherein the first primer comprises an A at the 3' end of the CGG, CCG, GCG, CGC, GCC, or GGC repeats.

29. The method of embodiment 27, wherein the first primer comprises a CCT at the 3' end of the CGG, CCG, GCG, CGC, GCC, or GGC repeats.

30. The method of embodiment 26, further comprising detecting at least one interruptor element comprised by the at least one CGG-rich region.

31. The method of embodiment 30, further comprising determining whether the sample comprises major and minor alleles with differently positioned interruptor elements.

32. The method of either of embodiments 1 or 2, wherein the method is a non-anchored assay.

33. The method of embodiment 2, wherein the first primer and third primer are provided at concentrations such that the third primer is at least 100-fold more abundant than the first primer by molarity.

34. The method of embodiment 2, wherein the first primer and third primer are provided at concentrations such that the third primer is at least 500-fold more abundant than the first primer by molarity.

35. The method of embodiment 2, wherein the first primer and third primer are provided at concentrations such that the third primer is at least 900-fold more abundant than the first primer by molarity.

36. The method of embodiment 2, wherein the second primer anneals downstream of the CGG-rich region, and the third primer anneals upstream of the CGG-rich region.

37. The method of embodiment 2, wherein the second primer anneals upstream of the CGG-rich region, and the third primer anneals downstream of the CGG-rich region.

38. The method of either of embodiments 1 or 2, further comprising providing at least a first additional primer and optionally a second additional primer, the first additional primer comprising CGG, CCG, GCG, CGC, GCC, or GGC repeats; performing a second PCR with at least the first additional primer, a primer chosen from the second primer of step (a) and the second additional primer, and the at least one template, wherein the second PCR produces a second set of products; and resolving the second set of products with a high resolution technique to produce a second representation of product size and abundance;

wherein the first primer of step (a) has a preferential binding activity for sites in the CGG rich region that do not comprise an interruptor element, and wherein the first additional primer has a preferential binding activity for sites in the CGG rich region that comprise an interruptor element.

39. The method of embodiment 38, wherein the first additional primer comprises an A at the 3' end of the CGG, CCG, GCG, CGC, GCC, or GGC repeats.

40. The method of embodiment 38, wherein the first additional primer comprises a T at the 3' end of the CGG, CCG, GCG, CGC, GCC, or GGC repeats.

41. The method of embodiment 38, further comprising determining at least one length of the at least one CGG-rich region.

42. The method of embodiment 41, wherein the sample comprises genetic material from cells having a ploidy of at least 2 with respect to the CGG region, and the method comprises determining at least two lengths of at least two CGG-rich regions.

43. The method of embodiment 41, wherein the sample comprises an allele comprising a CGG-rich region comprising at least 100 CGG repeats.

44. The method of embodiment 38, further comprising determining whether the sample comprises major and minor alleles with differently positioned interruptor elements.

45. The method of embodiment 38, wherein the first additional primer is oppositely oriented relative to the first primer.

46. The method of embodiment 45, wherein the first primer binds the CGG-rich region with its 3' end oriented downstream, and the first additional primer binds the CGG-rich region with its 3' end oriented upstream.

47. The method of embodiment 46, wherein the method comprises detecting at least one interruptor element and determining the size of the CGG-rich region comprising the at least one interruptor element.

48. The method of embodiment 47, wherein the sample comprises at least first and second alleles, and the first and second alleles comprise CGG-rich regions of different lengths.

49. The method of embodiment 38, further comprising providing at least a third additional primer and optionally a fourth additional primer, the third additional primer comprising CGG, CCG, GCG, CGC, GCC, or GGC repeats; performing a third PCR with at least the third additional primer, a primer chosen from the second additional primer and the fourth additional primer, and the at least one template, wherein the third PCR produces a third set of products; and resolving the third set of products with a high resolution technique to produce a third representation of product size and abundance;

wherein the third additional primer is oppositely oriented relative to the first primer of step (a) and is different from the first additional primer.

50. The method of embodiment 49, further comprising determining the presence or absence of interruptor elements within 150 by of either end of at least one allele comprised by the sample.

51. The method of embodiment 50, further comprising determining at least one position of at least one interruptor element comprised by the at least one allele.

52. The method of either of embodiments 1 or 2, further comprising providing at least a first additional primer and a second additional primer, the first additional primer comprising CGG, CCG, GCG, CGC, GCC, or GGC repeats; performing a second PCR with at least the first additional primer and the second additional primer, and the at least one template, wherein the second PCR produces a second set of products; and resolving the second set of products with a high resolution technique to produce a second representation of product size and abundance;

wherein the first additional primer is oppositely oriented to the first primer of step (a).

53. The method of embodiment 52, wherein at least one of the first primer and the first additional primer has a preferential binding activity for sites in the CGG rich region that do not comprise interruptor elements.

54. The method of embodiment 53, wherein the first primer has a preferential binding activity for sites in the CGG rich region that do not comprise interruptor elements, and the first additional primer has a preferential binding activity for sites in the CGG rich region that comprise interruptor elements.

55. The method of embodiment 54, wherein the sample comprises at least two alleles comprising CGG-rich regions of different lengths, further comprising determining the lengths of the at least two alleles.

56. The method of embodiment 55, further comprising detecting at least one interruptor element and determining the length of the allele by which the at least one interruptor element is comprised.

57. A method of analyzing at least one CGG-rich region comprised by at least one template in a sample, comprising:

(a) providing at least two different primers, wherein the first primer comprises CGG, CCG, GCG, CGC, GCC, or GGC repeats and the second primer anneals to a position outside of the CGG-rich region;

(b) performing PCR with the at least two different primers and a template comprising the CGG-rich region, wherein the PCR produces a set of products;

(c) resolving the set of products with a high resolution technique to produce a representation of product size and abundance in which products differing in length by three nucleotides are resolved; and (d) deriving information about CGG repeat number from said representation.

58. A method of analyzing at least one CGG-rich region comprised by at least one template in a sample, comprising:

(a) providing three different primers, wherein the first primer comprises CGG, CCG, GCG, CGC, GCC, or GGC repeats and a 5' flap, the second primer anneals to a position outside of the CGG-rich region, the third primer has the same sequence of the 5' flap of the first primer, and the first primer is provided at a lower concentration than the third primer;

(b) performing PCR with the three different primers and a template comprising the CGG-rich region, wherein the PCR produces a set of products;

(c) resolving the set of products with a high resolution technique to produce a representation of product size and abundance in which products differing in length by three nucleotides are resolved; and (d) deriving information about CGG repeat number from said representation.

59. The method of either of embodiments 57 or 58, wherein said information about CGG repeat number determines whether the CGG-rich repeat region comprises more or less than 200 CGG repeats.

60. The method of either of embodiments 57 or 58, wherein said information determines the number of CGG repeats present in the CGG-rich region.

61. The method of either of embodiments 57 or 58, with the proviso that an external standard or calibrator is not used in the deriving of information about CGG repeat number.

62. The method of either of embodiments 57 or 58, wherein the CGG-rich region is comprised by a 5' UTR of FMR1.

63. The method of either of embodiments 57 or 58, wherein the CGG-rich region is comprised by a 5' UTR of FMR2.

64. The method of either of embodiments 57 or 58, wherein the high resolution technique can resolve products differing in length by 3 nucleotides or base pairs.

65. The method of either of embodiments 57 or 58, wherein the high resolution technique is capillary electrophoresis.

66. The method of either of embodiments 57 or 58, wherein the high resolution technique is polyacrylamide gel electrophoresis.

67. The method of either of embodiments 57 or 58, wherein the representation is an electropherogram.

68. The method of either of embodiments 57 or 58, wherein the representation is an image or graph recorded from photons or beta particles emitted by the products of the PCR or by dye molecules bound to the products.

69. The method of either of embodiments 57 or 58, wherein the first primer comprises four or five CGG or CCG repeats.

70. The method of either of embodiments 57 or 58, wherein the second primer is chosen from SEQ ID NOs 1-38.

71. The method of either of embodiments 57 or 58, wherein at least one of the primers comprises a radiologically or electromagnetically detectable moiety.

72. The method of either of embodiments 57 or 58, wherein at least one of the primers comprises a fluorophore.

73. The method of embodiment 58, wherein the first primer and third primer are provided at concentrations such that the third primer is at least 100-fold more abundant than the first primer by molarity.

74. The method of embodiment 58, wherein the first primer and third primer are provided at concentrations such that the third primer is at least 500-fold more abundant than the first primer by molarity.

75. The method of embodiment 58, wherein the first primer and third primer are provided at concentrations such that the third primer is at least 900-fold more abundant than the first primer by molarity.

76. The method of embodiment 58, wherein the second primer anneals downstream of the CGG-rich region, and the third primer anneals upstream of the CGG-rich region.

77. The method of embodiment 58, wherein the second primer anneals upstream of the CGG-rich region, and the third primer anneals downstream of the CGG-rich region.

78. An oligonucleotide comprising a sequence chosen from SEQ ID NO:44 and SEQ ID NO:45.

EXAMPLES

Reference will now be made in detail to embodiments of the invention, aspects and results of which are illustrated in the accompanying drawings. For purposes of clarity and continuity, several segments of discussion and interpretation of the methods and results of certain examples are provided immediately thereafter; the presentation of examples resumes following these segments.

Example 1

Determination of CGG Repeat Number and AGG Position in the FMR1 Promoter for Normal and Low Premutation Alleles by a Repeat-Primed PCR Assay and High Resolution Capillary Electrophoresis Eight genomic DNA samples containing normal to low premutation numbers of CGG repeats (5 clinic samples: AFM104, AFB107, ABB001, AFB011, and AMB12; and three Coriell standards: 31/46 CGG, 31/54 CGG, and 30/75 CGG) were evaluated as follows. Primers used were SEQ ID NOs: 38-39. The PCR reaction conditions that were used were based on a published protocol (Saluto et al., *J. Mol. Diagn.* 7: 605-12 (2005)) with slight modifications. 15 to 20 ng of genomic DNA were amplified in a reaction buffer containing Roche Expand Long Template PCR buffer 2 (Roche Cat. No. 11681834001) plus 2.2 M betaine (Sigma Cat. No. B0300-1VL), 250 µM each dNTP (Roche, GMP Grade Cat. No. G 04631129103, C 04631072103, A 04631056103, T 04631137103), 1.5 µM of each primer, and 1.25 U of Roche GMA recombinant Taq DNA polymerase (Roche, Cat. No. 03734935001), in a 15 µl reaction volume. The PCR cycling conditions were 95° C. for 5 min; then 10 cycles of 97° C. for 35 sec—62° C. for 35 sec—68° C. for 4 min; then 20 cycles of 97° C. for 35 sec—62° C. for 35 sec—68° C. for 4 min with 20 sec auto-extension per cycle. 1 µl of PCR products were mixed with 2 µl of ROX 1007 ladder (prepared according to DeWoody et al., *Biotechniques* 37:348, 350, 352 (2004)) in 12 µl Hi-Di™ Formamide (Applied Biosystems (ABI) part no. 4311320) and heat denatured at 95° C. for 2 min before capillary electrophoresis on an ABI 3130xl instrument with 36 cm capillary length using POP7 liquid polymer (ABI part no. 4352759). The resulting electropherograms are shown in FIGS. 2A and 2B.

Peaks in the electropherograms were numbered starting with 4, the minimum possible product CGG content. A severe reduction in peak intensity from peak n to n+1, e.g., from peak 10 to 11, was indicative of the presence of an AGG trinucleotide at the position corresponding to peak n+1. One trinucleotide resulted in four low intensity peaks, believed to be because the AGG trinucleotide reduced the CGG-containing primer affinity for all four binding positions encompassing that trinucleotide (recall that the primer, with the sequence of SEQ ID NO: 39, contained four CGG repeats). The total number of trinucleotides was determined by counting the total number of peaks, with the first being numbered 4 as described above. The small peak at the right of each panel of FIG. 2A and in the top left panel of FIG. 2B is believed to result from annealing events wherein only 3 CGG repeats of the primer and template are annealed, and so does not reflect actual template length. Total repeat content and AGG trinucleotide repeat locations were confirmed by sequencing the five clinical samples (see Table 1) by standard techniques. For all five clinical samples, the results obtained through the disclosed method agreed with the results obtained via sequencing.

TABLE 1

| Sample ID | Source | CGG# | Sequencing determined AGG position | Repeat PCR determined AGG position | Repeat PCR determined CGG# |
|---|---|---|---|---|---|
| AFM104 | Asuragen donor#4 mouth wash | 30/30 | 11, 21 | 11, 21 | 30 |
| AFB107 | Asuragen#7 donor blood | 30/30 | 11, 21 | 11, 21 | 30 |
| AMB001 | Asuragen#1 donor blood | 29 | 10, 20 | 10, 20 | 29 |
| AMB011 | Asuragen#11 donor blood | 29 | 10, 20 | 10, 20 | 29 |
| AMB012 | Asuragen#12 donor blood | 37 | 10, 18, 28 | 10, 18, 28 | 37 |
| NA20234 | Coriell | 31 | N/A | | 31 |
| | | 46 | N/A | | 46 |
| NA20236 | Coriell | 31 | N/A | | 31 |
| | | 54 | N/A | | 54 |
| NA20242 | Coriell | 30 | N/A | | 30 |
| | | 73 | N/A | | 75 |

Example 2

Difficulty of Determining Repeat Number and Position in Some Long Alleles from Female Samples with Two Primer Repeat-Primed PCR Assay To evaluate this assay with samples comprising CGG repeats from the normal to full mutation range, another set of eight samples, namely two whole blood clinical samples (Sample IDs 00100 and 00065, corresponding to the panels of FIG. 3 labeled 69 CGG and 87 CGG) and six Coriell cell line genomic DNA samples (with Coriell designations indicating 56, 76, 96, 118, 20/183-193 and 28/336 CGG), were tested. The PCR reactions were performed as described in Example 1. The resulting electropherograms are shown in FIGS. 3A-3B. In these electropherograms, the final peak to be counted was determined by visual inspection. For all six samples from males (all panels of FIG. 3A and the top two panels of FIG. 3B), this assay was able to determine both the size (repeat number) and the position of AGG trinucleotides (see table 2). The repeat numbers agreed with the Coriell designations or the number obtained through sequencing to within 4%. The assay was not able to detect the full number of repeats present in the longer alleles of the female samples (bottom panels of FIG. 3B).

TABLE 2

| Sample ID | Source | CGG# | Sequencing determined AGG position | Repeat PCR determined AGG position | Repeat PCR determined CGG# |
|---|---|---|---|---|---|
| CD00014 | Coriell cell line | 56 | 11, 21 | 11, 21 | 57 |
| 00100 | Blood | 69 | N/A | No AGG | 69 |
| NA20231 | Coriell cell line | 76 | 11 | 11 | 78 |
| 00065 | Blood | 87 | N/A | No AGG | 87 |
| NA06906 | Coriell cell line | 96 | 11 | 11 | 100 |
| NA06891 | Coriell cell line | 118 | 11 | 11 | 122 |
| NA20239 | Coriell cell line | 20/182-193 | N/A | 11 (20 CGG) | 20/>60 |
| NA07537 | Coriell cell line | 28/336 | N/A | 10, 20 (29 CGG) | 29 > 50 |

Example 3

Determination of CGG Repeat Number and AGG Position in High Premutation and Full Mutation Alleles Using Modified Three Primer System for Repeat-Primed PCR To increase the number of repeats that could be detected, the procedure was modified as outlined in FIG. 4. Three primers were used. The first primer was a chimeric primer that contained 5 CGG repeats at the 3' end and had the sequence of SEQ ID NO: 41. The second primer was a reverse primer relative to the first primer; this second primer had the sequence of SEQ ID NO: 37. The third primer was oriented forward with respect to the chimeric primer and had the same sequence as the chimeric primer but without the 5 CGG repeats. The chimeric primer was provided at a concentration, 1.5 nM, approximately 1000 fold below that of the second and third primers (each at 1.5 µM), such that the chimeric primer would be depleted within the first few PCR cycles. The other conditions were as in Example 1. This procedure, performed with templates as indicated in FIG. 5, resulted in products being obtained that had up to approximately 196-199 repeats in the experiment represented by the top panel. This value was close to, but slightly higher than, the Coriell designation of 183-193 CGG repeats. In the experiment represented by the bottom panel, a peak was observed far to the right of the electropherogram, labeled 336 CGG repeats according to the Coriell designation. The apparent repeat number was between 250-300 repeats, but this apparent size was not considered precise because the size of this product is not thought to be within the range wherein POP-7 polymer-based CE can resolve CGG-repeat containing products accurately according to size. With POP-7 polymer-based CE, products containing more than about 200 CGG repeats tend to have artificially shortened apparent sizes. Thus, this result indicated that the peak represented a product with a repeat number not smaller than 250. In both panels, peaks were observed at the approximate expected position for a product with the repeat number indicated by the shorter alleles listed in the Coriell designations, these designations being 20 for the top panel, and 28 for the bottom panel (the large peak shown in this panel corresponded to a repeat number of 29). In each panel, the peak corresponding to the longer allele (Coriell-designated repeat numbers 183-193 and 336) was broader than the peaks for individual repeat number-containing products. The width of the 183-193 CGG peak in the top panel of FIG. 5 appeared to be approximately 5-10 CGG repeats or 15-30 bp. Note that the leftmost peak in each electropherogram of FIG. 5 corresponded to 5 CGG, due to the chimeric primer containing 5 CGG repeats.

Example 4

Determination of AGG Location within CGG Repeats of the FMR1 Promoter in Male Alleles by a Modified Three Primer System for Repeat-Primed PCR Five genomic DNA samples containing alleles with numbers of CGG repeats in the normal to low pre-mutation range (30 CGG, 47 CGG, 61 CGG, 20/31 CGG and 46/97 CGG) were evaluated. For brevity, the numbers of CGG repeats listed reflect the total number of trinucleotides, that is, sum of the number of CGG trinucleotides and the number of interrupting AGG trinucleotides. Samples were PCR amplified by preparing a master mix containing 11.45 µl GC-Rich AMP buffer (Asuragen Cat. No. #49387), 1.5 µl of FAM-labeled FMR1 Primers (Asuragen Cat. No. #49386; FMR1_F (SEQ. ID NO: 14), FMR1_R_FAM (SEQ. ID NO: 37 having a 5'FAM)), 0.5 µl FMR1_F_(CGG)n (SEQ. ID NO: 41) (Asuragen Cat. No. #49393), 0.5 µl nuclease-free water, and 0.05 µl GC-rich Polymerase Mix (Asuragen Cat. No. #49388) from Asuragen Inc. (Austin, Tex., USA). The PCR master mix was vortexed prior to dispensing to a microtiter plate (96- or 384-well plates, Phenix Research Products, Candler, N.C., USA). The final reaction concentrations of FMR_F and FMR_R_FAM were 1.3 µM, and the final reaction concentration of FMR1_F_(CGG)n was 1.3 nM. Aliquots of the genomic DNA samples, typically 1 µl at 20 ng/µl, were transferred to each well of the microtiter plate. ABgene aluminum film sheets (Thermo Fisher Scientific) were used to seal the plates. Sealed plates were vortexed, centrifuged, and transferred to a thermal cycler (GeneAmp® PCR System 9700, Applied Biosystems™, Foster City, Calif., USA). Samples were amplified with an initial heat denaturation step of 95° C. for 5 min, followed by 10 cycles of 97° C. for 35 sec, 62° C. for 35 sec, 68° C. for 4 min and then 20 cycles of 97° C. for 35 sec, 62° C. for 35 sec and 68° C. for 4 min with a 20 second auto extension at each cycle. The final extension step was 72° C. for 10 min. This three primer system for assaying CGG repeats is depicted schematically in FIG. 4 and FIG. 8A.

After PCR, samples were stored at −15 to −30° C. (protected from light prior to analysis) or used immediately for amplification product analysis by capillary electrophoresis (CE). For CE, PCR products (1 µl) were mixed with 2 µl of ROX 1007 ladder (prepared according to DeWoody et al., Biotechniques 37:348, 350, 352 (2004)) in 12 µl Hi-Di™ Formamide (Applied Biosystems™ part no. 4311320) and heat denatured at 95° C. for 2 min before capillary electrophoresis on an Applied Biosystems™ 3130xl instrument with 36 cm capillary length using POP7 liquid polymer (Applied Biosystems™ part no. 4352759). The resulting electropherograms are shown in FIG. 6.

Peaks in the electropherograms were numbered starting with 5, the minimum possible CGG repeat content of PCR products, based on the chimeric primer design. A severe reduction in peak intensity from peak n to n+1 (e.g., in FIG. 6 panel A from peak 9 to 10,) was indicative of the presence of an AGG trinucleotide at the position corresponding to peak n+1. One AGG trinucleotide resulted in five low intensity peaks, believed to be because the AGG trinucleotide reduced the binding affinity of the CGG-containing primer for all five binding positions encompassing that trinucleotide (recall that the primer, with the sequence of SEQ ID NO: 41, contained five CGG repeats). The total number of CGG/AGG trinucleotides was determined by counting the total number of peaks, with the first being numbered 5 as described above. For example, the electropherogram in FIG. 6 panel A profiles products amplified from a normal male, hemizygous template with 30 CGG/AGG repeats. Three sets of well defined peaks were apparent at the left side of the trace, corresponding to the products of the CGG repeat primer. The leftmost peak corresponded to products with 5 CGG since the chimeric primer is comprised of 5 complementary CGG repeats. The gap between the first 5 peaks and the next set of 5 most intense peaks reflected interference by an intervening AGG sequence. This gap was equivalent to 5 CGG repeats, that is, the span of the chimeric primer as it interrogates each possible position for hybridization (which is, in turn, compromised at each repeat unit in the primer by mismatches between the "C" of the CGG primer repeat and the "T" within the reverse complement (CCT) of the AGG interruptor sequence). The next set of 5 peaks reflected a marked increase in signal intensity as the chimeric primer bound to sites beyond the interrupting AGG sequence. A second AGG element was then encountered, and after primer extension across the last set of CGG sequences, the CGG product signal was lost altogether. The CE data indicated the presence of 30 CGG/AGG repeats in this allele. Following the repeat amplicons, a gap in the electropherogram was observed, and the rightmost peak was a very intense product band corresponding to the full length amplicon, produced from the FMR1-F and the FMR1R-FAM primers, that encompassed the 30 CGG/AGG tract. This CE profile corresponded to a 5'-$(CGG)_{10}AGG(CGG)_9AGG(CGG)_9$-3' (SEQ ID NO:46) sequence.

Four additional examples of PCR product profiles were obtained from FMR1 alleles (FIG. 6, panels B-E). Samples from males are represented in panels B and C, and samples from females in panels D and E. In each case, the gene-specific peak was sized in comparison to a DNA reference (i.e., the ROX ladder). This sizing was in agreement with the calibration-free method of CGG product peak counting described above. The accuracy of CGG quantification using this approach was also well correlated to the results of Wilson et al., (*J Mol Diagn* 10:2-12, 2008) using published fragile X consensus materials. Using the same analysis strategy, samples B and C were decoded as $(CGG)_9AGG(CGG)_9AGG(CGG)_{27}$ (SEQ ID NO:47) and $(CGG)_{61}$ (SEQ ID NO:48) (no AGG), respectively.

Discussion of Possible Interpretations of Results in FIGS. 6D-E, and Reflex Assays for Distinguishing them Results with genomic DNA samples from females can be more complex to interpret. For example, the sample results presented in FIG. 6 panels D and E revealed a combination of medium and high intensity peaks. This product pattern reflected the overlap of two populations of CGG repeat products, one from each allele. The AGG positions can be determined from the position of the two signal "dips" (i.e., reductions in peak signal intensity) in the heterozygous profile. The only difference from the profiles of the male hemizygous alleles is that the signal intensity in the "dip" may never reduce to near baseline in the female sample, because in these cases, the two female alleles did not have AGG trinucleotides at the same position relative to the 3' end of the amplicon. For the sample shown in panel D (20/31 CGG allele), the first AGG signal intensity "dip", between peaks 10 and 16, never reduced to baseline, because only one allele had an AGG trinucleotide at that position, while the other had a CGG trinucleotide. In contrast, the second signal dip returned to baseline because the 20 CGG allele ends at position 20 and the second AGG dip along with the downstream CGG peaks in the electropherogram belonged to the 31 CGG allele only. The only ambiguity here was which of the two alleles had the AGG trinucleotide identified by the first signal dip. Based on the incidence of known AGG haplotypes, the most likely case is that the very short allele (20 CGG) does not contain the AGG while the 31 CGG allele has two AGGs (as shown by the sequences in panel D). The standard, three primer CGG repeat-primed assay alone, however, cannot definitely report which allele contributes to the first AGG dip.

Analysis of the next sample (FIG. 6, panel E) was more complex. The CE trace showed three apparent AGG dips (unlabeled arrows). Using the most likely scenario based on haplotype statistics, the two AGG dips on the left side of the CE trace would be assigned to the 46 repeat allele and the third AGG dip (rightmost unlabeled arrow) would be assigned to the 97 repeat allele. As a result, the allele sequences would be $(CGG)_9AGG(CGG)_9AGG(CGG)_{26}$ and $(CGG)_{10}AGG(CGG)_{86}$. However, two uncertainties exist in this sequence. First, each of the AGG trinucleotides identified by the signal dips, in theory, can be assigned to either of the two alleles. If all three AGG trinucleotides occur in the 97 repeat allele, and none in the 46 CGG repeat allele, the sequences deduced from the electropherogram trace would be $(CGG)_{46}$ and $(CGG)_9AGG(CGG)_{60}AGG(CGG)_9AGG(CGG)_{26}$. This sequence combination would generate the identical CE profile as the one described above. Second, the full length gene specific peak of the 46 repeat allele (the very high intensity peak near the middle of the CE trace) may overlap with and obscure any AGG dip in the 97 repeat allele. Thus, there may be an additional AGG signal dip within the 97 repeat allele that migrates at the same position on the CE electropherogram as the full length gene specific 46 allele.

Additional methods were developed to differentiate the specific AGG mapping possibilities for the 20/31 CGG and 46/97 CGG alleles shown in Example 4 (FIG. 6 panels D and E). Example 5 below demonstrates the utility the methods of the invention for accurately resolving these uncertainties.

For the 20/31 allele sample (FIG. 6 panel D), two possible AGG assignments to the 20 and 31 repeat alleles are shown in FIG. 7 (left panels). Both scenarios are predicted to result in identical CE electropherograms when PCR amplification products are separated by CE (simulated in FIG. 7, bottom right panel). The simulated CE profile of the two possible allele configurations (FIG. 7, bottom right panel) was in agreement with the empirical CE results (FIG. 7, top right panel).

Although the standard three primer CGG repeat-primed assay (FIG. 4, FIG. 8A) was unable to distinguish the AGG status of the two alleles, a reflex assay, depicted schematically in FIG. 8H, was developed that could distinguish between the two possible allele scenarios, as shown in FIG. 9. Using the PCR assay shown in FIG. 8H, a CE electropherogram for the first allele scenario (i.e., each allele has one AGG; FIG. 9, top) would generate two adjacent peaks with 14 CGG and 15 CGG size equivalents. A CE electropherogram for the second allele scenario, in which the shorter 20 repeat allele has no CGG and the 31 repeat allele has two AGGs (FIG. 9, bottom), would generate peaks with 15 CGG and 25 CGG size equivalents. In another example (FIG. 6, panel E), the specimen contained two alleles having 46 and 97 CGG repeats. As mentioned above, the standard three primer CGG repeat-primed assay (FIG. 4, FIG. 8A) could not differentiate the AGG content of the specific alleles. Simulation CE electropherograms of allele amplification products for this sample are shown in FIG. 10. The left and right bottom panels of FIG. 10 reveal that the three primer CGG repeat-primed PCR assay is unable to resolve the two possible allele configurations. However, when using a PCR assay (FIG. 8C) in which the directionality of the repeat primer is reversed (FMR1_R_(CCG)n; SEQ ID NO: 43), the two allele scenarios are predicted to generate different CE profiles as shown in FIG. 11, bottom panels.

Example 5

PCR Assays for Determining AGG Location Within CGG Repeats of the FMR1 Promoter in Complex Female Alleles PCR and CE conditions were used in a reflex assay of the 20/31 CGG sample of FIG. 6D that were identical to those described in Example 4 above except that different primers were used. The forward primer sequence was FMR1_F_FAM (SEQ ID NO:14) and the reverse primer was an anchored primer having a 3' terminal dT (FIG. 8H, FMR_R_(CCG)nCCT, where n=4; SEQ ID NO: 45). The actual CE profile for the sample contained 15 and 25 CGG peaks (FIG. 9, CE trace) confirming that the two allele sequences were (CGG)$_{20}$ (SEQ ID NO: 49) and (CGG)$_{10}$AGG(CGG)$_9$AGG(CGG)$_{10}$ (SEQ ID NO: 50).

When a PCR assay was performed on the 46/97 CGG sample of FIG. 6E with a two primer repeat-primed design, depicted schematically in FIG. 8B, only three AGG dips were present in the CE profile (FIG. 12, top panel B, unlabeled arrows). These data excluded the possibility of a 4$^{th}$ AGG dip that would have been overlapped by the gene-specific peak of the 46-repeat allele (FIG. 6E). Also, when the anchored PCR assay depicted schematically in FIG. 8F was performed, three distinct CGG allele peaks, at the 32, 42, and 92 CGG repeat positions were observed (FIG. 12, bottom panel F). This result clearly confirmed that only 3 AGGs were present in the two alleles.

Discussion

However, neither of these two assays (FIG. 8B, 8F) could definitively assign the number of AGG elements present in each allele. FIG. 13 explains why this is so—the anchored A primer assay (FMR1_F_(CGG)nA; SEQ ID NO: 44), shown in FIG. 8F and FIG. 13, would generate identical CE results for allele scenario (1) in which the 46 repeat allele has two AGGs and the 97 repeat allele has one AGG (FIG. 13, top schematic), and for allele scenario (2) in which the 46 repeat allele has no AGG and the 97 repeat allele has all three AGGs (FIG. 13, bottom schematic). However, each AGG can be assigned accurately to the appropriate allele using an assay where the directionality of the CGG primer is reversed. As shown in FIG. 14, a PCR assay that utilizes a reverse orientation, anchored dT primer (FMR1_R_(CCG)nCCT; SEQ ID NO: 45) (FIG. 8H, FIG. 14) should produce a CE electropherogram with peaks of 14, 24, and 15 CGG size equivalents for allele scenario (1) or a CE electropherogram with peaks of 15, 65, and 75 CGG size equivalents for allele scenario (2). Table 3 lists all the possible AGG distributions in the two alleles, along with the expected CGG peak size after CE separation of PCR amplification products from this anchored dT primed assay (FIG. 8H).

TABLE 3

| CE Peaks (CGG Repeat Equivalents) | AGG position in 46 allele | AGG position in 97 allele |
|---|---|---|
| 15, 14, 24 CGG | (CGG)$_9$AGG(CGG)$_9$AGG(CGG)$_{26}$ (SEQ ID NO: 51) | (CGG)$_{10}$AGG(CGG)$_{86}$ (SEQ ID NO: 52) |
| 15, 65, 24 CGG | (CGG)$_{19}$AGG(CGG)$_{26}$ (SEQ ID NO: 68) | (CGG)$_{10}$AGG(CGG)$_{49}$AGG(CGG)$_{36}$ (SEQ ID NO: 69) |
| 15, 14, 75 CGG | (CGG)$_9$AGG(CGG)$_{36}$ (SEQ ID NO: 70) | (CGG)$_{10}$AGG(CGG)$_{59}$AGG(CGG)$_{26}$ (SEQ ID NO: 71) |
| 15, 65, 75 CGG | (CGG)$_{46}$ (SEQ ID NO: 55) | (CGG)$_{10}$AGG(CGG)$_{49}$AGG(CGG)$_9$AGG(CGG)$_{26}$ (SEQ ID NO: 56) |

Example 6

Determination of AGG Distribution Using an Anchored Assay with an Oppositely Oriented CGG Primer A PCR assay as schematized in FIG. 8H was performed on the 46/97 CGG sample of FIG. 6E with an anchored dT primer (FMR1_R_(CCG)nCCT; SEQ ID NO: 45). The resulting CE profile (FIG. 14) confirmed that the 46 repeat CGG allele had two AGGs at repeat positions 10 and 20; whereas the 97 CGG repeat allele has one AGG at repeat position 11 (counting 5' to 3' from first CGG, as per the literature convention). Thus, mapping assays of the invention can be used to resolve complex CGG/AGG allelic repeat patterns in chromosomal FMR genes.

Example 7

Determination of CGG Repeat Number and AGG Position in Normal and Full Mutation Alleles from Female Samples Using a Reverse Orientation CCG Repeat-Primed PCR Assay CGG repeat number and AGG trinucleotide presence and location were analyzed for 29 clinical chromosomal DNA samples using the three primer CGG repeat-primed PCR assay (FIG. 8A) and the anchored dT reverse PCR assay (FIG. 8H). PCR methods were as described in Examples 4 and 5, except that appropriate primers were used. Results are shown in Table 4. The AGG position numbers follow the literature convention for numbering. NA indicates that no AGG trinucleotides were detected in that allele. Male samples having more than one allele (1, 4, 17, 19, 25, and 26) and female samples having more than two alleles (6 and 20) are believed to derive from a mosaic population of cells within the sample.

TABLE 4

| Sample ID | Sex | CE Allele Peaks CGG repeat equivalents | AGG position |
|---|---|---|---|
| 1 | M | >200 | 11 |
|  |  | 170 | 11 |
| 2 | F | 20 | NA |
|  |  | 31 | 11, 21 |
| 3 | M | 47 | 10, 20 |
| 4 | M | 154 | NA |
|  |  | 174 | NA |
|  |  | >200 | NA |
| 5 | M | 61 | NA |
| 6 | F | 29 | 10, 20 |
|  |  | 60 | 10, 18 |
|  |  | 42** | 10, 18 |
| 7 | M | 51 | 11 |
| 8 | F | 31 | 11, 21 |
|  |  | 47 | 12 |
| 9 | F | 30 | 11, 21 |
|  |  | 50 | 10 |
| 10 | M | 46 | 10, 20 |
| 11 | F | 30 | 11, 21 |
|  |  | 49 | 10 |
| 12 | M | 54 | 10 |
| 13 | M | >200 | 11 |
| 14 | F | 19 | NA |
|  |  | 57 | 10, 20 |
| 15 | M | 57 | 10, 20 |
| 16 | F | 41 | 11, 21, 32 |
|  |  | 57 | 10, 20 |
| 17 | M | 53 | NA |
|  |  | >200 | NA |
|  |  | 152 | NA |
| 18 | F | 30 | 11, 21 |
|  |  | 60 | 10, 20 |
| 19 | M | >200 | 12 |
|  |  | 61 | NA |
| 20 | F | 29 | 10, 20 |
|  |  | >200** | 10 |
|  |  | 54** | 10 |
|  |  | 90** | 10 |
| 21 | M | 50 | 10 |
| 22 | F | 32 | 10, 23 |
|  |  | 53 | 10 |
| 23 | F | 46 | 10, 20 |
|  |  | 97 | 11 |
| 24 | M | 46 | 10, 20 |
| 25 | M | 64 | NA |
|  |  | >200 | 11 |
| 26 | M | 108 | NA |
|  |  | >200 | NA |
| 27 | F | 30 | 11, 21 |
|  |  | >200** | 0 |
| 28 | M | 58 | 10, 20 |
| 29 | F | 29 | 10, 20 |
|  |  | 59 | 10, 20 |

Following PCR amplification with these two assays (FIG. 8A, 8H) and CE analysis, the CGG repeat number and AGG status of alleles were positively determined for 26 of the 29 samples. These two assay formats were unable to positively determine the AGG status for only five alleles from this group. These alleles are designated with "**" in Table 4 (42 CGG allele in sample 6; 54 CGG, 90 CGG, and >200 CGG alleles in sample 20; >200 CGG allele in sample 27). Additional assay methods of the invention (FIG. 8) were used to resolve the CGG repeat number and AGG status for those alleles.

CE analysis of PCR products revealed that two samples (20 and 27) had AGG trinucleotides in one of the normal alleles. For example, in sample 20, AGG trinucleotides are present at positions 10 and 20 in the 29 CGG allele. It is possible that other alleles (e.g., >200 CGG) having AGG trinucleotides at the same exact positions (10, 20) would not be detected by the CGG repeat-primed assay (FIGS. 4, 8A) because AGG dips that are more than ~100 nucleotides away from the 3' end can be difficult to detect due to low peak intensity. Also, in this situation, the anchored dT assay (FIG. 8H) would generate peaks identical to those for the shorter allele, if the AGG location relative to the 5' end of the CGG repeat region is identical in both alleles. Sample 27 presents a similar situation in that AGG trinucleotides were identified at positions 11 and 21 for the 30 CGG allele, but the presence of an AGG trinucleotide in the >200-CGG allele cannot be determined unambiguously.

To resolve these issues, another reflex assay (FIG. 8C) was designed. In a proof of principle experiment, three artificial genomic DNA templates (Coriell Institute for Medical Research; Camden, N.J., USA) having 30 CGG repeats (NA07174), 645 CGG repeats (NA04025), and 30/645 CGG repeats (50% NA07174 and 50% NA04025) were analyzed. The CCG repeat primed assay (FIG. 8C) was performed in the reverse direction with primers FMR1_F_FAM, FMR1_R_(CCG)$_5$ and FMR1_R (SEQ ID NOS: 14, 43, 37). FIG. 15 panel A shows a CE electropherogram produced from the 30 CGG allele (NA07174). Two AGG trinucleotides, one at position 10 and one at position 20, were observed. FIG. 15 panel B shows that there was no AGG trinucleotide in the 645 CGG allele (NA04025). When chromosomal samples having these two alleles were combined to mimic a 30/645 allele female sample, two AGG dips were observed but the signal did not reduce to baseline (FIG. 15, panel C). This result confirmed that the 30 CGG allele had two AGG trinucleotides at positions 10 and 20, whereas the 645 CGG allele did not contain any AGG interrupters at those positions. Thus, this PCR assay was able to interrogate the 5' end of long repeats, such as the 645 CGG allele, to determine the presence or absence of AGG interrupters.

This assay was used to analyze clinical samples 20 and 27, which have full mutation alleles containing >200 CGG repeats (Table 4). FIG. 16 shows the results for sample 20. FIG. 16 panel A shows a CE electropherogram of PCR products following amplification with the standard CGG primed assay (FIG. 8A) with the repeat primer oriented in the forward direction. Two AGGs were observed at the 10 and 20 positions (counting from the 3' end of the CGG repeats). Based on haplotype incidence, the AGGs are normally situated at positions 10, 11, 20, and 21 counting from the 5' end of the CGG repeat region. See, e.g., Zhong et al., *Am. J. Hum. Genet.* 57:351-61 (1995); Kunst et al., *Am. J. Hum. Genet.* 58:513-22 (1996); and Eichler et al., *Hum. Mol. Genet.* 4:2199-208 (1995). Haplotype incidence thus suggests that the AGG interrupters are present in the 29 CGG allele. FIG. 16 panel B shows a CE electropherogram of PCR products following amplification of the same samples using the two primer anchored dT assay oriented in the reverse direction (FIG. 8H). These results confirmed that the two AGG trinucleotides were located at positions 10 and 20 counting from the 5' end of the CGG repeat region. Analysis of the results in FIG. 16, panels A and B revealed that two AGG trinucleotides were located within the 29 CGG allele, whose CGG repeat region therefore had the sequence (CGG)$_9$(AGG)(CGG)$_9$AGG(CGG)$_9$ (SEQ ID NO: 57). A remaining uncertainty with this sample is that the full mutation allele (>200 CGG) may have AGG trinucleotides at the same positions (10, 20) from the 5' end. If so, these AGG sequences may not be detected by a reverse-oriented anchored T assay and differentiated from the AGGs in the short allele (due to the net distance to the forward primer and corresponding reduction in signal intensity observed for mapping 5' sequence elements). Therefore, the PCR assay shown in FIG. 8D, a three primer PCR assay with the CCG repeat primer in the reverse direction, was used to resolve this issue. The assay results (FIG. 16 panel C) confirmed that the >200 CGG allele had one AGG at position 10 from the 5' end of CGG repeats, since signal dropped almost completely to baseline at that position. Thus, both the 29 CGG allele and the 200 CGG allele had AGG trinucleotides at the 10 position. No AGG was present in position 20 of the full mutation allele (>200 CGG) because the signal at that location ddid not reduce to near baseline (FIG. 16 panel C).

Discussion

These analyses demonstrated the occurrence of AGG trinucleotides in full mutation alleles. It is believed that this contrasts to the established position of multiple experts in the field that AGG interrupters do not occur in full mutation alleles. In addition, the methods and assays of the invention are capable of detecting AGG trinucleotide interruptors near the 5' end of the CGG repeat region.

Example 8

Mapping of Interruptor Elements in Sample 27

FIG. 17 shows the AGG mapping results obtained for sample 27 (Table 4). FIG. 17 panel A shows a CE electropherogram following amplification with the standard COG-primed assay in the forward direction (FIG. 8A), which demonstrated that two AGG trinucleotides were present. The CGG peak pattern revealed two AGG, one at position 10 and one at position 20 (from the 3' end of the CGG repeats). Based on knowledge of common haplotypes, AGG interruptions of CGG repeats are characteristically positioned at positions 10, 11, 20, and/or 21 counting from the 5' end of the CGG repeats, which suggests that the AGG repeats are present in the 30 CGG allele in this sample. FIG. 17 panel B presents the results of the two primer, anchored-dT PCR assay oriented in the reverse direction (FIG. 8H). This assay confirmed that the two AGG trinucleotides were at position 11 and 21, counting from the 5' end of the CGG repeats—(CGG)$_{10}$AGG (CGG)$_9$AGG(CGG)$_9$ (SEQ ID NO: 46). A remaining uncertainty with this sample is that the full mutation allele (>200 CGG) may have AGG trinucleotides at the same positions as those in the 30 CGG repeat allele. FIG. 17 panel C gives the results of the three primer CCG-primed PCR assay (FIG. 8D) oriented in the reverse direction. This assay confirmed that the >200 CGG allele has no AGG at either position 11 or 21, because the AGG dip did not reduce to near baseline at these two positions.

Example 9

Resolution of AGG Positions for Low Abundance Alleles in Mosaic Samples Using a Forward Orientation Anchored A PCR Assay Analysis of chromosomal DNA from some samples in Table 4 revealed the presence of low abundance alleles in samples 6 and 20. These are believed to be alleles derived from a mosaic population of cells present in those samples. The forward oriented, anchored-dA PCR assay of the invention (FIG. 8F) was sufficiently sensitive to detect AGG trinucleotides in the sequence of these minor alleles. The results of the two primer anchored-dA assay for samples 6 and 20 are shown in FIG. 18. Amplification of chromosomal DNA from sample 6, using the PCR assay shown in FIG. 8F, and subsequent CE analysis of the PCR products revealed four major peaks, with lengths of 15, 25, 48 and 56 CGG repeats, and two minor peaks, with lengths of 30 and 38 CGG repeats (FIG. 18 panel A). These lengths include the five CGG repeats in the primer, the AGG interruptor, and the number of repeats between the AGG interruptor and the 3' end of the CGG repeat region. The four major peaks confirmed the AGG positions for the two major alleles (positions 10 and 20 for the 29 CGG allele and positions 10 and 18 for the 60 CGG allele—all from the 5' end of the CGG repeats). The two minor peaks confirmed that the minor allele (42 CGG) has two AGG, one at position 10 and one at position 18 (from the 5' end of the CGG repeats). Although both the 42 CGG and 60 CGG alleles have AGG trinucleotides at positions 10 and 18 from the 5' end, since the anchored dA assay is positioned in the forward direction, the size of anchored dA primer PCR amplicons was determined by the number of CGG repeats counted from the 3' end to any AGG that may be present (e.g., 24 for the 42 allele, and 42 for the 60 CGG allele). These PCR products were well separated by CE (30, 38 vs 48, 56 repeat units).

Amplification of chromosomal DNA from sample 20 using the PCR assay shown in FIG. 8F and subsequent CE analysis of the PCR products revealed two primary peaks (FIG. 18B) for the major allele (previously assigned as the 29 CGG allele based on data shown in FIG. 16). However, the assay also revealed two minor allele peaks at position 50 CGG and 86 CGG indicating there were two AGGs in these two minor alleles, both at position 10 when counting from 5' end (i.e., positions 45 and 81 if counting from 3' end).

In conclusion, appropriate combinations of the four assays described above allowed the mapping of AGG trinucleotide interruptors in the CGG repeat regions of each allele of the 29 clinical samples shown in Table 4.

Example 10

Sample Work Flow

One example of an AGG mapping and CGG counting work-flow using the methods of the invention is shown in FIG. 19 and combines some of the assay formats shown in FIG. 8. The workflow shown here is just one example. The assay letter designations refer to those shown in FIG. 8A-H. Some assays used in this workflow can be replaced with other assay formats to achieve the sample purpose.

The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

When methods comprising multiple amplification (e.g., PCR) reactions are recited in a claim, it is to be understood that referring to the reactions as "first," "second," etc., does not refer to the chronological order in which the reactions are performed, and that such claims encompass methods in which the recited reactions are performed in any order or simultaneously, including, for example, performing the "second" reaction before, at the same time as, or after the "first" reaction.

What is claimed is:

1. A method of analyzing at least one CGG-rich region comprised by at least one template in a sample, comprising:
   (a) providing at least two different primers, including a first primer comprising CGG, CCG, GGC, GCG, CGC, or GCC repeats, and a second primer that anneals to a position outside of the CGG-rich region;
   (b) performing PCR with the at least two different primers and the at least one template comprising the at least one CGG-rich region, wherein the PCR produces a set of products;
   (c) resolving the set of products with a high resolution technique to produce a representation of product size and abundance; and
   (d) deriving information about whether an interruptor sequence is present in the at least one CGG-rich region or where within the at least one CGG-rich region an interruptor sequence is located,
   wherein the method is an anchored assay.

2. The method of claim 1, comprising deriving information about where within the CGG-rich region an interruptor sequence is located from said representation.

3. The method of claim 1, wherein the interruptor sequence is an AGG element.

4. The method of claim 1, further comprising deriving information about CGG repeat number from said representation.

5. The method of claim 4, wherein said information about CGG repeat number determines whether the CGG-rich repeat region comprises more or less than 200 CGG repeats.

6. The method of claim 4, wherein said information about CGG repeat number determines the number of CGG repeats present in the CGG-rich region.

7. The method of claim 1, with the proviso that an external standard or calibrator is not used in the deriving of information about whether an interruptor sequence is present in the CGG-rich region or where within the CGG-rich region an interruptor sequence is located from said representation.

8. The method of claim 1, wherein the CGG-rich region is comprised by a 5' UTR of FMR1.

9. The method of claim 1, wherein the CGG-rich region is comprised by a 5' UTR of FMR2.

10. The method of claim 1, wherein the high resolution technique can resolve products differing in length by 3 nucleotides or base pairs.

11. The method of claim 1, wherein the high resolution technique is capillary electrophoresis.

12. The method of claim 1, wherein the representation is an electropherogram.

13. The method of claim 1, wherein deriving information about whether an interruptor sequence is present in the CGG-rich region or where within the CGG-rich region an interruptor sequence is located from said representation comprises determining positions where binding of the first primer was substantially reduced.

14. The method of claim 1, wherein deriving information about whether an interruptor sequence is present in the CGG-rich region or where within the CGG-rich region an interruptor sequence is located from said representation comprises determining one or more product lengths at which the amount of product is substantially reduced compared to the amount of neighboring length products.

15. The method of claim 1, wherein deriving information about whether an interruptor sequence is present in the CGG-rich region or where within the CGG-rich region an interruptor sequence is located from said representation comprises determining one or more product lengths at which the amount of product is reduced by at least 50% compared to the amount of neighboring length products.

16. The method of claim 1, wherein deriving information about whether an interruptor sequence is present in the CGG-rich region or where within the CGG-rich region an interruptor sequence is located from said representation comprises determining one or more product lengths at which the amount of product is reduced by at least 90% compared to the amount of neighboring length products.

17. The method of claim 1, wherein deriving information about whether an interruptor sequence is present in the CGG-rich region or where within the CGG-rich region an interruptor sequence is located from said representation comprises determining one or more product lengths at which the amount of product is reduced by at least 25% compared to the amount of neighboring length products, wherein the CGG-rich region is from an individual heterozygous for the allele comprising the CGG-rich region.

18. The method of claim 1, wherein the first primer comprises four or five CGG or CCG repeats.

19. The method of claim 1, wherein the second primer is chosen from SEQ ID NOs 1-38.

20. The method of claim 1, wherein at least one of the primers comprises a fluorophore.

21. The method of claim 1, wherein the first primer comprises a subsequence chosen from A, T, AG, CT, AGG, and CCT among or at the 3' end of the CGG, CCG, GCG, CGC, GCC, or GGC repeats.

22. The method of claim 21, wherein the first primer comprises an A at the 3' end of the CGG, CCG, GCG, CGC, GCC, or GGC repeats.

23. The method of claim 21, wherein the first primer comprises a CCT at the 3' end of the CGG, CCG, GCG, CGC, GCC, or GGC repeats.

24. The method of claim 1, further comprising detecting at least one interruptor element comprised by the at least one CGG-rich region.

25. The method of claim 24, further comprising determining whether the sample comprises major and minor alleles with differently positioned interruptor elements.

26. The method of claim 1, further comprising providing at least a first additional primer and a second additional primer, the first additional primer comprising CGG, CCG, GCG, CGC, GCC, or GGC repeats; performing a second PCR with at least the first additional primer and the second additional primer, and the at least one template, wherein the second PCR produces a second set of products; and resolving the second set of products with a high resolution technique to produce a second representation of product size and abundance;
wherein the first additional primer is oppositely oriented to the first primer of step (a).

27. A method of analyzing at least one CGG-rich region comprised by at least one template in a sample, comprising:
(a) providing at least three different primers, including a first primer comprising CGG, CCG, GGC, GCG, CGC, or GCC repeats second primer that anneals to a position outside of the CGG-rich region, at least a first additional primer and optionally a second additional primer, the first additional primer comprising CGG, CCG, GCG, CGC, GCC, or GGC repeats;
(b) performing a first PCR with at least the first and second primers and the at least one template comprising the at least one CGG-rich region, wherein the PCR produces a first set of products;
(c) performing a second PCR with at least the first additional primer, a primer chosen from the second primer of step (a) and the second additional primer, and the at least one template, wherein the second PCR produces a second set of products;
(d) resolving the first and second sets of products with a high resolution technique to produce first and second representations of product size and abundance; and
(e) deriving information about whether an interruptor sequence is present in the at least one CGG-rich region or where within the at least one CGG-rich region an interruptor sequence is located,
wherein the first primer of step (a) has a preferential binding activity for sites in the CGG rich region that do not comprise an interruptor element, and wherein the first additional primer has a preferential binding activity for sites in the CGG rich region that comprise an interruptor element.

28. The method of claim 27, wherein the first additional primer comprises an A at the 3' end of the CGG, CCG, GCG, CGC, GCC, or GGC repeats.

29. The method of claim 27, wherein the first additional primer comprises a T at the 3' end of the CGG, CCG, GCG, CGC, GCC, or GGC repeats.

30. The method of claim 27, further comprising determining at least one length of the at least one CGG-rich region.

31. The method of claim 30, wherein the sample comprises genetic material from cells having a ploidy of at least 2 with respect to the CGG region, and the method comprises determining at least two lengths of at least two CGG-rich regions.

32. The method of claim 30, wherein the sample comprises an allele comprising a CGG-rich region comprising at least 100 CGG repeats.

33. The method of claim 27, further comprising determining whether the sample comprises major and minor alleles with differently positioned interruptor elements.

34. The method of claim 27, wherein the first additional primer is oppositely oriented relative to the first primer.

35. The method of claim 34, wherein the first primer binds the CGG-rich region with its 3' end oriented downstream, and the first additional primer binds the CGG-rich region with its 3' end oriented upstream.

36. The method of claim 34, wherein the method comprises detecting at least one interruptor element and determining the size of the CGG-rich region comprising the at least one interruptor element.

37. The method of claim 36, wherein the sample comprises at least first and second alleles, and the first and second alleles comprise CGG-rich regions of different lengths.

38. The method of claim 27, further comprising providing at least a third additional primer and optionally a fourth additional primer, the third additional primer comprising CGG, CCG, GCG, CGC, GCC, or GGC repeats; performing a third PCR with at least the third additional primer, a primer chosen from the second additional primer and the fourth additional primer, and the at least one template, wherein the third PCR produces a third set of products; and resolving the third set of products with a high resolution technique to produce a third representation of product size and abundance;
wherein the third additional primer is oppositely oriented relative to the first primer of step (a) and is different from the first additional primer.

39. The method of claim 38, further comprising determining the presence or absence of interruptor elements within 150 by of either end of at least one allele comprised by the sample.

40. The method of claim 39, further comprising determining at least one position of at least one interruptor element comprised by the at least one allele.

41. A method of analyzing at least one CGG-rich region comprised by at least one template in a sample, comprising:
(a), providing at least four different primers, including a first primer comprising CGG, CCG, GGC, GCG, CGC, or GCC repeats, a second primer that anneals to a position outside of the CGG-rich region, a first additional primer comprising CGG, CCG, GCG, CGC, GCC, or GGC repeats, and a second additional primer:
(b) performing a first PCR with at least the first primer and the second primer and the at least one template comprising the at least one CGG-rich region, wherein the PCR produces a first set of products:
(c) performing a second PCR with at least the first additional primer and the second additional primer, and the at least one template, wherein the second PCR produces a second set of products;
(d) resolving the first set of products with a high resolution technique to produce a first representation of product size and abundance;
(e) resolving the second set of products with a high resolution technique to produce a second representation of product size and abundance; and
(f) deriving information about whether an interruptor sequence is present in the at least one CGG-rich region or where within the at least one CGG-rich region an interruptor sequence is located,
wherein the first additional primer is oppositely oriented to the first primer of step (a), the first primer has a preferential binding activity for sites in the CGG rich region that do not comprise interruptor elements, and the first additional primer has a preferential binding activity for sites in the CGG rich region that comprise interruptor elements.

42. The method of claim 41, wherein the sample comprises at least two alleles comprising CGG-rich regions of different lengths, the method further comprising determining the lengths of the at least two alleles.

43. The method of claim 42, further comprising detecting at least one interruptor element and determining the length of the allele by which the at least one interruptor element is comprised.

44. A method of analyzing at least one CGG-rich region comprised by at least one template in a sample, comprising:
(a) providing at least three different primers, including a first primer comprising CGG, CCG, GCG, CGC, GCC, or GGC repeats and a 5' flap, a second primer that anneals to a position outside of the CGG-rich region, and a third primer having a sequence comprised by the 5' flap of the first primer, wherein the first primer is provided at a lower concentration than the third primer;
(b) performing PCR with the at least three different primers and the at least one template, wherein the PCR produces a set of products;
(c) resolving the set of products with a high resolution technique to produce a representation of product size and abundance; and
(d) deriving information about whether an interruptor sequence is present in the at least one CGG-rich region or where within the at least one CGG-rich region an interruptor sequence is located from said representation,
wherein:
(i) the second primer anneals downstream of the CGG-rich region, and the third primer anneals upstream of the CGG-rich region, or
(ii) the second primer anneals upstream of the CGG-rich region, and the third primer anneals downstream of the CGG-rich region.

45. The method of claim 44, comprising deriving information about where within the CGG-rich region an interruptor sequence is located from said representation.

46. The method of claim 44, wherein the interruptor sequence is an AGG element.

47. The method of claim 44, further comprising deriving information about CGG repeat number from said representation.

48. The method of claim 47, wherein said information about CGG repeat number determines whether the CGG-rich repeat region comprises more or less than 200 CGG repeats.

49. The method of claim 47, wherein said information about CGG repeat number determines the number of CGG repeats present in the CGG-rich region.

50. The method of claim 44, with the proviso that an external standard or calibrator is not used in the deriving of information about whether an interruptor sequence is present in the CGG-rich region or where within the CGG-rich region an interruptor sequence is located from said representation.

51. The method of claim 44, wherein the CGG-rich region is comprised by a 5' UTR of FMR1.

52. The method of claim 44, wherein the CGG-rich region is comprised by a 5' UTR of FMR2.

53. The method of claim 44, wherein the high resolution technique can resolve products differing in length by 3 nucleotides or base pairs.

54. The method of claim 44, wherein the high resolution technique is capillary electrophoresis.

55. The method of claim 44, wherein the representation is an electropherogram.

56. The method of claim 44, wherein deriving information about whether an interruptor sequence is present in the CGG-rich region or where within the CGG-rich region an interruptor sequence is located from said representation comprises determining positions where binding of the first primer was substantially reduced.

57. The method of claim 44, wherein deriving information about whether an interruptor sequence is present in the CGG-rich region or where within the CGG-rich region an interruptor sequence is located from said representation comprises determining one or more product lengths at which the amount of product is substantially reduced compared to the amount of neighboring length products.

58. The method of claim 44, wherein deriving information about whether an interruptor sequence is present in the CGG-rich region or where within the CGG-rich region an interruptor sequence is located from said representation comprises determining one or more product lengths at which the amount of product is reduced by at least 50% compared to the amount of neighboring length products.

59. The method of claim 44, wherein deriving information about whether an interruptor sequence is present in the CGG-rich region or where within the CGG-rich region an interruptor sequence is located from said representation comprises determining one or more product lengths at which the amount of product is reduced by at least 90% compared to the amount of neighboring length products.

60. The method of claim 44, wherein deriving information about whether an interruptor sequence is present in the CGG-rich region or where within the CGG-rich region an interruptor sequence is located from said representation comprises determining one or more product lengths at which the amount of product is reduced by at least 25% compared to the amount of neighboring length products, wherein the CGG-rich region is from an individual heterozygous for the allele comprising the CGG-rich region.

61. The method of claim 44, wherein the first primer comprises four or five CGG or CCG repeats.

62. The method of claim 44, wherein the second primer is chosen from SEQ ID NOs 1-38.

63. The method of claim 44, wherein at least one of the primers comprises a fluorophore.

64. The method of claim 44, wherein the method is a non-anchored assay.

65. The method of claim 44, wherein the first primer and third primer are provided at concentrations such that the third primer is at least 100-fold more abundant than the first primer by molarity.

66. The method of claim 44, wherein the first primer and third primer are provided at concentrations such that the third primer is at least 500-fold more abundant than the first primer by molarity.

67. The method of claim 44, wherein the first primer and third primer are provided at concentrations such that the third primer is at least 900-fold more abundant than the first primer by molarity.

68. The method of claim 44, wherein the second primer anneals downstream of the CGG-rich region, and the third primer anneals upstream of the CGG-rich region.

69. The method of claim 44, wherein the second primer anneals upstream of the CGG-rich region, and the third primer anneals downstream of the CGG-rich region.

70. The method of claim 44, further comprising providing at least a first additional primer and a second additional primer, the first additional primer comprising CGG, CCG, GCG, CGC, GCC, or GGC repeats; performing a second PCR with at least the first additional primer and the second additional primer, and the at least one template, wherein the second PCR produces a second set of products; and resolving the second set of products with a high resolution technique to produce a second representation of product size and abundance;
wherein the first additional primer is oppositely oriented to the first primer of step (a).

71. The method of claim 70, wherein at least one of the first primer and the first additional primer has a preferential binding activity for sites in the CGG rich region that do not comprise interruptor elements.

72. The method of claim 71, wherein the first primer has a preferential binding activity for sites in the CGG rich region that do not comprise interruptor elements, and the first additional primer has a preferential binding activity for sites in the CGG rich region that comprise interruptor elements.

73. The method of claim 72, wherein the sample comprises at least two alleles comprising CGG-rich regions of different lengths, the method further comprising determining the lengths of the at least two alleles.

74. The method of claim 73, further comprising detecting at least one interruptor element and determining the length of the allele by which the at least one interruptor element is comprised.

75. A method of analyzing at least one CGG-rich region comprised by at least one template in a sample, comprising:
(a) providing at least three different primers, including a first primer comprising CGG, CCG, GCG, CGC, GCC, or GGC repeats and a 5' flap, a second primer that anneals to a position outside of the CGG-rich region, and a third primer having a sequence comprised by the 5' flap of the first primer, wherein the first primer is provided at a lower concentration than the third primer;
(b) performing PCR with the at least three different primers and the at least one template, wherein the PCR produces a set of products;
(c) resolving the set of products with a high resolution technique to produce a representation of product size and abundance; and
(d) deriving information about whether an interruptor sequence is present in the at least one CGG-rich region or where within the at least one CGG-rich region an interruptor sequence is located from said representation,
wherein the first primer comprises a subsequence chosen from A, T, AG, CT, AGG, and CCT among or at the 3' end of the CGG, CCG, GCG, CGC, GCC, or GGC repeats.

76. The method of claim 75, wherein the first primer comprises an A at the 3' end of the CGG, CCG, GCG, CGC, GCC, or GGC repeats.

77. The method of claim 75, wherein the first primer comprises a CCT at the 3' end of the CGG, CCG, GCG, CGC, GCC, or GGC repeats.

78. The method of claim 75, further comprising detecting at least one interruptor element comprised by the at least one CGG-rich region.

79. The method of claim 78, further comprising determining whether the sample comprises major and minor alleles with differently positioned interruptor elements.

80. A method of analyzing at least one CGG-rich region comprised by at least one template in a sample, comprising:
(a) providing at least four different primers, including a first primer comprising CGG, CCG, GCG, CGC, GCC, or GGC repeats and a 5' flap, a second primer that anneals to a position outside of the CGG-rich region, a third primer having a sequence comprised by the 5' flap of the first primer, at least a fourth primer, and optionally a fifth primer, the fourth primer comprising CGG, CCG, GCG, CGC, GCC, or GGC repeats, wherein the first primer is provided at a lower concentration than the third primer;

(b) performing PCR with at least the first, second, and third primers and the at least one template, wherein the PCR produces a set of products;

(c) resolving the set of products with a high resolution technique to produce a representation of product size and abundance; and (d) deriving information about whether an interruptor sequence is present in the at least one CGG-rich region or where within the at least one CGG-rich region an interruptor sequence is located from said representation, (e) performing a second PCR with at least the fourth primer, a primer chosen from the second primer of step (a) and the fifth primer, and the at least one template, wherein the second PCR produces a second set of products; and (f) resolving the second set of products with a high resolution technique to produce a second representation of product size and abundance;

wherein the first primer of step (a) has a preferential binding activity for sites in the CGG rich region that do not comprise an interruptor element, and wherein the fourth primer has a preferential binding activity for sites in the CGG rich region that comprise an interruptor element.

81. The method of claim 80, wherein the fourth primer comprises an A at the 3' end of the CGG, CCG, GCG, CGC, GCC, or GGC repeats.

82. The method of claim 80, wherein the fourth primer comprises a T at the 3' end of the CGG, CCG, GCG, CGC, GCC, or GGC repeats.

83. The method of claim 80, further comprising determining at least one length of the at least one CGG-rich region.

84. The method of claim 83, wherein the sample comprises genetic material from cells having a ploidy of at least 2 with respect to the CGG region, and the method comprises determining at least two lengths of at least two CGG-rich regions.

85. The method of claim 83, wherein the sample comprises an allele comprising a CGG-rich region comprising at least 100 CGG repeats.

86. The method of claim 80, further comprising determining whether the sample comprises major and minor alleles with differently positioned interruptor elements.

87. The method of claim 80, wherein the fourth primer is oppositely oriented relative to the first primer.

88. The method of claim 87, wherein the first primer binds the CGG-rich region with its 3' end oriented downstream, and the fourth primer binds the CGG-rich region with its 3' end oriented upstream.

89. The method of claim 88, wherein the method comprises detecting at least one interruptor element and determining the size of the CGG-rich region comprising the at least one interruptor element.

90. The method of claim 89, wherein the sample comprises at least first and second alleles, and the first and second alleles comprise CGG-rich regions of different lengths.

91. The method of claim 80, further comprising providing at least a first additional primer and optionally a second additional primer, the first additional primer comprising CGG, CCG, GCG, CGC, or GCC, GGC repeats; performing a third PCR with at least the first additional primer, a primer chosen from the fifth primer and the second additional primer, and the at least one template, wherein the third PCR produces a third set of products; and resolving the third set of products with a high resolution technique to produce a third representation of product size and abundance;

wherein the first additional primer is oppositely oriented relative to the first primer of step (a) and is different from the fourth primer.

92. The method of claim 91, further comprising determining the presence or absence of interruptor elements within 150 by of either end of at least one allele comprised by the sample.

93. The method of claim 92, further comprising determining at least one position of at least one interruptor element comprised by the at least one allele.

94. A method of analyzing at least one CGG-rich region comprised by at least one template in a sample, comprising:

(a) providing three different primers, wherein the first primer comprises CGG, CCG, GCG, CGC, GCC, or GGC repeats and a 5' flap, the second primer anneals to a position outside of the CGG-rich region, the third primer has the same sequence of the 5' flap of the first primer, and the first primer is provided at a lower concentration than the third primer;

(b) performing PCR with the three different primers and a template comprising the CGG-rich region, wherein the PCR produces a set of products;

(c) resolving the set of products with a high resolution technique to produce a representation of product size and abundance in which products differing in length by three nucleotides are resolved; and (d) deriving information about CGG repeat number from said representation, wherein:
  (i) the second primer anneals downstream of the CGG-rich region, and the third primer anneals upstream of the CGG-rich region; or
  (ii) the second primer anneals upstream of the CGG-rich region, and the third primer anneals downstream of the CGG-rich region.

95. The method of claim 94, wherein said information about CGG repeat number determines whether the CGG-rich repeat region comprises more or less than 200 CGG repeats.

96. The method of claim 94, wherein said information determines the number of CGG repeats present in the CGG-rich region.

97. The method of claim 94, with the proviso that an external standard or calibrator is not used in the deriving of information about CGG repeat number.

98. The method of claim 94, wherein the CGG-rich region is comprised by a 5' UTR chosen from a 5' UTR of FMR1 and a 5' UTR of FMR2.

99. The method of claim 94, wherein the high resolution technique is capillary electrophoresis.

100. The method of claim 94, wherein the representation is an electropherogram.

101. The method of claim 94, wherein the first primer comprises four or five CGG or CCG repeats.

102. The method of claim 94, wherein the second primer is chosen from SEQ ID NOs 1-38.

103. The method of claim 94, wherein at least one of the primers comprises a fluorophore.

104. The method of claim 94, wherein the first primer and third primer are provided at concentrations such that the third primer is at least 100-fold more abundant than the first primer by molarity.

105. The method of claim 94, wherein the second primer anneals downstream of the CGG-rich region, and the third primer anneals upstream of the CGG-rich region.

106. The method of claim 94, wherein the second primer anneals upstream of the CGG-rich region, and the third primer anneals downstream of the CGG-rich region.

* * * * *

UNITED STATES PATENT AND TRADEMARK OFFICE
CERTIFICATE OF CORRECTION

PATENT NO. : 8,679,757 B2
APPLICATION NO. : 12/706472
DATED : March 25, 2014
INVENTOR(S) : Gary J. Latham et al.

It is certified that error appears in the above-identified patent and that said Letters Patent is hereby corrected as shown below:

In the Claims

In claim 27, column 66, line 26, "repeats second primer" should read --repeats, a second primer--.

In claim 27, column 66, line 49, "CGG rich region" should read --CGG-rich region--.

In claim 27, column 66, lines 51-52, "CGG rich region" should read --CGG-rich region--.

In claim 39, column 67, line 33, "150 by" should read --150 bp--.

In claim 41, column 67, line 40, "(a), providing" should read --(a) providing--.

In claim 41, column 67, line 45, "primer:" should read --primer;--.

In claim 41, column 67, line 49, "products:" should read --products;--.

In claim 41, column 67, line 66, "CGG rich region" should read --CGG-rich region--.

In claim 41, column 68, lines 1-2, "CGG rich region" should read --CGG-rich region--.

In claim 71, column 70, line 10, "CGG rich region" should read --CGG-rich region--.

In claim 72, column 70, line 13, "CGG rich region" should read --CGG-rich region--.

In claim 72, column 70, line 16, "CGG rich region" should read --CGG-rich region--.

In claim 80, column 71, line 23, "CGG rich region" should read --CGG-rich region--.

In claim 80, column 71, line 25, "CGG rich region" should read --CGG-rich region--.

Signed and Sealed this
Twelfth Day of August, 2014

Michelle K. Lee
*Deputy Director of the United States Patent and Trademark Office*

CERTIFICATE OF CORRECTION (continued)
U.S. Pat. No. 8,679,757 B2

In claim 91, column 71, line 61, "CGC, or GCC, GGC repeats;" should read --CGC, GCC, or GGC repeats;--.

In claim 92, column 72, line 6, "150 by" should read --150 bp--.

SEQUENCE LISTING

```
<160> NUMBER OF SEQ ID NOS: 71

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
cggtggaggg ccgcctctga gc                                          22

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
caggcgctca gctccgtttc ggttt                                       25

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
cagtcaggcg ctcagctccg tttcg                                       25

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
tccggtggag ggccgcctct gagc                                        24

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
ggttcggcct cagtcaggcg ctcagctccg tttcg                            35
```

<210> SEQ ID NO 6
<211> LENGTH: 36
<212> TYPE: DNA
<213> ORGANISM: Artificial Sequence
<220> FEATURE:
<223> OTHER INFORMATION: primer

<400> SEQUENCE: 6
gggttcggcc tcagtcaggc gctcagctcc gtttcg          36

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
gcgggccggg ggttcggcct cagtca          26

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
cagcgggccg ggggttcggc ctcag          25

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
gcagcgggcc gggggttcgg cctca          25

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
gggccggggg ttcggcctca gtcag          25

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
ggggttcggc ctcagtcagg cgctca          26

<210> SEQ ID NO 12
<211> LENGTH: 27
<212> TYPE: DNA
<213> ORGANISM: Artificial Sequence
<220> FEATURE:
<223> OTHER INFORMATION: primer

```
<400> SEQUENCE: 12
ggggttcggc ctcagtcagg cgctcag                                    27

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
ggcgctcagc tccgtttcgg tttcacttcc                                 30

<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14
tcaggcgctc agctccgttt cggtttca                                   28

<210> SEQ ID NO 15
<211> LENGTH: 26
<212> TYPE: DNA
<213> ORGANISM: Artificial Sequence
<220> FEATURE:
<223> OTHER INFORMATION: primer

<400> SEQUENCE: 15
cacttccggt ggagggccgc ctctga                                     26

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
ttccggtgga gggccgcctc tgagc                                      25

<210> SEQ ID NO 17
<211> LENGTH: 25
<212> TYPE: DNA
<213> ORGANISM: Artificial Sequence
<220> FEATURE:
<223> OTHER INFORMATION: primer

<400> SEQUENCE: 17
cgcacttcca ccaccagctc ctcca                                      25

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
ggagcccgcc cccgagaggt g                                          21

<210> SEQ ID NO 19
<211> LENGTH: 21
<212> TYPE: DNA
```

```
<213> ORGANISM: Artificial Sequence
<220> FEATURE:
<223> OTHER INFORMATION: primer

<400> SEQUENCE: 19
gggagcccgc ccccgagagg t                                          21

<210> SEQ ID NO 20
<211> LENGTH: 26
<212> TYPE: DNA
<213> ORGANISM: Artificial Sequence
<220> FEATURE:
<223> OTHER INFORMATION: primer

<400> SEQUENCE: 20
cgcacttcca ccaccagctc ctccat                                     26

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
cgggagcccg cccccgagag gtg                                        23

<210> SEQ ID NO 22
<211> LENGTH: 23
<212> TYPE: DNA
<213> ORGANISM: Artificial Sequence
<220> FEATURE:
<223> OTHER INFORMATION: primer

<400> SEQUENCE: 22
ccgggagccc gccccgaga ggt                                         23

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
ccgggagccc gccccgaga ggtg                                        24

<210> SEQ ID NO 24
<211> LENGTH: 26
<212> TYPE: DNA
<213> ORGANISM: Artificial Sequence
<220> FEATURE:
<223> OTHER INFORMATION: primer

<400> SEQUENCE: 24
cgccgggagc ccgccccccga gaggtg                                    26

<210> SEQ ID NO 25
<211> LENGTH: 26
<212> TYPE: DNA
<213> ORGANISM: Artificial Sequence
<220> FEATURE:
<223> OTHER INFORMATION: primer

<400> SEQUENCE: 25
gcgccgggag cccgccccccg agaggt                                    26
```

```
<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
cgccgggagc ccgcccccga gaggt                                      25

<210> SEQ ID NO 27
<211> LENGTH: 28
<212> TYPE: DNA
<213> ORGANISM: Artificial Sequence
<220> FEATURE:
<223> OTHER INFORMATION: primer

<400> SEQUENCE: 27
gcgccattgg agccccgcac ttccacca                                   28

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
gcgccattgg agccccgcac ttcca                                      25

<210> SEQ ID NO 29
<211> LENGTH: 25
<212> TYPE: DNA
<213> ORGANISM: Artificial Sequence
<220> FEATURE:
<223> OTHER INFORMATION: primer

<400> SEQUENCE: 29
agcgccattg gagccccgca cttcc                                      25

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30
cgccattgga gccccgcact tccac                                      25

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
ttggagcccc gcacttccac cacca                                      25

<210> SEQ ID NO 32
<211> LENGTH: 28
<212> TYPE: DNA
<213> ORGANISM: Artificial Sequence
<220> FEATURE:
<223> OTHER INFORMATION: primer
```

-continued

```
<400> SEQUENCE: 32
agccccgcac ttccaccacc agctcctc                                           28

<210> SEQ ID NO 33
<211> LENGTH: 28
<212> TYPE: DNA
<213> ORGANISM: Artificial Sequence
<220> FEATURE:
<223> OTHER INFORMATION: primer

<400> SEQUENCE: 33
gagccccgca cttccaccac cagctcct                                           28

<210> SEQ ID NO 34
<211> LENGTH: 28
<212> TYPE: DNA
<213> ORGANISM: Artificial Sequence
<220> FEATURE:
<223> OTHER INFORMATION: primer

<400> SEQUENCE: 34
cattggagcc ccgcacttcc accaccag                                           28

<210> SEQ ID NO 35
<211> LENGTH: 30
<212> TYPE: DNA
<213> ORGANISM: Artificial Sequence
<220> FEATURE:
<223> OTHER INFORMATION: primer

<400> SEQUENCE: 35
cccgcacttc caccaccagc tcctccatct                                         30

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
tagaaagcgc cattggagcc ccgcacttcc                                         30

<210> SEQ ID NO 37
<211> LENGTH: 26
<212> TYPE: DNA
<213> ORGANISM: Artificial Sequence
<220> FEATURE:
<223> OTHER INFORMATION: primer

<400> SEQUENCE: 37
aagcgccatt ggagccccgc acttcc                                             26

<210> SEQ ID NO 38
<211> LENGTH: 36
<212> TYPE: DNA
<213> ORGANISM: Artificial Sequence
<220> FEATURE:
<223> OTHER INFORMATION: primer

<400> SEQUENCE: 38
tcaggcgctc agctccgttt cggtttcact tccggt                                  36

<210> SEQ ID NO 39
<211> LENGTH: 36
<212> TYPE: DNA
```

```
<213> ORGANISM: Artificial Sequence
<220> FEATURE:
<223> OTHER INFORMATION: primer

<400> SEQUENCE: 39
agcgtctact gtctcggcac ttgcccgccg ccgccg                                36

<210> SEQ ID NO 40
<211> LENGTH: 28
<212> TYPE: DNA
<213> ORGANISM: Artificial Sequence
<220> FEATURE:
<223> OTHER INFORMATION: primer

<400> SEQUENCE: 40
tcaggcgctc agctccgttt cggtttca                                        28

<210> SEQ ID NO 41
<211> LENGTH: 43
<212> TYPE: DNA
<213> ORGANISM: Artificial Sequence
<220> FEATURE:
<223> OTHER INFORMATION: primer

<400> SEQUENCE: 41
tcaggcgctc agctccgttt cggtttcacg gcggcggcgg cgg                       43

<210> SEQ ID NO 42
<211> LENGTH: 90
<212> TYPE: DNA
<213> ORGANISM: Homo sapiens

<400> SEQUENCE: 42
cggcggcggc ggcggcggcg gcggcggcgg aggcggcggc ggcggcggcg gcggcggcgg     60
aggcggcggc ggcggcggcg gcggcggcgg                                      90

<210> SEQ ID NO 43
<211> LENGTH: 41
<212> TYPE: DNA
<213> ORGANISM: Artificial Sequence
<220> FEATURE:
<223> OTHER INFORMATION: primer

<400> SEQUENCE: 43
aagcgccatt ggagccccgc acttccccgc cgccgccgcc g                         41

<210> SEQ ID NO 44
<211> LENGTH: 44
<212> TYPE: DNA
<213> ORGANISM: Artificial Sequences
<220> FEATURE:
<223> OTHER INFORMATION: primer

<400> SEQUENCE: 44
tcaggcgctc agctccgttt cggtttcacg gcggcggcgg cgga                      44

<210> SEQ ID NO 45
<211> LENGTH: 41
<212> TYPE: DNA
<213> ORGANISM: Artificial Sequence
<220> FEATURE:
<223> OTHER INFORMATION: primer

<400> SEQUENCE: 45
aagcgccatt ggagccccgc acttccccgc cgccgccgcc t                         41
```

```
<210> SEQ ID NO 46
<211> LENGTH: 90
<212> TYPE: DNA
<213> ORGANISM: Homo sapiens

<400> SEQUENCE: 46
cggcggcggc ggcggcggcg gcggcggcgg aggcggcggc ggcggcggcg gcggcggcgg      60
aggcggcggc ggcggcggcg gcggcggcgg                                      90

<210> SEQ ID NO 47
<211> LENGTH: 141
<212> TYPE: DNA
<213> ORGANISM: Homo sapiens

<400> SEQUENCE: 47
cggcggcggc ggcggcggcg gcggcggagg cggcggcggc ggcggcggcg gcggcggagg      60
cggcggcggc ggcggcggcg gcggcggcgg cggcggcggc ggcggcggcg gcggcggcgg     120
cggcggcggc ggcggcggcg g                                              141

<210> SEQ ID NO 48
<211> LENGTH: 183
<212> TYPE: DNA
<213> ORGANISM: Homo sapiens

<400> SEQUENCE: 48
cggcggcggc ggcggcggcg gcggcggcgg cggcggcggc ggcggcggcg gcggcggcgg      60
cggcggcggc ggcggcggcg gcggcggcgg cggcggcggc ggcggcggcg gcggcggcgg     120
cggcggcggc ggcggcggcg gcggcggcgg cggcggcggc ggcggcggcg gcggcggcgg     180
cgg                                                                  183

<210> SEQ ID NO 49
<211> LENGTH: 60
<212> TYPE: DNA
<213> ORGANISM: Homo sapiens

<400> SEQUENCE: 49
cggcggcggc ggcggcggcg gcggcggcgg cggcggcggc ggcggcggcg gcggcggcgg      60

<210> SEQ ID NO 50
<211> LENGTH: 93
<212> TYPE: DNA
<213> ORGANISM: Homo sapiens

<400> SEQUENCE: 50
cggcggcggc ggcggcggcg gcggcggcgg aggcggcggc ggcggcggcg gcggcggcgg      60
aggcggcggc ggcggcggcg gcggcggcgg cgg                                  93

<210> SEQ ID NO 51
<211> LENGTH: 138
<212> TYPE: DNA
<213> ORGANISM: Homo sapiens

<400> SEQUENCE: 51
cggcggcggc ggcggcggcg gcggcggagg cggcggcggc ggcggcggcg gcggcggagg      60
cggcggcggc ggcggcggcg gcggcggcgg cggcggcggc ggcggcggcg gcggcggcgg     120
cggcggcggc ggcggcgg                                                  138

<210> SEQ ID NO 52
```

```
<211> LENGTH: 291
<212> TYPE: DNA
<213> ORGANISM: Homo sapiens

<400> SEQUENCE: 52
cggcggcggc ggcggcggcg gcggcggcgg aggcggcggc ggcggcggcg gcggcggcgg      60
cggcggcggc ggcggcggcg gcggcggcgg cggcggcggc ggcggcggcg gcggcggcgg     120
cggcggcggc ggcggcggcg gcggcggcgg cggcggcggc ggcggcggcg gcggcggcgg     180
cggcggcggc ggcggcggcg gcggcggcgg cggcggcggc ggcggcggcg gcggcggcgg     240
cggcggcggc ggcggcggcg gcggcggcgg cggcggcggc ggcggcggcg g              291

<210> SEQ ID NO 53
<211> LENGTH: 60
<212> TYPE: DNA
<213> ORGANISM: Homo sapiens

<400> SEQUENCE: 53
cggcggcggc ggcggcggcg gcggcggagg cggcggcggc ggcggcggcg gcggcggcgg      60

<210> SEQ ID NO 54
<211> LENGTH: 93
<212> TYPE: DNA
<213> ORGANISM: Homo sapiens

<400> SEQUENCE: 54
cggcggcggc ggcggcggcg gcggcggcgg aggcggcggc ggcggcggcg gcggcggcgg      60
cggcggcggc ggcggcggcg gcggcggcgg cgg                                   93

<210> SEQ ID NO 55
<211> LENGTH: 138
<212> TYPE: DNA
<213> ORGANISM: Homo sapiens

<400> SEQUENCE: 55
cggcggcggc ggcggcggcg gcggcggcgg cggcggcggc ggcggcggcg gcggcggcgg      60
cggcggcggc ggcggcggcg gcggcggcgg cggcggcggc ggcggcggcg gcggcggcgg     120
cggcggcggc ggcggcgg                                                   138

<210> SEQ ID NO 56
<211> LENGTH: 291
<212> TYPE: DNA
<213> ORGANISM: Homo sapiens

<400> SEQUENCE: 56
cggcggcggc ggcggcggcg gcggcggcgg aggcggcggc ggcggcggcg gcggcggcgg      60
cggcggcggc ggcggcggcg gcggcggcgg cggcggcggc ggcggcggcg gcggcggcgg     120
cggcggcggc ggcggcggcg gcggcggcgg cggcggcggc ggcggcggcg gcggcggcgg     180
aggcggcggc ggcggcggcg gcggcggcgg aggcggcggc ggcggcggcg gcggcggcgg     240
cggcggcggc ggcggcggcg gcggcggcgg cggcggcggc ggcggcggcg g              291

<210> SEQ ID NO 57
<211> LENGTH: 87
<212> TYPE: DNA
<213> ORGANISM: Homo sapiens

<400> SEQUENCE: 57
cggcggcggc ggcggcggcg gcggcggagg cggcggcggc ggcggcggcg gcggcggagg      60
```

```
cggcggcggc ggcggcggcg gcggcgg                                           87
```

<210> SEQ ID NO 58
<211> LENGTH: 126
<212> TYPE: DNA
<213> ORGANISM: Homo sapiens

<400> SEQUENCE: 58

```
cggcggcggc ggcggcggcg gcggcggagg cggcggcggc ggcggcggcg gaggcggcgg      60
cggcggcggc ggcggcggcg gcggcggcgg cggcggcggc ggcggcggcg gcggcggcgg     120
cggcgg                                                                126
```

<210> SEQ ID NO 59
<211> LENGTH: 180
<212> TYPE: DNA
<213> ORGANISM: Homo sapiens

<400> SEQUENCE: 59

```
cggcggcggc ggcggcggcg gcggcggagg cggcggcggc ggcggcggcg gaggcggcgg      60
cggcggcggc ggcggcggcg gcggcggcgg cggcggcggc ggcggcggcg gcggcggcgg     120
cggcggcggc ggcggcggcg gcggcggcgg cggcggcggc ggcggcggcg gcggcggcgg     180
```

<210> SEQ ID NO 60
<211> LENGTH: 162
<212> TYPE: DNA
<213> ORGANISM: Homo sapiens

<400> SEQUENCE: 60

```
cggcggcggc ggcggcggcg gcggcggagg cggcggcggc ggcggcggcg gcggcggcgg      60
cggcggcggc ggcggcggcg gcggcggcgg cggcggcggc ggcggcggcg gcggcggcgg     120
cggcggcggc ggcggcggcg gcggcggcgg cggcggcggc gg                        162
```

<210> SEQ ID NO 61
<211> LENGTH: 270
<212> TYPE: DNA
<213> ORGANISM: Homo sapiens

<400> SEQUENCE: 61

```
cggcggcggc ggcggcggcg gcggcggagg cggcggcggc ggcggcggcg gcggcggcgg      60
cggcggcggc ggcggcggcg gcggcggcgg cggcggcggc ggcggcggcg gcggcggcgg     120
cggcggcggc ggcggcggcg gcggcggcgg cggcggcggc ggcggcggcg gcggcggcgg     180
cggcggcggc ggcggcggcg gcggcggcgg cggcggcggc ggcggcggcg gcggcggcgg     240
cggcggcggc ggcggcggcg gcggcggcgg                                      270
```

<210> SEQ ID NO 62
<211> LENGTH: 111
<212> TYPE: DNA
<213> ORGANISM: Homo sapiens

<400> SEQUENCE: 62

```
cggcggcggc ggcggcggcg gcggcggagg cggcggcggc ggcggcggcg gaggcggcgg      60
cggcggcggc ggcggcggcg gaggcggcgg cggcggcggc ggcggcggcg g              111
```

<210> SEQ ID NO 63
<211> LENGTH: 171
<212> TYPE: DNA
<213> ORGANISM: Homo sapiens -continued

```
<400> SEQUENCE: 63
cggcggcggc ggcggcggcg gcggcggagg cggcggcggc ggcggcggcg gcggcggagg      60
cggcggcggc ggcggcggcg gcggcggcgg cggcggcggc ggcggcggcg gcggcggcgg     120
cggcggcggc ggcggcggcg gcggcggcgg cggcggcggc ggcggcggcg g              171

<210> SEQ ID NO 64
<211> LENGTH: 234
<212> TYPE: DNA
<213> ORGANISM: Homo sapiens

<400> SEQUENCE: 64
cggcggcggc ggcggcggcg gcggcggcg  aggcggcggc ggcggcggcg gcggcggcgg      60
cggcggcggc ggcggcggcg gcggcggcgg cggcggcggc ggcggcggcg gcggcggcgg     120
cggcggcggc ggcggcggcg gcggcggcgg cggcggcggc ggcggcggcg gcggcggcgg     180
cggcggcggc ggcggcggcg gcggcggcgg cggcggcggc ggcggcggcg gcgg           234

<210> SEQ ID NO 65
<211> LENGTH: 300
<212> TYPE: DNA
<213> ORGANISM: Homo sapiens

<400> SEQUENCE: 65
cggcggcggc ggcggcggcg gcggcggcgg aggcggcggc ggcggcggcg gcggcggcgg      60
cggcggcggc ggcggcggcg gcggcggcgg cggcggcggc ggcggcggcg gcggcggcgg     120
cggcggcggc ggcggcggcg gcggcggcgg cggcggcggc ggcggcggcg gcggcggcgg     180
cggcggcggc ggcggcggcg gcggcggcgg cggcggcggc ggcggcggcg gcggcggcgg     240
cggcggcggc ggcggcggcg gcggcggcgg cggcggcggc ggcggcggcg gcggcggcgg     300

<210> SEQ ID NO 66
<211> LENGTH: 366
<212> TYPE: DNA
<213> ORGANISM: Homo sapiens

<400> SEQUENCE: 66
cggcggcggc ggcggcggcg gcggcggcgg aggcggcggc ggcggcggcg gcggcggcgg      60
cggcggcggc ggcggcggcg gcggcggcgg cggcggcggc ggcggcggcg gcggcggcgg     120
cggcggcggc ggcggcggcg gcggcggcgg cggcggcggc ggcggcggcg gcggcggcgg     180
cggcggcggc ggcggcggcg gcggcggcgg cggcggcggc ggcggcggcg gcggcggcgg     240
cggcggcggc ggcggcggcg gcggcggcgg cggcggcggc ggcggcggcg gcggcggcgg     300
cggcggcggc ggcggcggcg gcggcggcgg cggcggcggc ggcggcggcg gcggcggcgg     360
cggcgg                                                                366

<210> SEQ ID NO 67
<211> LENGTH: 60
<212> TYPE: DNA
<213> ORGANISM: Homo sapiens

<400> SEQUENCE: 67
cggcggcggc ggcggcggcg gcggcggcgg aggcggcggc ggcggcggcg gcggcggcgg      60

<210> SEQ ID NO 68
<211> LENGTH: 138
<212> TYPE: DNA
<213> ORGANISM: Homo sapiens
```

```
<400> SEQUENCE: 68
cggcggcggc ggcggcggcg gcggcggcgg cggcggcggc ggcggcggcg gcggcggagg        60
cggcggcggc ggcggcggcg gcggcggcgg cggcggcggc ggcggcggcg gcggcggcgg       120
cggcggcggc ggcggcgg                                                     138

<210> SEQ ID NO 69
<211> LENGTH: 291
<212> TYPE: DNA
<213> ORGANISM: Homo sapiens

<400> SEQUENCE: 69
cggcggcggc ggcggcggcg gcggcggcgg aggcggcggc ggcggcggcg gcggcggcgg        60
cggcggcggc ggcggcggcg gcggcggcgg cggcggcggc ggcggcggcg gcggcggcgg       120
cggcggcggc ggcggcggcg gcggcggcgg cggcggcggc ggcggcggcg gcggcggcgg       180
aggcggcggc ggcggcggcg gcggcggcgg cggcggcggc ggcggcggcg gcggcggcgg       240
cggcggcggc ggcggcggcg gcggcggcgg cggcggcggc ggcggcggcg g                291

<210> SEQ ID NO 70
<211> LENGTH: 138
<212> TYPE: DNA
<213> ORGANISM: Homo sapiens

<400> SEQUENCE: 70
cggcggcggc ggcggcggcg gcggcggagg cggcggcggc ggcggcggcg gcggcggcgg        60
cggcggcggc ggcggcggcg gcggcggcgg cggcggcggc ggcggcggcg gcggcggcgg       120
cggcggcggc ggcggcgg                                                     138

<210> SEQ ID NO 71
<211> LENGTH: 291
<212> TYPE: DNA
<213> ORGANISM: Homo sapiens

<400> SEQUENCE: 71
cggcggcggc ggcggcggcg gcggcggcgg aggcggcggc ggcggcggcg gcggcggcgg        60
cggcggcggc ggcggcggcg gcggcggcgg cggcggcggc ggcggcggcg gcggcggcgg       120
cggcggcggc ggcggcggcg gcggcggcgg cggcggcggc ggcggcggcg gcggcggcgg       180
cggcggcggc ggcggcggcg gcggcggcgg aggcggcggc ggcggcggcg gcggcggcgg       240
cggcggcggc ggcggcggcg gcggcggcgg cggcggcggc ggcggcggcg g                291
```